(12) United States Patent
Shibayama et al.

(10) Patent No.: US 8,772,200 B2
(45) Date of Patent: Jul. 8, 2014

(54) NITROGEN-CONTAINING HETEROCYCLIC COMPOUND AND AGRICULTURAL FUNGICIDE

(75) Inventors: Kotaro Shibayama, Odawara (JP); Jun Inagaki, Odawara (JP); Yuto Saiki, Odawara (JP); Akira Mitani, Odawara (JP); Raito Kuwahara, Odawara (JP); Motoaki Sato, Odawara (JP); Satoshi Nishimura, Odawara (JP); Mami Kuboki, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 66 days.

(21) Appl. No.: 13/519,209

(22) PCT Filed: Dec. 28, 2010

(86) PCT No.: PCT/JP2010/073683
§ 371 (c)(1),
(2), (4) Date: Jun. 26, 2012

(87) PCT Pub. No.: WO2011/081174
PCT Pub. Date: Jul. 7, 2011

(65) Prior Publication Data
US 2012/0289702 A1   Nov. 15, 2012

(30) Foreign Application Priority Data
Jan. 4, 2010   (JP) ................. 2010-000194

(51) Int. Cl.
| C07D 215/60 | (2006.01) |
| A01N 43/42 | (2006.01) |
| A01N 43/40 | (2006.01) |
| C07D 215/20 | (2006.01) |
| C07D 215/18 | (2006.01) |

(52) U.S. Cl.
CPC ............. *A01N 43/42* (2013.01); *A01N 43/40* (2013.01); *C07D 215/60* (2013.01); *C07D 215/20* (2013.01); *C07D 215/18* (2013.01)
USPC .............................. 504/247; 546/153; 546/159

(58) Field of Classification Search
CPC .. C07D 215/60; C07D 215/20; C07D 215/18; A01N 43/42; A01N 43/40
USPC ................... 546/159, 153; 504/247
See application file for complete search history.

(56) References Cited

U.S. PATENT DOCUMENTS

2006/0211739 A1   9/2006   Perez-Medrano et al.

FOREIGN PATENT DOCUMENTS

| JP | 54-014977 | 2/1979 |
| JP | 62-103051 | 5/1987 |
| JP | 07-285938 | 10/1995 |
| JP | 10-067746 | 3/1998 |
| JP | 2002-501945 | 1/2002 |
| JP | 2004-514663 | 5/2004 |
| JP | 2005-531518 | 10/2005 |
| JP | 2006-507336 | 3/2006 |
| JP | 2008-088139 | 4/2008 |
| JP | 2008-521872 | 6/2008 |
| JP | 2008-528590 | 7/2008 |
| JP | 2009-507024 | 2/2009 |
| JP | 2009-091320 | 4/2009 |
| WO | 92/17452 | 10/1992 |
| WO | 99/38845 A1 | 8/1999 |
| WO | 03/063861 | 8/2003 |
| WO | 2005/070917 | 8/2005 |
| WO | 2006/098308 | 9/2006 |
| WO | 2007/011022 | 1/2007 |
| WO | 2007/088978 A1 | 8/2007 |
| WO | 2007/117180 | 10/2007 |
| WO | 2008/068270 | 6/2008 |
| WO | 2008/101682 A2 | 8/2008 |
| WO | 2009/021696 | 2/2009 |
| WO | 2010/026771 | 3/2010 |

OTHER PUBLICATIONS

Burgos, Angev Chem Int, vol. 45, pp. 4321-4326, 2005.*
Altman, Org Lett, vol. 9 (4), pp. 643-646, 2007.*
Toffano, CA 153:555220, abstract only of Science of Synthesis, vol. date 2008, 42, pp. 347-389, 2009.*
Burgos et al., "Significantly Improved Method for the Pd-Catalyzed Coupling of Phenols with Aryl Halides: Understanding Ligand Effects", Angewandte Chemie International Edition, vol. 45, Issue 26, pp. 4321-4326, Jun. 26, 2006.

(Continued)

*Primary Examiner* — D M Seaman
(74) *Attorney, Agent, or Firm* — Kenyon & Kenyon, LLP

(57) ABSTRACT

Provided is an agricultural fungicide that contains at least one selected from the group consisting of a novel nitrogen-containing heterocyclic compound represented by Formula (I), a salt thereof, or an N-oxide compound thereof. In Formula (I), R represents a group represented by $CR^1R^2R^3$ or a cyano group. $R^1$ to $R^3$ each independently represents a hydrogen atom, an unsubstituted or substituted $C_{1-8}$ alkyl group, an unsubstituted or substituted hydroxyl group, or the like. R4 or R5 represents a halogeno group or the like. Y or Z represents a carbon atom or the like, and A or D represents a benzene ring or the like. X represents an oxygen atom or a nitrogen atom or the like.

Formula (I)

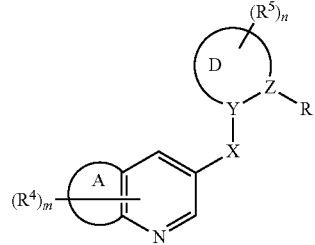

9 Claims, No Drawings

(56) References Cited

OTHER PUBLICATIONS

EP Communication including Supplementary European Search Report from EP Appln. No. 10841029.1, May 8, 2013, 6 pages.
International Search Report issued for PCT/JP2010/073683, dated Mar. 1, 2011, 10 pages (with English translation).
Yamamoto, Yasunori, et al., "Cyclic Triolborates: Air- and Water-Stable Ate Complexes of Organoboronic Acids", Angew. Chem. Int. Ed., 2008, vol. 47, pp. 928-931.
Calaway, Paul K., et al., "Utilization of Aryloxy Ketones in the Synthesis of Quinolines by the Pfitzinger Reaction", Jun. 1939, vol. 61, No. 6, pp. 1355-1358.
Royer, Rene, et al., "Sur la formation des aldehydes aromatiques par pyrodecomposition des aryloxyacetophenones", Helvetica Chimica Acta, 1959, vol. 42, No. 7, pp. 2364-2370.
Ruiz, Javier, et al., "Intramolecular cyclisation of functionalised heteroaryllithiums. Synthesis of novel indolizinone-based compounds", Tetrahedron, 2006, vol. 62, No. 26, pp. 6182-6189.
Chan, David C. M., et al., "Design, Synthesis, and Antifolate Activity of New Analogues of Piritrexim and Other Diamonopyrimidine Dihdryofolate Reductase Inhibitors with ω-Carboxyalkoxy or ω-Carboxy-1-alkynyl Substitution in the Side Chain", Journal of Medicinal Chemistry, 2005, vol. 48, No. 13, pp. 4420-4431.
Office Action issued in KR Appln. No. 10-2012-7016781, dated Oct. 29, 2013, 10 pages (with English translation).
Office Action issued in JP Appln. No. 2011-547711, dated Nov. 19, 2013, 10 pages (with English translation).
Nakashima et al., "Ring Contraction of 3-Hydroxyguinolines to Oxindoles with Hydrogen Peroxide in Acetic Acid," Chem. Pharm. Bull, Japan, 1969, 17(11), pp. 2293-2298.
Bhimani, "Studies on Compounds of Therapeutic Interest," Saurashtra University, doctorate thesis, India, 2004, 280 pages.
Notice of Allowance issued in the JP Application No. 2011-547711, dated Feb. 12, 2014, 8 pages.

\* cited by examiner

NITROGEN-CONTAINING HETEROCYCLIC COMPOUND AND AGRICULTURAL FUNGICIDE

TECHNICAL FIELD

The present invention relates to novel nitrogen-containing heterocyclic compounds and an agricultural fungicide which contains at least one selected from the group consisting of the nitrogen-containing heterocyclic compounds as an active ingredient.

Priority is claimed on Japanese Patent Application No. 2010-000194, filed Jan. 4, 2010, the content of which is incorporated herein by reference.

BACKGROUND ART

In agricultural crop cultivation, a variety of control agents are used to deal with crop diseases. However, there are very few agents which fully satisfy the requirements for use as a control agent due to reasons such as an insufficient control effect, limited use due to the emergence of agent-resistant pathogens, phytotoxic or contaminating effects on plants, or toxicity to humans, domestic animals, and fish, and an adverse effect on the environment. Therefore, the need for agents having fewer disadvantages of this kind and which are safe to use is required.

Related to the present invention, in the following Patent Document 1 or 2, quinoline derivatives having similar chemical structures to the compounds according to the present invention, and agricultural fungicides containing the quinoline derivatives as active ingredients, are disclosed.

DOCUMENTS OF RELATED ART

Patent Documents

[Patent Document 1] Pamphlet of WO2005/070917
[Patent Document 2] Pamphlet of WO2007/011022

SUMMARY OF THE INVENTION

Problems to be Solved by the Invention

An object of the present invention is to provide a novel nitrogen-containing heterocyclic compound, and a salt thereof or N-oxide compound thereof, and an agricultural fungicide, which has reliable effects, is safe to use and contains at least one selected from the group consisting of the nitrogen-containing heterocyclic compound, the salt and N-oxide compound thereof as an active ingredient.

Means to Solve the Problems

The inventors have studied intensively in order to solve the above problems. As a result, a nitrogen-containing heterocyclic compound represented by Formula (I), a salt thereof or an N-oxide compound thereof were obtained. It was also discovered that the nitrogen-containing heterocyclic compound, the salt thereof or the N-oxide compound thereof are useful as an active ingredient of an agricultural fungicide, which has reliable effects and is safe to use. The present invention was completed with further studies based on these findings.

That is, the present invention includes the following aspects.

<1> A nitrogen-containing heterocyclic compound represented by Formula (I), a salt thereof, or an N-oxide compound thereof.

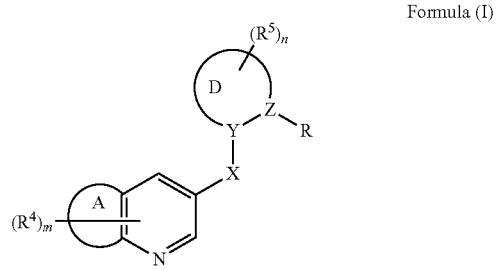

Formula (I)

In Formula (I), R represents a group represented by $CR^1R^2R^3$, an unsubstituted or substituted $C_{6-10}$ aryl group, or a cyano group;

$R^1$ to $R^3$ each independently represents a hydrogen atom, an unsubstituted or substituted $C_{1-8}$ alkyl group, an unsubstituted or substituted $C_{2-8}$ alkenyl group, an unsubstituted or substituted $C_{2-8}$ alkynyl group, an unsubstituted or substituted $C_{3-8}$ cycloalkyl group, an unsubstituted or substituted $C_{4-8}$ cycloalkenyl group, an unsubstituted or substituted $C_{6-10}$ aryl group, an unsubstituted or substituted heterocyclic group, an unsubstituted or substituted $C_{1-8}$ acyl group, an unsubstituted or substituted (1-imino)$C_{1-8}$ alkyl group, an unsubstituted or substituted carboxyl group, an unsubstituted or substituted carbamoyl group, an unsubstituted or substituted hydroxyl group, an unsubstituted or substituted amino group, an unsubstituted or substituted mercapto group, a substituted sulfonyl group, a halogeno group, a cyano group, or a nitro group;

excepting in which: $R^1$ to $R^3$ are all hydrogen atoms; $R^1$ to $R^3$ are all unsubstituted $C_{1-8}$ alkyl groups; any one of $R^1$ to $R^3$ is a hydrogen atom and the remaining two are both unsubstituted $C_{1-8}$ alkyl groups; and, any one of $R^1$ to $R^3$ is an unsubstituted $C_{1-8}$ alkyl group and the remaining two are both hydrogen atoms;

$R^1$ and $R^2$ may be joined to form an unsubstituted or substituted 5- to 8-membered ring, or to form O=, $R^aR^bC=$, or R'—N=;

$R^a$ represents a hydrogen atom or an unsubstituted or substituted $C_{1-8}$ alkyl group;

$R^b$ represents a hydrogen atom or an unsubstituted or substituted $C_{1-8}$ alkyl group;

R' represents an unsubstituted or substituted hydroxyl group, or an unsubstituted or substituted $C_{1-8}$ alkyl group;

$R^4$ each independently represents an unsubstituted or substituted $C_{1-8}$ alkyl group, an unsubstituted or substituted $C_{2-8}$ alkenyl group, an unsubstituted or substituted $C_{2-8}$ alkynyl group, an unsubstituted or substituted $C_{3-8}$ cycloalkyl group, an unsubstituted or substituted $C_{4-8}$ cycloalkenyl group, an unsubstituted or substituted $C_{6-10}$ aryl group, an unsubstituted or substituted heterocyclic group, an unsubstituted or substituted $C_{1-8}$ acyl group, an unsubstituted or substituted (1-imino)$C_{1-8}$ alkyl group, an unsubstituted or substituted carboxyl group, an unsubstituted or substituted carbamoyl group, an unsubstituted or substituted hydroxyl group, an unsubstituted or substituted amino group, an unsubstituted or substituted mercapto group, a substituted sulfonyl group, a halogeno group, a cyano group, or a nitro group;

m represents a number of $R^4$ and is an integer of 0 to 6;

$R^5$ each independently represents an unsubstituted or substituted $C_{1-8}$ alkyl group, an unsubstituted or substituted $C_{2-8}$ alkenyl group, an unsubstituted or substituted $C_{2-8}$ alkynyl group, an unsubstituted or substituted $C_{3-8}$ cycloalkyl group, an unsubstituted or substituted $C_{4-8}$ cycloalkenyl group, an unsubstituted or substituted $C_{6-10}$ aryl group, an unsubstituted or substituted heterocyclic group, an unsubstituted or substituted $C_{1-8}$ acyl group, an unsubstituted or substituted (1-imino)$C_{1-8}$ alkyl group, an unsubstituted or substituted carboxyl group, an unsubstituted or substituted carbamoyl group, an unsubstituted or substituted hydroxyl group, an unsubstituted or substituted amino group, an unsubstituted or substituted mercapto group, a substituted sulfonyl group, a halogeno group, a cyno group, or a nitro group;

n represents a number of $R^5$ and is an integer of 0 to 5;

any one of $R^1$ to $R^3$ and any one of $R^5$ may be joined to form an unsubstituted or substituted 5- to 8-membered ring;

A represents: a 5- to 7-membered hydrocarbon ring or a 5- to 7-membered heterocyclic ring when R is a group represented by $CR^1R^2R^3$; or a benzene ring when R is an unsubstituted or substituted $C_{6-10}$ aryl group or a cyano group;

D represents a 5- to 7-membered hydrocarbon ring or a 5- to 7-membered heterocyclic ring;

X represents an oxygen atom, a sulfur atom, a sulfenyl group, a sulfonyl group, an unsubstituted or substituted carbon atom, or an unsubstituted or substituted nitrogen atom;

Y represents a carbon atom or a nitrogen atom; and

Z represents a carbon atom or a nitrogen atom.

<2> A nitrogen-containing heterocyclic compound represented by Formula (II), a salt thereof, or an N-oxide compound thereof.

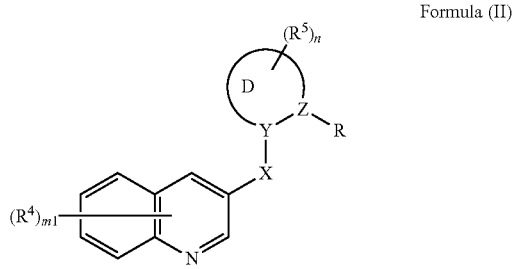

Formula (II)

In Formula (II), each of R, $R^4$, $R^5$, n, D, X, Y, and Z represents the same meaning as those in Formula (I) described above in <1>; and m1 represents a number of $R^4$ and is an integer of 0 to 6.

<3> A nitrogen-containing heterocyclic compound represented by Formula (III), a salt thereof, or an N-oxide compound thereof.

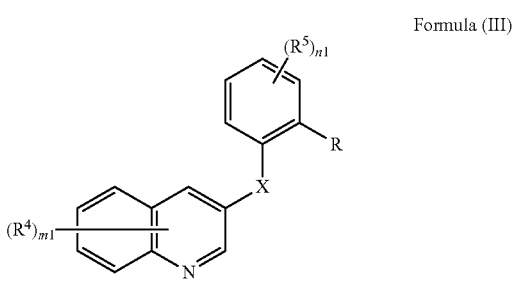

Formula (III)

In Formula (III), each of R, $R^4$, $R^5$, m1 and X represents the same meaning as those in Formula (II) described above in <2>; and n1 represents a number of $R^5$ and is an integer of 0 to 4.

<4> An agricultural fungicide comprising, as an active ingredient, at least one selected from the group consisting of the nitrogen-containing heterocyclic compound, the salt thereof, and the N-oxide compound thereof, of any one <1> to <3>.

<5> An intermediate product of the nitrogen-containing heterocyclic compound represented by Formula (I), the salt thereof, or the N-oxide compound thereof, described above in <1>, the intermediate product being selected from the group consisting of 8-fluoro-3-hydroxyquinoline, 7,8-difluoro-3-hydroxyquinoline, 7,8-difluoro-3-iodoquinoline, 8-fluoro-3-hydroxy-2-methylquinoline, and 7,8-difluoro-3-hydroxy-2-methylquinoline.

Effect of the Invention

The nitrogen-containing heterocyclic compound, the salt thereof, and N-oxide compound thereof according to the present invention are novel compounds useful as an active ingredient of an agricultural fungicide which has reliable effects and is safe to use.

The agricultural fungicide according to the present invention is an agent which has excellent control effects, does not cause phytotoxicity in plants, and has little toxicity to humans, domestic animals, and fish or on the environment.

MODES FOR CARRYING OUT THE INVENTION

Hereinafter, the present invention will be categorized into 1) a nitrogen-containing heterocyclic compound represented by Formula (I), and a salt thereof or an N-oxide compound thereof, and 2) an agricultural fungicide and will be described in detail.

1) Nitrogen-containing heterocyclic compound represented by Formula (I), and salt thereof, or N-oxide compound thereof.

The nitrogen-containing heterocyclic compound according to the present invention is represented by Formula (I) (hereinafter, sometimes referred to as "compound (I)"), is preferably represented by Formula (II) (hereinafter, sometimes referred to as "compound (II)"), and is more preferably represented by Formula (III) (hereinafter, sometimes referred to as "compound (III)").

The nitrogen-containing heterocyclic compound, the salt thereof, or the N-oxide compound thereof according to the present invention may be a hydrate, a solvate, a crystal polymorphism, or the like. Also, an asymmetric carbon atom, stereoisomers based on a double bond or the like, or a mixture thereof, may be present in the nitrogen-containing heterocyclic compound, the salt thereof, or the N-oxide compound thereof according to the present invention.

First of all, the meaning of "unsubstituted" and "substituted" in Formulae (I), (II), and (III) will be explained. The term "unsubstituted" in the present specification means that the specified group is solely formed of a group serving as a mother nucleus. When only the name of the group serving as the mother nucleus is mentioned without mention of "substituted", it means "unsubstituted" unless otherwise stated.

On the other hand, the term "substituted" means that a hydrogen atom of a group serving as a mother nucleus has been substituted with a substituent having the same structure as or a different structure to the mother nucleus. The "substituent" is a different group which is bonded to the group serving as a mother nucleus. The "substituent" may be one or more. At least two substituents may be the same or different.

Terms such as "$C_{1-6}$" or the like indicate that the number of carbon atoms in a group serving as a mother nucleus is 1 to 6 or the like. The number of carbon atoms does not include carbon atoms in a substituent. For example, a butyl group having an epoxy group as a substituent is categorized as a $C_2$ alkoxy $C_4$ alkyl group.

The "substituent" is not particularly limited as long as it is chemically acceptable and has the effects of the present invention.

Examples of the "substituent" include: a halogen atom such as a fluorine atom, a chlorine atom, a bromine atom, or an iodine atom; a $C_{1-6}$ alkyl group such as a methyl group, an ethyl group, an n-propyl group, an i-propyl group, an n-butyl group, an s-butyl group, an i-butyl group, a t-butyl group, an n-pentyl group, or an n-hexyl group; a $C_{3-6}$ cycloalkyl group such as a cyclopropyl group, a cyclobutyl group, a cyclopentyl group, or a cyclohexyl group; a $C_{2-6}$ alkenyl group such as a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, and a 5-hexenyl group; a $C_{3-6}$ cycloalkenyl group such as a 2-cyclopropenyl group, a 2-cyclopentenyl group, or a 3-cyclohexenyl group; a $C_{2-6}$ alkynyl group such as an ethynyl group, a 1-propynyl group, 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group, or a 1,1-dimethyl-2-butynyl group;

a $C_{1-6}$ alkoxy group such as a methoxy group, an ethoxy group, an n-propoxy group, an i-propoxy group, an n-butoxy group, an s-butoxy group, an i-butoxy group, or a t-butoxy group; a $C_{2-6}$ alkenyloxy group such as a vinyloxy group, an allyloxy group, a propenyloxy group, or a butenyloxy group; a $C_{2-6}$ alkynyloxy group such as an ethynyloxy group or a propargyloxy group; a $C_{6-10}$ aryl group such as a phenyl group or a naphthyl group; a $C_{6-10}$ acyloxy group such as a phenoxy group or a 1-naphthoxy group; a $C_{7-11}$ aralkyl group such as a benzyl group or a phenethyl group; a $C_{7-11}$ aralkyloxy group such as a benzyloxy group or a phenethyloxy group; a $C_{1-7}$ acyl group such as a formyl group, an acetyl group, a propionyl group, a benzoyl group, or a cyclohexylcarbonyl group; a $C_{1-7}$ acyloxy group such as a formyloxy group, an acetyloxy group, a propionyloxy group, a benzoyloxy group, or a cyclohexylcarbonyloxy group; a $C_{1-6}$ alkoxycarbonyl group such as a methoxycarbonyl group, an ethoxycarbonyl group, an n-propoxycarbonyl group, an i-propoxycarbonyl group, an n-butoxycarbonyl group, and a t-butoxycarbonyl group; carboxyl group;

a hydroxyl group; an oxo group; a $C_{1-6}$ haloalkyl group such as chloromethyl group, a chloroethyl group, a trifluoromethyl group, a 1,2-dichloro-n-propyl group, a 1-fluoro-n-butyl group, or a perfluoro-n-pentyl group; a $C_{2-6}$ haloalkenyl group such as a 2-chloro-1-propenyl group or a 2-fluoro-1-butenyl group; a $C_{2-6}$ haloalkynyl group such as a 4,4-dichloro-1-butynyl group, a 4-fluoro-1-pentynyl group or a 5-bromo-2-pentynyl group; a $C_{1-6}$ haloalkoxy group such as a 2-chloro-n-propoxy group or a 2,3-dichlorobutoxy group; a $C_{2-6}$ haloalkenyloxy group such as a 2-chloropropenyloxy group or a 3-bromobutenyloxy group; a $C_{6-10}$ haloaryl group such as a 4-chlorophenyl group, a 4-fluorophenyl group, or a 2,4-dichlorophenyl group; a $C_{6-10}$ haloaryloxy group such as a 4-fluorophenyloxy group, or a 4-chloro-1-naphthoxy group; a $C_{1-7}$ haloacyl group such as a chloroacetyl group, a trifluoroacetyl group, a trichloroacetyl group, or a 4-chlorobenzoyl group;

a cyano group; an isocyano group; a nitro group; an isocyanate group; a cyanate group; an azide group; an amino group; a $C_{1-6}$ alkylamino group such as a methylamino group, a dimethylamino group, or a diethylamino group; a $C_{6-10}$ arylamino group such as an anilino group or a naphthylamino group; a $C_{7-11}$ aralkylamino group such as a benzylamino group or a phenylethylamino group; a $C_{1-7}$ acylamino group such as a formylamino group, an acetylamino group, a propanoylamino group, a butyrylamino group, an i-propylcarbonylamino group, or a benzoylamino group; a $C_{1-6}$ alkoxycarbonylamino group such as a methoxycarbonylamino group, an ethoxycarbonylamino group, an n-propoxycarbonylamino group, or an i-propoxycarbonylamino group; a carbamoyl group; a substituted carbamoyl group such as a dimethylcarbamoyl group, a phenylcarbamoyl group, or an N-phenyl-N-methylcarbamoyl group; an imino $C_{1-6}$ alkyl group such as an iminomethyl group, a (1-imino)ethyl group, or a (1-imino)-n-propyl group; a hydroxyimino $C_{1-6}$ alkyl group such as a hydroxyiminomethyl group, a (1-hydroxyimino)ethyl group, or a (1-hydroxyimino)propyl group; a $C_{1-6}$ alkoxyimino $C_{1-6}$ alkyl group such as a methoxyiminomethyl group or a (1-methoxyimino)ethyl group;

a mercapto group; an isothiocyanate group; a thiocyanate group; a $C_{1-6}$ alkylthio group such as a methylthio group, an ethylthio group, an n-propylthio group, an i-propylthio group, an n-butylthio group, an i-butylthio group, an s-butylthio group, or a t-butylthio group; a $C_{2-6}$ alkenylthio group such as a vinylthio group or an allylthio group; a $C_{2-6}$ alkynylthio group such as an ethynylthio group or a propargylthio group; a $C_{6-10}$ arylthio group such as a phenylthio group or a naphthylthio group; a heteroarylthio group such as a thiazolylthio group or a pyridylthio group; a $C_{7-11}$ aralkylthio group such as a benzylthio group or a phenethylthio group; a ($C_{1-6}$alkylthio) carbonyl group such as a (methylthio)carbonyl group, an (ethylthio)carbonyl group, a (n-propylthio)carbonyl group, a (i-propylthio)carbonyl group, a (n-butylthio)carbonyl group, a (i-butylthio)carbonyl group, a (s-butylthio)carbonyl group, or a (t-butylthio)carbonyl group;

a $C_{1-6}$ alkylsulfinyl group such as a methylsulfinyl group, an ethylsulfinyl group, or a t-butylsulfinyl group; a $C_{2-6}$ alkenylsulfinyl group such as an allylsulfinyl group; a $C_{2-6}$ alkynylsulfinyl group such as a propargylsulfinyl group; a $C_{6-10}$ arylsulfinyl group such as a phenylsulfinyl group; a heteroarylsulfinyl group such as a thiazolylsulfinyl group or a pyridylsulfinyl group; a $C_{7-11}$ aralkylsulfinyl group such as a benzylsulfinyl group or a phenethylsulfinyl group; a $C_{1-6}$alkylsulfonyl group such as a methylsulfonyl group, an ethylsulfonyl group, or a t-butylsulfonyl group; a $C_{2-6}$ alkenylsulfonyl group such as an allylsulfonyl group; a $C_{2-6}$ alkylsulfonyl group such as a propargylsulfonyl group; a $C_{6-10}$ arylsulfonyl group such as a phenylsulfonyl group; a heteroarylsulfonyl group such as a thiazolylsulfonyl group or a pyridylsulfonyl group; a $C_{7-11}$ aralkylsulfonyl group such as a benzylsulfonyl group or a phenethylsulfonyl group;

a 5-membered heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, or a tetrazolyl group; a 6-membered heteroaryl group such as a pyridyl group, pyrazinyl group, pyrimidinyl group, a pyridazinyl group, or a triazinyl group; a saturated heterocyclic group such as an aziridinyl group, an epoxy group, a pyrrolidinyl group, a tetrahydrofuranyl group, a piperidyl group, a piperazinyl group, or a morpholinyl group; a tri $C_{1-6}$allylsilyl group such as a trimethylsilyl group, a triethylsilyl group, or a t-butyldimethylsilyl group; a triphenylsilyl group; and the like.

The "substituent" may have a different "substituent".

[R]

R represents a group represented by $CR^1R^2R^3$, an unsubstituted or substituted $C_{6-10}$ aryl group, or a cyano group.

$R^1$ to $R^3$ each independently represents a hydrogen atom, an unsubstituted or substituted $C_{1-8}$ alkyl group, an unsubstituted or substituted $C_{2-8}$ alkenyl group, an unsubstituted or substituted $C_{2-8}$ alkynyl group, an unsubstituted or substituted $C_{3-8}$ cycloalkyl group, an unsubstituted or substituted $C_{4-8}$ cycloalkenyl group, an unsubstituted or substituted $C_{6-10}$ aryl group, an unsubstituted or substituted heterocyclic group, an unsubstituted or substituted $C_{1-8}$ acyl group, an unsubstituted or substituted (1-imino) $C_{1-8}$ alkyl group, an unsubstituted or substituted carboxyl group, an unsubstituted or substituted carbamoyl group, an unsubstituted or substituted hydroxyl group, an unsubstituted or substituted amino group, an unsubstituted or substituted mercapto group, a substituted sulfonyl group, a halogeno group, a cyano group, or a nitro group.

However, there are no cases in which $R^1$ to $R^3$ are all hydrogen atoms. Also, there are no cases in which $R^1$ to $R^3$ are all unsubstituted $C_{1-8}$ alkyl groups. Also, when any one of $R^1$ to $R^3$ is a hydrogen atom, there are no cases in which the remaining two are both unsubstituted $C_{1-8}$ alkyl groups. Also, when any one of $R^1$ to $R^3$ is an unsubstituted $C_{1-8}$ alkyl group, there are no cases in which the remaining two are both hydrogen atoms.

A "$C_{1-8}$ alkyl group" is a saturated hydrocarbon having 1 to 8 carbon atoms. The $C_{1-8}$ alkyl group may be a straight chain or a branched chain. Examples of the $C_{1-8}$ alkyl group include a methyl group, an ethyl group, an n-propyl group, an n-butyl group, an n-pentyl group, an n-hexyl group, an n-heptyl group, an n-octyl group, an i-propyl group, an i-butyl group, an s-butyl group, a t-butyl group, an i-pentyl group, a neopentyl group, a 2-methylbutyl group, a 2,2-dimethylpropyl group, an i-hexyl group and the like. Among these, a $C_{1-6}$ alkyl group is preferable.

Examples of "substituted $C_{1-8}$ alkyl group" include:

a cycloalkylalkyl group such as a cyclopropylmethyl group, a 2-cyclopropylethyl group, a cyclopentylmethyl group, or a 2-cyclohexylethyl group, preferably a $C_{3-6}$cycloalkyl $C_{1-6}$ alkyl group;

a cycloalkenylalkyl group such as a cyclopentenylmethyl group, a 3-cyclopentenylmethyl group, a 3-cyclohexenylmethyl group, or a 2-(3-cyclohexenyl)ethyl group, preferably a $C_{4-8}$ cycloalkenyl $C_{1-6}$ alkyl group;

a haloalkyl group such as a fluoromethyl group, a chloromethyl group, a bromomethyl group, a difluoromethyl group, a dichloromethyl group, a dibromomethyl group, a trifluoromethyl group, a trichloromethyl group, a tribromomethyl group, a 2,2,2-trifluoroethyl group, a 2,2,2-trichloroethyl group, a pentafluoroethyl group, a 4-fluorobutyl group, a 4-chlorobutyl group, a 3,3,3-trifluoropropyl group, a 2,2,2-trifluoro-1-trifluoromethylethyl group, a perfluorohexyl group, a perchlorohexyl group, a perfluorooctyl group, a perchlorooctyl group, a 2,4,6-trichlorohexyl group, a perfluorodecyl group, or a 2,2,4,4,6,6-hexachlorooctyl group, preferably a $C_{1-6}$ haloalkyl group;

an arylalkyl group (aralkyl group) such as a benzyl group, a phenethyl group, a 3-phenylpropyl group, a 1-naphthylmethyl group, or a 2-naphthylmethyl group, preferably a $C_{6-10}$ aryl $C_{1-6}$ alkyl group;

a heteroarylalkyl group such as a 2-pyridylmethyl group, a 3-pyridylmethyl group, 4-pyridylmethyl group, a 2-(2-pyridyl)ethyl group, a 2-(3-pyridyl)ethyl group, a 2-(4-pyridyl)ethyl group, a 3-(2-pyridyl)propyl group, a 3-(3-pyridyl)propyl group, a 3-(4-pyridyl)propyl group, a 2-pyrazinylmethyl group, a 3-pyrazinylmethyl group, a 2-(2-pyrazinyl)ethyl group, a 2-(3-pyrazinyl)ethyl group, a 3-(2-pyrazinyl)propyl group, a 3-(3-pyrazinyl)propyl group, a 2-pyrimidylmethyl group, a 4-pyrimidylmethyl group, a 2-(2-pyrimidyl)ethyl group, a 2-(4-pyrimidyl)ethyl group, a 3-(2-pyrimidyl)propyl group, a 3-(4-pyrimidyl)propyl group, a 2-furylmethyl group, a 3-furylmethyl group, a 2-(2-furyl)ethyl group, a 2-(3-furyl)ethyl group, a 3-(2-furyl)propyl group, or a 3-(3-furyl)propyl group, preferably a 5- to 6-membered heteroaryl $C_{1-6}$ alkyl group;

a hydroxyalkyl group such as a hydroxymethyl group, a 1-hydroxyethyl group, a 2-hydroxyethyl group, a 1-hydroxypropyl group, a 3-hydroxypropyl group, a 1-hydroxy-1-methylethyl group, a 2-hydroxy-1,1-dimethylethyl group, a 2-hydroxy-1,1-dimethylpropyl group, or a 2-hydroxy-2-methylpropyl group, preferably a hydroxyl $C_{1-6}$ alkyl group;

an alkoxyalkyl group such as a methoxymethyl group, an ethoxymethyl group, a 2-methoxyethyl group, a 2-ethoxyethyl group, a methoxy-n-propyl group, an n-propoxymethyl group, an i-propoxyethyl group, an s-butoxymethyl group, a t-butoxyethyl group, a 2,2-dimethoxyethyl group, or a 2,2-dimethoxy-1,1-dimethylethyl group, preferably a $C_{1-6}$ alkoxy $C_{1-6}$ alkyl group;

an acyloxyalkyl group such as a formyloxymethyl group, an acetoxymethyl group, a 2-acetoxyethyl group, a propionyloxymethyl group, or a propionyloxyethyl group, preferably $C_{1-7}$ acyloxy $C_{1-6}$ alkyl group;

a trialkylsilyloxyalkyl group such as a trimethylsilyloxymethyl group or a t-butyldimethylsilyloxymethyl group, preferably a tri $C_{1-6}$ alkylsilyloxy $C_{1-6}$ alkyl group;

an arylsulfonyloxyalkyl group such as a tosyloxymethyl group or a 2-tosyloxy-1,1-dimethylethyl group, preferably a $C_{1-6}$ alkyl-substituted $C_{6-10}$ arylsulfonyloxy $C_{1-6}$ alkyl group;

a cyanoalkyl group such as a cyanomethyl group, a 2-cyanoethyl group, or a 1-cyano-1-methylethyl group, preferably a cyano $C_{1-6}$ alkyl group;

an acylalkyl group such as a formylmethyl group, a 2-formylethyl group, a 3-formylpropyl group, a 1-formyl-1-methylethyl group, a 2-formyl-1,1-dimethylethyl group, an acetylmethyl group, a 2-acetylethyl group, a 3-acetylpropyl group, 1-acetyl-1-methylethyl group, or a 2-acetyl-1,1-dimethylethyl group, preferably a $C_{1-6}$ acyl $C_{1-6}$ alkyl group;

a 2-hydroxyiminoalkyl group such as a 2-hydroxyiminoethyl group, a 2-hydroxyimino-1-methylethyl group, a 2-hydroxy-1,1-dimethylethyl group, or a 2-hydroxyiminopropyl group, preferably 2-hydroxyimino $C_{2-6}$ alkyl group;

an acylalkyl group such as an acetylmethyl group, a 2-acetylethyl group, a 3-acetylpropyl group, a 1-acetyl-1-methylethyl group, or a 2-acetyl-1,1-dimethylethyl group, preferably a formyl $C_{1-6}$ alkyl group;

a carboxyalkyl group such as a carboxymethyl group, a 2-carboxyethyl group, a 3-carboxypropyl group, a 1-carboxy-1-methylethyl group, or a 2-carboxy-1,1-dimethylethyl group, preferably a carboxy $C_{1-6}$ alkyl group;

an alkoxycarbonylalkyl group such as a methoxycarbonylmethyl group, a 2-methoxycarbonylethyl group, a 3-methoxycarbonylpropyl group, a 1-methoxycarbonyl-1-methylethyl group, or a 2-methoxycarbonyl-1,1-dimethylethyl group, preferably a $C_{1-6}$ alkoxycarbonyl $C_{1-6}$ alkyl group;

an azidoalkyl group such as an azidomethyl group, a 2-azidoethyl group, or a 1-azido-1-methylethyl group, preferably an azido $C_{1-6}$ alkyl group; and the like.

A "$C_{2-8}$ alkenyl group" is an unsaturated hydrocarbon group including 2 to 8 carbon atoms having at least one carbon-carbon double bond. The $C_{2-8}$ alkenyl group may be a straight chain or a branched chain. Examples of the $C_{2-8}$ alkenyl group include a vinyl group, a 1-propenyl group, an isopronpenyl group, an allyl group, a 1-butenyl group, a 2-butenyl group, a 3-butenyl group, a 1-pentenyl group, a 2-pentenyl group, a 3-pentenyl group, a 4-pentenyl group, a 1-hexenyl group, a 2-hexenyl group, a 3-hexenyl group, a 4-hexenyl group, a 5-hexenyl group, a 1-heptenyl group, a 6-heptenyl group, a 1-octenyl group, a 7-octenyl group, a 1-methyl-allyl group, a 2-methyl-allyl group, a 1-methyl-2-butenyl group, a 2-methyl-2-butenyl group, and the like. Among these, a $C_{2-6}$ alkenyl group is preferable.

Examples of a "substituted $C_{2-8}$ alkenyl group" include: a haloalkenyl group such as a 3-chloro-2-propenyl group, 4-chloro-2-butenyl group, a 4,4-dichloro-3-butenyl group, 4,4-difluoro-3-butenyl group, a 3,3-dichloro-2-propenyl group, a 2,3-dichloro-2-propenyl group, a 3,3-difluoro-2-propenyl group, or a 2,4,6-trichloro-2-hexenyl group, preferably $C_{2-6}$ haloalkenyl group;

a hydroxyalkenyl group such as a 3-hydroxy-1-propenyl group, a 4-hydroxy-1-butenyl group, a 1-hydroxyallyl group, or a 1-hydroxy-2-methylallyl group, preferably a hydroxy $C_{2-6}$ alkenyl group; and the like.

A "$C_{2-8}$ alkynyl group" is an unsaturated hydrocarbon group including 2 to 8 carbon atoms having at least one carbon-carbon triple bond. The $C_{2-8}$ alkynyl group may be a straight chain or a branched chain. Examples of the $C_{2-8}$ alkynyl group include an ethynyl group, a 1-propynyl group, a propargyl group, a 1-butynyl group, a 2-butynyl group, a 3-butynyl group, a 1-pentynyl group, a 2-pentynyl group, a 3-pentynyl group, a 4-pentynyl group, a 1-hexynyl group, a 1-methyl-2-propynyl group, a 2-methyl-3-butynyl group, a 1-methyl-2-butynyl group, a 2-methyl-3-pentynyl group, a 1,1-dimethyl-2-butynyl group, and the like. Among these, a $C_{2-6}$ alkynyl group is preferable.

Examples of a "substituted $C_{2-8}$ alkynyl group" include a haloalkynyl group such as a 3-chloro-1-propynyl group, a 3-chloro-1-butynyl group, a 3-bromo-1-butynyl group, a 3-bromo-2-propynyl group, a 3-iodo-2-propynyl group, a 3-bromo-1-hexynyl group, a 4,4,6,6-tetrafluoro-1-dodecynyl group, a 5,5-dichloro-2-methyl-3-pentynyl group, or a 4-chloro-1,1-dimethyl-2-butynyl group, preferably a $C_{2-6}$ haloalkynyl group, and the like.

A "$C_{3-8}$ cycloalkyl group" is an alkyl group including 3 to 8 carbon atoms having a cyclic moiety. Examples of the $C_{3-8}$ cycloalkyl group include a cyclopropyl group, a cyclobutyl group, a cyclopentyl group, a cyclohexyl group, a cycloheptyl group, a cyclooctyl group, and the like. Among these, a $C_{3-6}$ cycloalkyl group is preferable.

Examples of a "substituted $C_{3-8}$ cycloalkyl group" include an alkyl-substituted cycloalkyl group such as a 2,3,3-trimethylcyclobutyl group, a 4,4,6,6-tetramethylcyclohexyl group, or a 1,3-dibutylcyclohexyl group, preferably a $C_{3-6}$ cycloalkyl group in which 1 to 3 $C_{1-6}$ alkyl group(s) is(are) substituted, and the like.

A "$C_{4-8}$ cycloalkenyl group" is an alkenyl group including 4 to 8 carbon atoms having a cyclic moiety. Examples of the $C_{4-8}$ cycloalkenyl group include a 1-cyclobutenyl group, a 1-cyclopentenyl group, a 3-cyclopentenyl group, a 1-cyclohexenyl group, a 3-cyclohexenyl group, a 3-cycloheptenyl group, a 4-cyclooctenyl group, and the like.

Examples of a "substituted $C_{4-8}$ cycloalkenyl group" include an alkyl-substituted cycloalkenyl group such as a 2-methyl-3-cyclohexenyl group or a 3,4-dimethyl-3-cyclohexenyl group, preferably a $C_{4-6}$ cycloalkenyl group in which 1 to 3 $C_{1-6}$ alkyl group(s) is(are) substituted, and the like.

A "$C_{6-10}$ aryl group" is a monocyclic or polycyclic aryl group having 6 to 10 carbon atoms. In the polycyclic aryl group, if at least one ring is an aromatic ring, the remaining ring(s) may be any of a saturated alicyclic ring, an unsaturated alicyclic ring, and an aromatic ring. Examples of the $C_{6-10}$ aryl group include a phenyl group, a naphthyl group, an azulenyl group, an indenyl group, an indanyl group, a tetralinyl group, and the like. Among these, a phenyl group is preferable.

Examples of a "substituted $C_{6-10}$ aryl group" include an alkyl-substituted aryl group such as a 2-chlorophenyl group, a 3,5-dichlorophenyl group, a 4-fluorophenyl group, a 3,5-difluorophenyl group, a 4-trifluoromethylphenyl group, or a 2-methoxy-1-naphthyl group, a halogeno-substituted aryl group, and an alkoxy-substituted aryl group, preferably a $C_{1-6}$ alkyl-substituted $C_{6-10}$ aryl group, a halogeno-substituted $C_{6-10}$ aryl group, and a $C_{1-6}$ alkoxy substituted aryl group.

A "heterocyclic group" includes 1 to 4 heteroatom(s) selected from the group consisting of a nitrogen atom, an oxygen atom, and a sulfur atom, as a constituent atom of a ring. The heterocyclic group may be monocyclic or polycyclic.

Examples of the heterocyclic group include a 5-membered heteroaryl group, a 6-membered heteroaryl group, a condensed heteroaryl group, a saturated heterocyclic group, a partially unsaturated heterocyclic group and the like.

Examples of the 5-membered heteroaryl group include: a pyrrolyl group such as a pyrrol-1-yl group, a pyrrol-2-yl group, or a pyrrol-3-yl group; a furyl group such as a furan-2-yl group or a furan-3-yl group; a thienyl group such as a thiophen-2-yl group, or a thiophen-3-yl group; an imidazolyl group such as an imidazol-1-yl group, an imidazol-2-yl group, an imidazol-4-yl group, or an imidazol-5-yl group; a pyrazolyl group such as a pyrazol-1-yl group, a pyrazol-3-yl group, a pyrazol-4-yl group, or a pyrazol-5-yl group; an oxazolyl group such as an oxazol-2-yl group, an oxazol-4-yl group, or an oxazol-5-yl group; an isoxazolyl group such as an isoxazol-3-yl group, an isoxazol-4-yl group, or an isoxazol-5-yl group; a thiazolyl group such as a thiazol-2-yl group, a thiazol-4-yl group, or a thiazol-5-yl group; an isothiazolyl group such as an isothiazol-3-yl group, an isothiazol-4-yl group, or a thiazol-5-yl group; a triazolyl group such as a 1,2,3-triazol-1-yl group, a 1,2,3-triazol-4-yl group, a 1,2,3-triazol-5-yl group, a 1,2,4-triazol-1-yl group, a 1,2,4-triazol-3-yl group, or a 1,2,4-triazol-5-yl group; an oxadiazolyl group such as a 1,2,4-oxadiazol-3-yl group, a 1,2,4-oxadiazol-5-yl group, or a 1,3,4-oxadiazol-2-yl group; a thiadiazolyl group such as a 1,2,4-thiadiazol-3-yl group, 1,2,4-thiadiazol-5-yl group, or a 1,3,4-thiadiazol-2-yl group; a tetrazolyl group such as a tetrazol-1-yl group or a tetrazol-2-yl group; and the like.

Examples of the 6-membered heteroaryl group include: a pyridyl group such as a pyridin-2-yl group, a pyridin-3-yl group, or a pyridin-4-yl group; a pyrazinyl group such as a pyrazin-2-yl group or a pyrazin-3-yl group; a pyrimidinyl group such as a pyrimidin-2-yl group, a pyrimidin-4-yl group, or a pyrimidin-5-yl group; a pyridazinyl group such a pyridazin-3-yl group or a pyridazin-4-yl group; a triazinyl group; and the like.

Examples of the condensed heteroaryl group include: indol-1-yl group, an indol-2-yl group, an indol-3-yl group, an indol-4-yl group, an indol-5-yl group, an indol-6-yl group, an indol-7-yl group; a benzofuran-2-yl group, a benzofuran-3-yl group, a benzofuran-4-yl group, a benzofuran-5-yl group, a benzofuran-6-yl group, a benzofuran-7-yl group; a benzothiophen-2-yl group, a benzothiophen-3-yl group, a benzothiophen-4-yl group, a benzothiophen-5-yl group, a benzothiophen-6-yl group, a benzothiophen-7-yl group; a benzoimidazol-1-yl group, a benzoimidazol-2-yl group, a benzoimidazol-4-yl group, a benzoimidazol-5-yl group, a benzoxazol-2-yl group, a benzoxazol-4-yl group, a benzoxazol-5-yl group, a benzothiazol-2-yl group, a benzothiazol-4-yl group, a benzothiazol-5-yl group; a quinolin-2-yl group, a quinolin-3-yl group, a quinolin-4-yl group, a quinolin-5-yl group, a quinolin-6-yl group, a quinolin-7-yl group, a quinolin-8-yl group; and the like.

Examples of the other heterocyclic group include: a 3-membered saturated heterocyclic ring such as an aziridin-1-yl group, an aziridin-2-yl group, or an oxiranyl group; a 5-membered saturated heterocyclic ring such as a pyrrolidin-1-yl group, a pyrrolidin-2-yl group, a pyrrolidin-3-yl group, a tetrahydrofuran-2-yl group, a tetrahydrofuran-3-yl group, or a [1,3]dioxiran-2-yl group; a 6-membered saturated heterocyclic ring such as a piperidin-1-yl group, a piperidin-2-yl group, a piperidin-3-yl group, a piperidin-4-yl group, a piperazin-1-yl group, a piperazin-2-yl group, a morpholin-2-yl group, a morpholin-3-yl group, or a morpholin-4-yl group; a 1,3-benzodioxol-4-yl group, a 1,3-benzodioxol-5-yl group, a 1,4-benzodioxan-5-yl group, a 1,4-benzodioxan-6-yl group, a 3,4-dihydro-2H-1,5-benzodioxepin-6-yl group, a 3,4-dihydro-2H-1,5-benzodioxepin-7-yl group, a 2,3-dihydrobenzofuran-4-yl group, a 2,3-dihydrobenzofuran-5-yl group, a 2,3-dihydrobenzofuran-6-yl group, or a 2,3-dihydrobenzofuran-7-yl group; and the like.

Examples of a "substituted heterocyclic group" include: a 4-chloro-2-pyridinyl group, a 3-chloro-2-pyrazinyl group, a 4-methyl-2-pyridinyl group, a 5-trifluoromethyl-2-pyrimidinyl group, a 3-methyl-2-quinolyl group, and the like.

A "$C_{1-8}$ acyl group" is a group in which a hydrogen atom, a $C_{1-7}$ alkyl group, a $C_{2-7}$ alkenyl group, a $C_{2-7}$ alkynyl group, a $C_{6-7}$ aryl group, or a 5- to 7-membered heterocyclic group is bonded to a carbonyl group.

Examples of the $C_{1-8}$ acyl group include: a formyl group; an alkylcarbonyl group such as an acetyl group, a propionyl group, an n-propylcarbonyl group, an n-butylcarbonyl group, a pentanoyl group, a valeryl group, an octanoyl group, an i-propylcarbonyl group, an i-butylcarbonyl group, a pivaloyl group, or an isovaleryl group, preferably a $C_{1-6}$ alkylcarbonyl group; an alkenylcarbonyl group such as an acryloyl group, or a metacryloyl group, preferably a $C_{2-6}$ alkenylcarbonyl group; an alkynylcarbonyl group such as a propioloyl group, preferably a $C_{2-6}$ alkynylcarbonyl group; an arylcarbonyl group such as a benzoyl group; a heterocyclic carbonyl group such as a 2-pyridylcarbonyl group or a thienylcarbonyl group; and the like.

Examples of a "substituted $C_{1-3}$ acyl group" include: a haloacyl group such as a monofluoroacetyl group, a monochloroacetyl group, a monobromoacetyl group, a difluoroacetyl group, a dichloroacetyl group, a dibromoacetyl group, a trifluoroacetyl group, a trichloroacetyl group, a tribromoacetyl group, a 3,3,3-trifluoropropionyl group, a 3,3,3-trichloropropionyl group, or a 2,2,3,3,3-pentafluoropropionyl group, preferably a $C_{1-7}$ haloacyl group; and the like.

A "(1-imino)$C_{1-8}$ alkyl group" is an iminomethyl group or a group in which a $C_{1-7}$ alkyl group is bonded to an iminomethyl group. Examples of the (1-imino)$C_{1-8}$ alkyl group include an iminomethyl group, a (1-imino)ethyl group, a (1-imino)propyl group, a (1-imino)butyl group, a (1-imino)pentyl group, a (1-imino)hexyl group, a (1-imino)heptyl group, and the like. Among these, a (1-imino)$C_{1-6}$ alkyl group is preferable.

Examples of a "substituted (1-imino)$C_{1-8}$ alkyl group" include: a (1-hydroxyimino)alkyl group such as a hydroxyiminomethyl group, a (1-hydroxyimino)ethyl group, a (1-hydroxyimino)propyl group, or a (1-hydroxyimino)butyl group, preferably a (1-hydroxyimino)$C_{1-6}$ alkyl group; a (1-alkoxyimino)alkyl group such as a methoxyiminomethyl group, a (1-ethoxyimino)methyl group, a (1-methoxyimino)ethyl group, a (1-t-butoxyimino)ethyl group, or a (1-ethoxyimino)ethyl group, preferably a (1-($C_{1-6}$ alkoxy)imino)$C_{1-6}$ alkyl group; and the like.

A "substituted carboxyl group" is a group in which a $C_{1-6}$ alkyl group, a $C_{2-6}$ alkenyl group, a $C_{2-6}$ alkynyl group, a $C_{6-10}$ aryl group, a $C_{6-10}$ aryl $C_{1-6}$ alkyl group, or a 5 to 6-membered heterocyclic group is bonded to a carbonyl group.

Examples of the "substituted carboxyl group" include: an alkoxycarbonyl group such as a methoxycarbonyl group, an ethoxycarbonyl group, an n-propoxycarbonyl group, an i-propoxycarbonyl group, an n-butoxycarbonyl group, an i-butoxycarbonyl group, a t-butoxycarbonyl group, an n-pentyloxycarbonyl group, or an n-hexyloxycarbonyl group, preferably a $C_{1-6}$ alkoxycarbonyl group;

an alkenyloxycarbonyl group such as a vinyloxycarbonyl group or an allyloxycarbonyl group, preferably a $C_{2-6}$ alkenyloxycarbonyl group;

an alkynyloxycarbonyl group such as an ethynyloxycarbonyl group or a propargyloxycarbonyl group, preferably a $C_{2-6}$ alkynyloxycarbonyl group;

an aryloxycarbonyl group such as a phenoxycarbonyl group or a naphthoxycarbonyl group, preferably a $C_{6-10}$ aryloxycarbonyl group;

an aralkyloxycarbonyl group such as a benzyloxycarbonyl group, preferably a $C_{6-10}$ aryl $C_{1-6}$ alkoxycarbonyl group; and the like.

A "substituted carbamoyl group" is a group in which a $C_{1-6}$ alkyl group, a $C_{2-6}$ alkenyl group, a $C_{2-6}$ alkynyl group, a $C_{6-10}$ aryl group, a $C_{6-10}$ aryl $C_{1-6}$ alkyl group, or a 5 to 6-membered heterocyclic group is bonded to a carbamoyl group.

Examples of the "substituted carbamoyl group" include: a monoalkylcarbamoyl group or a dialkylcarbamoyl group, such as a methylcarbamoyl group, an ethylcarbamoyl group, a dimethylcarbamoyl group, or a diethylcarbamoyl group, preferably a mono $C_{1-6}$ alkylcarbamoyl group or a di $C_{1-6}$ alkylcarbamoyl group; a monoarylcarbamoyl group such as a phenylcarbamoyl group or a 4-methylphenylcarbamoyl group, preferably a mono $C_{6-10}$ arylcarbamoyl group; and the like.

Examples of a "substituted hydroxyl group" include: an alkoxy group such as a methoxy group, an ethoxy group, an n-propoxy group, an n-butoxy group, an n-pentyloxy group, an n-hexyloxy group, a decyloxy group, a dodecyloxy group, a lauryloxy group, an i-propoxy group, an i-butoxy group, an s-butoxy group, a t-butoxy group, a 1-ethylpropoxy group, an i-hexyloxy group, a 4-methylpentoxy group, a 3-methylpentoxy group, a 2-methylpentoxy group, a 1-methylpentoxy group, a 3,3-dimethylbutoxy group, a 2,2-dimethylbutoxy group, a 1,1-dimethylbutoxy group, a 1,2-dimethylbutoxy group, a 1,3-dimethylbutoxy group, a 2,3-dimethylbutoxy group, a 1-ethylbutoxy group, or a 2-ethylbutoxy group, preferably a $C_{1-6}$ alkoxy group;

a cycloalkylalkoxy group such as a cyclopropylmethyloxy group or a 2-cyclopentylethyloxy group, preferably a $C_{3-8}$ cycloalkyl $C_{1-6}$ alkoxy group; an aralkyloxy group such as a benzyloxy group, preferably a $C_{6-10}$ aryl $C_{1-6}$ alkoxy group; a haloalkoxy group such as a chloromethoxy group, a dichloromethoxy group, a trichloromethoxy group, a trifluoromethoxy group, a 1-fluoroethoxy group, a 1,1-difluoroethoxy group, a 2,2,2-trifluoroethoxy group, or a pentafluoroethoxy group, preferably a $C_{1-6}$ haloalkoxy group; an alkenyloxy group such as a vinyloxy group, a 1-propenyloxy group, an allyloxy group, a 1-butenyloxy group, a 2-butenyloxy group, a 3-butenyloxy group, a 1-pentenyloxy group, a 2-pentenyloxy group, a 3-pentenyloxy group, a 4-pentenyloxy group, a 1-hexenyloxy group, a 2-hexenyloxy group, a 3-hexenyloxy group, a 4-hexenyloxy group, a 5-hexenyloxy group, a 1-methyl-2-propenyloxy group, a 2-methyl-2-propenyloxy group, a 1-methyl-2-butenyloxy group, or a 2-methyl-2-butenyloxy group, preferably a $C_{2-6}$ alkenyloxy group;

an alkynyloxy group such as an ethynyloxy group, a propynyloxy group, a propargyloxy group, a 1-butynyloxy group, a 2-butynyloxy group, a 3-butynyloxy group, a 1-pentynyloxy group, a 2-pentynyloxy group, a 3-pentynyloxy group, a 4-pentynyloxy group, a 1-hexynyloxy group, a 1-methyl-2-propynyloxy group, a 2-methyl-3-butynyloxy group, a 1-methyl-2-butynyloxy group, a 2-methyl-3-pentynyloxy group, or a 1,1-dimethyl-2-butynyloxy group, preferably a $C_{2-6}$ alkynyloxy group; a cycloalkyloxy group such as a cyclopropyloxy group, a cyclobutyloxy group, a cyclopentyloxy group, a cyclohexyloxy group, a cycloheptyloxy group, a cyclooctyloxy group, a 2-methylcyclopropyloxy group, a 2-ethylcyclopropyloxy group, a 2,3,3-trimethylcyclobutyloxy group, a 2-methylcyclopentyloxy group, a 2-ethylcyclohexyloxy group, a 2-ethylcyclooctyloxy group, a 4,4,6,6-tetramethylcyclohexyloxy group, or a 1,3-dibutylcyclohexyloxy group, preferably a $C_{3-6}$ cycloalkyloxy group; an aryloxy group such as a phenyloxy group, a naphthyloxy group, an azulenyloxy group, an indenyloxy group, an indanyloxy group, or a tetralinyloxy group, preferably a $C_{6-10}$ aryloxy group;

an arylalkyloxy group (aralkyloxy group) such as a benzyloxy group, a phenethyloxy group, or a 2-naphthylmethyloxy group, preferably a $C_{6-10}$ aryl $C_{1-6}$ alkyloxy group;

an acyloxy group such as an acetyloxy group, a propionyloxy group, an n-propylcarbonyloxy group, an i-propylcarbonyloxy group, an n-butylcarbonyloxy group, an i-butylcarbonyloxy group, a pentanoyloxy group, or a pivaloyloxy group, preferably a $C_{1-7}$ acyloxy group;

an alkoxycarbonylalkyloxy group such as a methoxycarbonylmethyloxy group or a 1-methoxycarbonyl-1-methylethyloxy group, preferably a $C_{1-6}$ alkoxycarbonyl $C_{1-6}$ alkoxy group;

a trialkylsilyloxy group such as a trimethylsilyloxy group or a t-butyldimethylsilyloxy group, preferably a tri alkylsilyloxy group;

and the like.

Examples of a "substituted amino group" include: an alkylamino group such as a methylamino group, an ethylamino group, an n-propylamino group, an n-butylamino group, a dimethylamino group, or a diethylamino group, preferably a mono $C_{1-6}$ alkylamino group or a di $C_{1-6}$ alkylamino group; a mono $C_{1-6}$ alkylideneamino group such as a methylideneamino group, or an ethylideneamino group; a monoarylamino group such as a phenylamino group or a 4-methylphenylamino group, preferably a mono $C_{6-10}$ arylamino group; a diarylamino group such as a di-1-naphthylamino group, preferably a di $C_{6-10}$ arylamino group; an aralkylamino group such as a benzylamino group, preferably a $C_{6-10}$ aryl $C_{1-6}$ alkylamino group; an acylamino group such as an acetylamino group, a trifluoroacetylamino group, or a benzoylamino group, preferably a $C_{1-6}$ acylamino group; an alkoxycarbonylamino group such as a methoxycarbonylamino group or a t-butoxycarbonylamino group, preferably a $C_{1-6}$ alkoxycarbonylamino group; and the like.

Examples of a "substituted mercapto group" include: an alkylthio group such as a methylthio group or an ethylthio group, preferably a $C_{1-6}$ alkylthio group; an arylthio group such as a phenylthio group or a 4-methylphenylthio group, preferably a $C_{6-10}$ arylthio group; an acylthio group such as an acetylthio group or a benzoylthio group, preferably a $C_{1-6}$ acylthio group; and the like.

Examples of a "substituted sulfonyl group" include: an alkylsulfonyl group such as a methylsulfonyl group, an ethylsulfonyl group, an n-propylsulfonyl group, an i-propylsulfonyl group, an n-butylsulfonyl group, an i-butylsulfonyl group, an s-butylsulfonyl group, a t-butylsulfonyl group, an n-pentylsulfonyl group, an i-pentylsulfonyl group, a neopentylsulfonyl group, a 1-ethylpropylsulfonyl group, an n-hexylsulfonyl group, or an i-hexylsulfonyl group, preferably a $C_{1-6}$ alkylsulfonyl group; a haloalkylsulfonyl group such as a trifluoromethylsulfonyl group, preferably a $C_{1-6}$ haloalkylsulfonyl group; an arylsulfonyl group such as a phenylsulfonyl group or a 4-methylphenylsulfonyl group, preferably a $C_{6-10}$ arylsulfonyl group; a sulfo group; an alkoxysulfonyl group such as a methoxysulfonyl group or an ethoxysulfonyl group, preferably a $C_{1-6}$ alkoxysulfonyl group; a sulfamoyl group; a sulfamoyl group such as an N-methylsulfamoyl group, an N-ethylsulfamoyl group, a N,N-dimethylsulfamoyl group, or an N,N-diethylsulfamoyl group, preferably a mono $C_{1-6}$ alkylsulfamoyl group or a di $C_{1-6}$ alkylsulfamoyl group; a monoarylsulfamoyl group such as a phenylsulfamoyl group or a 4-methylsulfamoyl group, preferably a mono $C_{6-10}$ arylsulfamoyl group; and the like.

Examples of a "halogeno group" include a fluorine atom, a chlorine atom, a bromine atom, an iodine atom, and the like.

As a preferred combination of a group represented by $CR^1R^2R^3$, the following combination may be included.

$R^1$ is an unsubstituted or substituted hydroxyl group;

$R^2$ is a hydrogen atom or an unsubstituted or substituted $C_{1-8}$ alkyl group; and $R^3$ is a hydrogen atom, an unsubstituted or substituted $C_{1-8}$ alkyl group, an unsubstituted or substituted $C_{2-8}$ alkenyl group, an unsubstituted or substituted $C_{2-8}$ alkynyl group, an unsubstituted or substituted $C_{3-5}$ cycloalkyl group, an unsubstituted or substituted $C_{6-10}$ aryl group, an unsubstituted or substituted heterocyclic group, an unsubstituted or substituted $C_{1-8}$ acyl group, an unsubstituted or substituted (1-imino)$C_{1-8}$ alkyl group, an unsubstituted or substituted $C_{1-8}$ alkoxycarbonyl group, an unsubstituted or substituted hydroxyl group, or a cyano group.

The following combination may also be included as a preferred example.

$R^1$ is an unsubstituted or substituted $C_{1-8}$ alkyl group;

$R^2$ is an unsubstituted or substituted $C_{1-8}$ alkyl group; and $R^3$ is a substituted $C_{1-8}$ alkyl group, an unsubstituted or substituted $C_{2-8}$ alkenyl group, an unsubstituted or substituted $C_{2-8}$ alkynyl group, an unsubstituted or substituted $C_{3-8}$ cycloalkyl group, an unsubstituted or substituted $C_{6-10}$ aryl group, an unsubstituted or substituted heterocyclic group, an unsubstituted or substituted $C_{1-8}$ acyl group, an unsubstituted or substituted (1-imino)$C_{1-8}$ alkyl group, an unsubstituted or substituted C$_{1-8}$ alkoxycarbonyl group, an unsubstituted or substituted carbamoyl group, an unsubstituted or substituted sulfonyl group, or a cyano group.

R$^1$ and R$^2$ may be joined to form an unsubstituted or substituted 5- to 8-membered ring, or to form O=, R$^a$R$^b$C=, or R'N=.

Here, R$^a$ represents a hydrogen atom or an unsubstituted or substituted C$_{1-8}$ alkyl group. R$^b$ represents a hydrogen atom or an unsubstituted or substituted C$_{1-8}$ alkyl group. R' represents an unsubstituted or substituted hydroxyl group, or an unsubstituted or substituted C$_{1-8}$ alkyl group.

The unsubstituted or substituted C$_{1-8}$ alkyl group in R$^a$, R$^b$, and R' may be the same as the "C$_{1-8}$ alkyl group" given as the examples in R$^1$ to R$^3$ above.

The substituted hydroxyl group in R' may be the same as the "substituted hydroxyl group" given as the examples in R$^1$ to R$^3$ above.

Examples of the unsubstituted or substituted 5- to 8-membered ring, which may be formed from R$^1$ and R$^2$ being joined, include: an aliphatic hydrocarbon ring such as a cyclopropane ring, a cyclobutane ring, a cyclopentane ring, a cyclohexane ring, a cycloheptane ring, or a cyclooctane ring, preferably a C$_{3-8}$ cycloalkane ring; an unsaturated heterocyclic ring such as an oxirane ring, a [1,3]dioxirane ring, a dihydro-2H-pyran ring, a dihydro-2H-thiopyran ring, and a tetrahydropyridine ring, preferably an oxygen-containing 3- to 5-membered unsaturated heterocyclic ring.

The unsubstituted or substituted C$_{6-10}$ aryl group in R may be the same as the "C$_{6-10}$ aryl group" given as the examples in R$^1$ to R$^3$ above. It is preferably a phenyl group.

[R$^4$]

R$^4$ each independently represents an unsubstituted or substituted C$_{1-8}$ alkyl group, an unsubstituted or substituted C$_{2-8}$ alkenyl group, an unsubstituted or substituted C$_{2-8}$ alkynyl group, an unsubstituted or substituted C$_{3-8}$ cycloalkyl group, an unsubstituted or substituted C$_{4-8}$ cycloalkenyl group, an unsubstituted or substituted C$_{6-10}$ aryl group, an unsubstituted or substituted heterocyclic group, an unsubstituted or substituted C$_{1-8}$ acyl group, an unsubstituted or substituted (1-imino)C$_{1-8}$ alkyl group, an unsubstituted or substituted carboxyl group, an unsubstituted or substituted carbamoyl group, an unsubstituted or substituted hydroxyl group, an unsubstituted or substituted amino group, an unsubstituted or substituted mercapto group, a substituted sulfonyl group, a halogeno group, a cyano group, or a nitro group.

The groups represented by R$^4$ may be the same as the examples given in the groups represented by R$^1$ to R$^3$.

In Formulae (I), (II) and (III), m and m1 represent the number of R$^4$ and are an integer of 0 to 6.

R$^4$ preferably represents a C$_{1-6}$ alkyl group, a C$_{1-6}$ haloalkyl group, a C$_{2-6}$ alkenyl group, a C$_{3-8}$ cycloalkyl group, a hydroxyl group, a C$_{1-6}$ alkoxy group, or a halogen group.

[R$^5$]

R$^5$ each independently represents an unsubstituted or substituted C$_{1-8}$ alkyl group, an unsubstituted or substituted C$_{2-8}$ alkenyl group, an unsubstituted or substituted C$_{2-8}$ alkynyl group, an unsubstituted or substituted C$_{3-8}$ cycloalkyl group, an unsubstituted or substituted C$_{4-8}$ cycloalkenyl group, an unsubstituted or substituted C$_{6-10}$ aryl group, an unsubstituted or substituted heterocyclic group, an unsubstituted or substituted C$_{1-8}$ acyl group, an unsubstituted or substituted (1-imino)C$_{1-8}$ allyl group, an unsubstituted or substituted carboxyl group, an unsubstituted or substituted carbamoyl group, an unsubstituted or substituted hydroxyl group, an unsubstituted or substituted amino group, an unsubstituted or substituted mercapto group, a substituted sulfonyl, a halogeno group, a cyano group, or a nitro group.

The groups represented by R$^5$ may be the same as the examples given in the groups represented by R$^1$ to R$^3$.

In Formula (I) and (II), n represents the number of R$^5$ and is an integer of 0 to 5. In Formula (III), n1 represents the number of R$^5$ and is an integer of 0 to 4.

R$^5$ preferably represents a C$_{1-6}$ alkyl group, a C$_{1-6}$ haloalkyl group, a C$_{6-10}$ aryl C$_{1-6}$ alkyl group, a C$_{3-8}$ cycloalkyl group, a C$_{6-10}$-aryl group, a C$_{1-7}$ acyl group, a C$_{1-6}$ alkoxycarbonyl group, a C$_{1-6}$ alkoxy group, an amino group, a mono C$_{1-6}$ allylamino group, di C$_{1-6}$ allylamino group, a C$_{1-6}$ alkoxycarbonylamino group, a C$_{1-6}$ alkylthio group, a C$_{1-6}$ alkylsulfonyl group, a halogeno group, a cyano group or a nitro group.

Any one of R$^1$ to R$^3$ and any one of R$^5$, by being joined, may form an unsubstituted or substituted 5- to 8-membered ring.

Examples of the 5- to 8-membered ring include: an aromatic hydrocarbon ring such as a benzene ring; a C$_{5-8}$ cycloalkene ring such as a cyclopentene ring, a cyclopentadiene ring, a cyclohexene ring, a cycloheptene ring, or a cyclooctene ring; and the like.

[A, D]

When R is a group represented by CR$^1$R$^2$R$^3$, A represents a 5- to 7-membered hydrocarbon ring or a 5- to 7-membered heterocyclic ring.

Examples of the 5- to 7-membered hydrocarbon ring include: an aromatic hydrocarbon ring such as a benzene ring; a C$_{5-7}$ cycloalkene ring such as a cyclopentene ring, a cyclohexene ring, a cycloheptene ring; an aromatic 5- to 7-membered heterocyclic ring such as a furan ring, a thiophene ring, a pyrrole ring, an imidazole ring, a pyrazole ring, a thiazole ring, an oxazole ring, an isoxazole ring, a pyridine ring, a pyrazine ring, a pyrimidine ring, a pyridazine ring, an azepine ring, or a diazepine ring; an unsaturated 5- to 7-membered heterocyclic ring such as a dihydro-2H-pyran ring, a dihydro-2H-thiopyran ring, or a tetrahydropyridine ring; and the like. Among these, an aromatic hydrocarbon ring is preferable and a benzene ring is more preferable.

When R is an unsubstituted or substituted C$_{6-10}$ aryl group or a cyano group, A represents a benzene ring.

That is, it is preferable that the compound according to the present invention be a compound (II) or (III).

D represents a 5- to 7-membered hydrocarbon ring or a 5- to 7-membered heterocyclic ring. Examples of the 5- to 7-membered hydrocarbon ring and the 5- to 7-membered heterocyclic ring include the same as the examples given above as A, and among these, an aromatic hydrocarbon ring is preferable and a benzene ring is more preferable.

That is, it is more preferable that the compound according to the present invention be a compound (III).

[X, Y, Z]

X represents an oxygen atom, a sulfur atom, a sulfenyl group, a sulfonyl group, an unsubstituted or substituted carbon atom, or an unsubstituted or substituted nitrogen atom.

Examples of a substituent of the carbon atom include an oxo group, a C$_{2-6}$ alkenylamino group, and a hydroxyl group.

Y represents a carbon atom or a nitrogen atom. Z represents a carbon atom or a nitrogen atom. It is preferable that Y and Z be both carbon atoms, and D be an aromatic ring which includes both Y and Z.

A salt or an N-oxide compound according to the present invention is not particularly limited as long as it is an agriculturally acceptable salt or N-oxide compound. Examples of the salt include: a salt of an inorganic acid such as hydrochloric acid or sulfuric acid; a salt of an organic acid such as acetic acid or lactic acid; a salt of an alkali metal such as lithium, sodium, or potassium; a salt of an alkali earth metal such as calcium or magnesium; a salt of a transition metal such as iron or copper; a salt of an organic base such as ammonia, triethylamine, tributylamine, pyridine, or hydrazine; and the like.

(Production of the Compound According to the Present Invention)

The compound according to the present invention may be produced in accordance with the following synthesis methods.

(Synthesis Method 1)

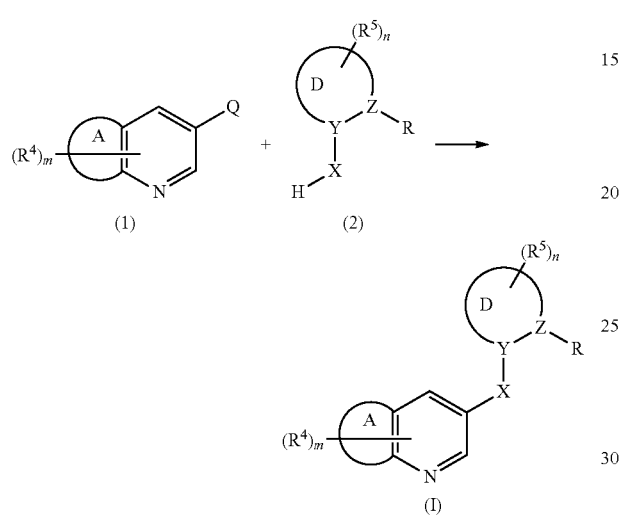

(In the formulae, R, $R^4$, $R^5$, A, D, X, Y, Z, m and n represent the same meaning as those described above. Q represents a halogen atom.)

The compound represented by Formula (I) may be produced by reacting a compound represented by Formula (1) and a compound represented by Formula (2) by conventional methods.

According to the present invention, 7,8-diflouoro-3-iodoquinoline is a useful intermediate product.

(Synthesis Method 2)

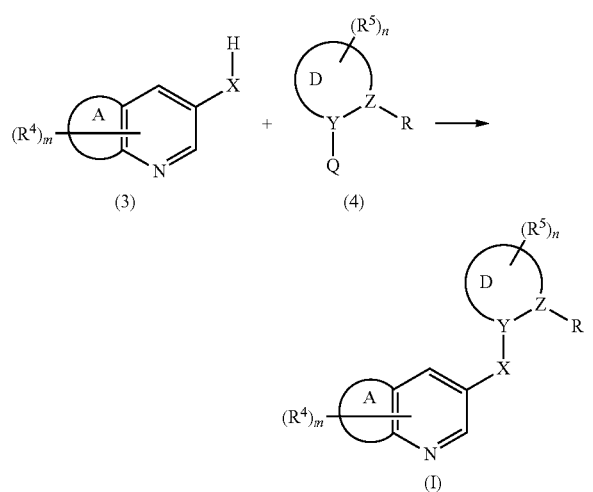

(In the formulae, R, $R^4$, $R^5$, A, D, Q, X, Y, Z, m and n represent the same meaning as those described above.)

The compound represented by Formula (I) may be produced by reacting a compound represented by Formula (3) and a compound represented by Formula (4) by conventional methods.

According to the present invention, 8-flouoro-3-hydroxyquinoline, 7,8-diflouoro-3-hydroxyquinoline, 8-flouoro-3-hydroxy-2-methylquinoline, or 7,8-diflouoro-3-hydroxy-2-methylquinoline is a useful intermediate product.

(Synthesis Method 3)

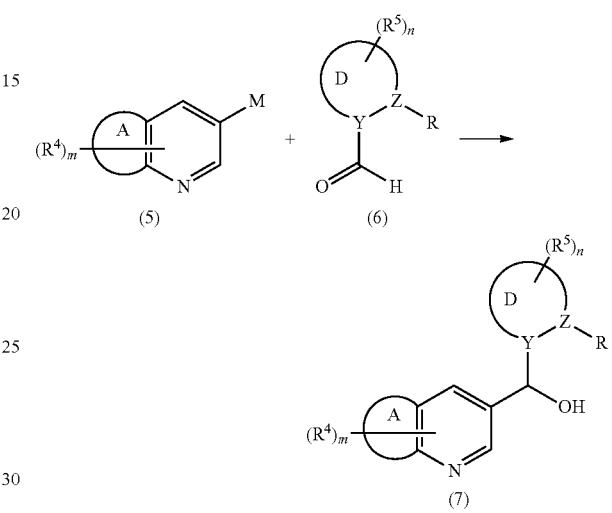

(In the formulae, R, $R^4$, $R^5$, A, D, X, Y, Z, m and n represent the same meaning as those described above. M represents lithium or magnesium.)

A compound represented by Formula (5) is obtained by lithiation or magnesium complexation using an alkyllithium reagent or a Grignard reagent or a manufactured complex prepared from an allyllithium reagent or a Grignard reagent, and then a compound represented by Formula (6) is added thereto, resulting in the production of a compound represented by Formula (7).

Examples of the alkyllithium reagent used in the lithiation include methyllithium, n-butyllithium, s-butyllithium, t-butyllithium, and the like.

Examples of the Grignard reagent used in the magnesium complexation include methylmagnesium chloride, ethylmagnesium chloride, n-butylmagnesium chloride, i-propylmagnesium chloride, and the like. Also, for example, a manufactured complex prepared from n-butylmagnesium chloride and n-butyllithium may be used.

A solvent used in the lithiation or magnesium complexation is not particularly limited as long as it forms an anhydrous reaction system without dissolving the compound to react therewith or exhibit any particular interaction therewith. Suitable examples thereof include: an alkane-based solvent such as pentane, hexane, heptane, ISOPAR (registered trademark) E, or ISOPAR (registered trademark) G; an aromatic-based solvent such as benzene, toluene, or ortho-xylene; an ether-based solvent such as diethyl ether or tetrahydrofuran; and a mixture thereof. Among these, an ether-based solvent such as diethyl ether or tetrahydrofuran is preferable. The reaction may be performed in a nitrogen atmosphere and an anhydrous system, and prepared at a temperature of −10° C. to −78° C.

(Synthesis Method 4)

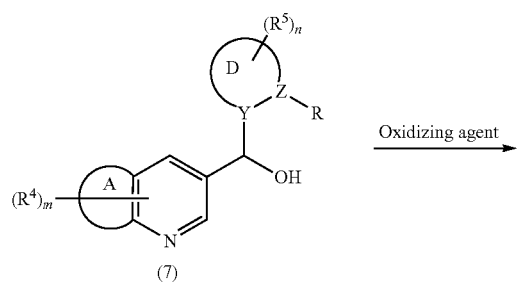

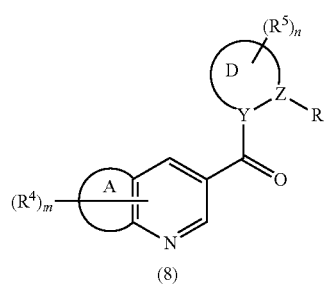

(In the formulae, R, R⁴, R⁵, A, D, Y, Z, m and n represent the same meaning as those described above.)

A compound represented by Formula (8) is produced by oxidation by reacting an oxidizing agent with a compound represented by Formula (7). The above oxidation reaction may be performed without particular limitation as long as the reaction oxidizes a secondary hydroxyl group. For example, an oxidation method such as a Jones oxidation, an ozone oxidation, or a Swern oxidation, or using an oxidizing reagent, such as manganese dioxide, or a Dess-Martin reagent, may be adopted.

(Synthesis Method 5)

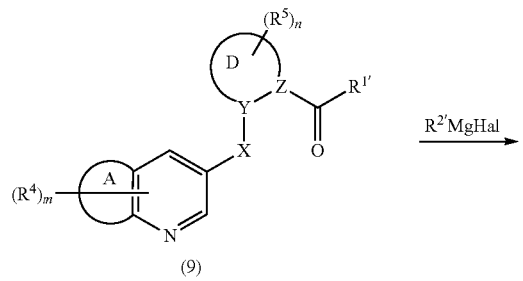

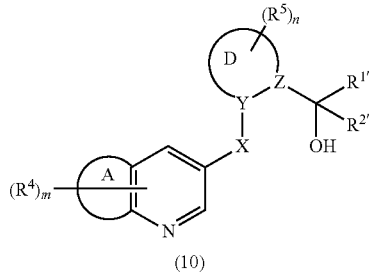

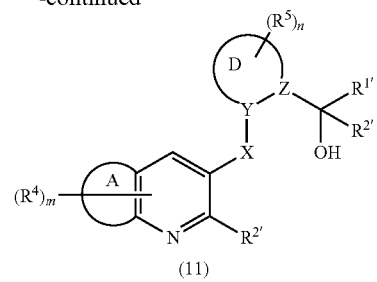

(In the formulae, $R^4$, $R^5$, A, D, X, Y, Z, m and n represent the same meaning as those described above. $R^{1'}$ and $R^{2'}$, among the above $R^1$ to $R^3$, represent an unsubstituted or substituted alkyl group, an unsubstituted or substituted alkenyl group, an unsubstituted or substituted alkynyl group, an unsubstituted or substituted aryl group, or an unsubstituted or substituted heterocyclic ring. Hal represents a halogen atom.)

A compound represented by Formula (10) may be produced by reacting an equivalent of a Grignard reagent with a compound represented by Formula (9). Also, a compound represented by Formula (11) may be produced by reacting at least two equivalents of a Grignard reagent with the compound represented by Formula (9).

(Synthesis Method 6)

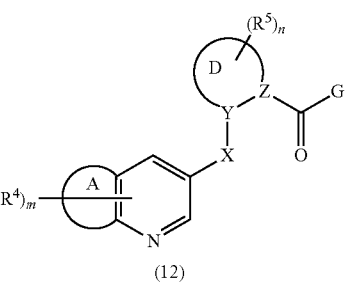

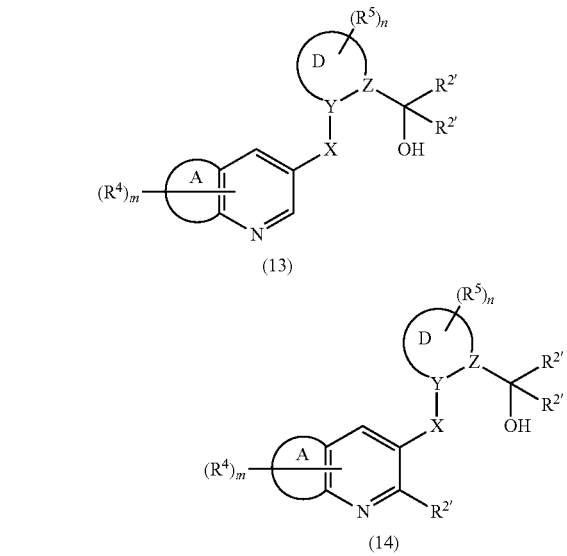

(In the formulae, $R^4$, $R^5$, $R^{2'}$, A, D, X, Y, Z, m, n and Hal represent the same meaning as those described above. G represents a leaving group, such as an alkoxy group, or a halogen atom.)

A compound represented by Formula (13) may be produced by reacting one equivalent of a Grignard reagent with a compound represented by Formula (12). Also, a compound represented by Formula (14) may be produced by reacting at least two equivalents of a Grignard reagent with the compound represented by Formula (12).

(Synthesis Method 7)

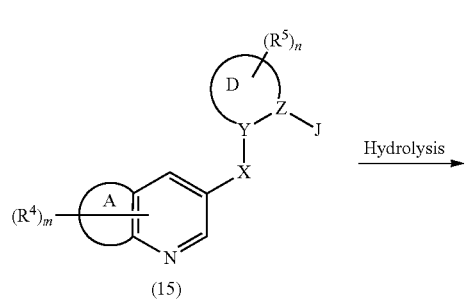

(15)

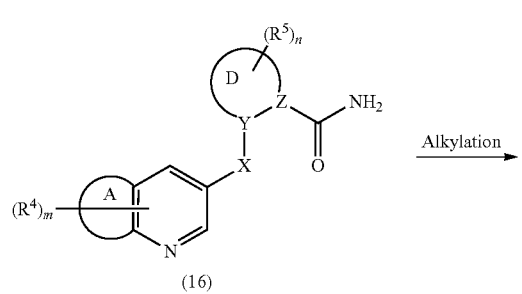

(16)

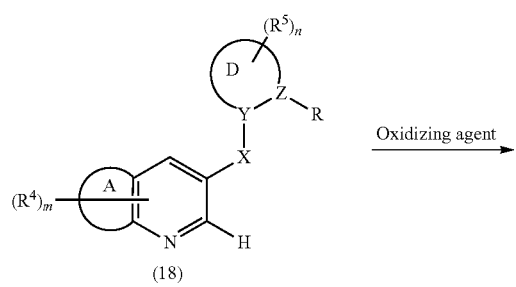

(17)

(In the formulae, $R^4$, $R^5$, A, D, X, Y, Z, m, and n represent the same meaning as those described above. J represents an alkoxycarbonyl group or a cyano group. $K^1$ and $K^2$ represent an alkyl group.)

A compound represented by Formula (16) may be produced by hydrolysis using conventional methods. Also, a compound represented by Formula (17) may be produced by reacting an alkylating agent in the presence of a base.

(Synthesis Method 8)

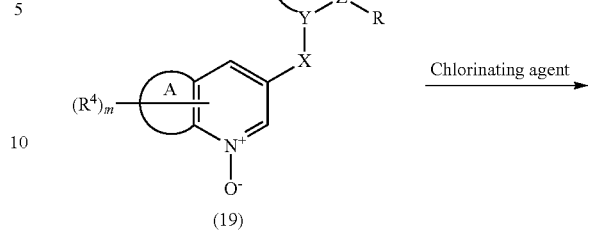

(18)

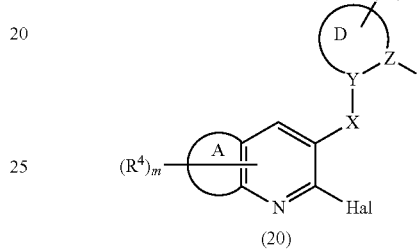

(19)

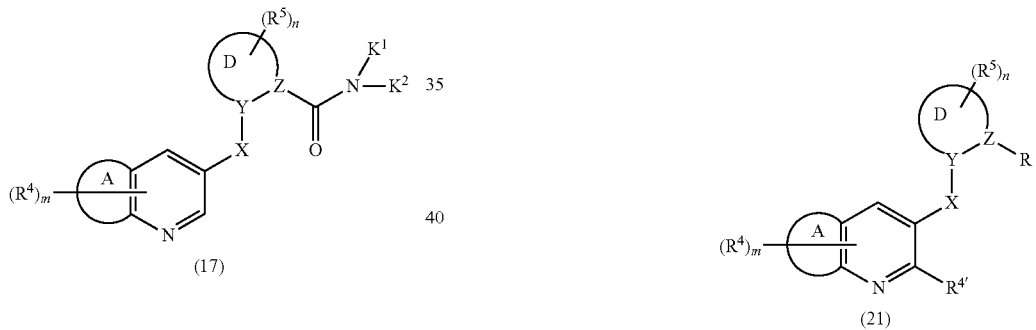

(20)

(21)

(In the formulae, R, $R^4$, $R^5$, A, D, X, Y, Z, m, n and Hal represent the same meaning as those described above. $R^{4'}$ represents an unsubstituted or substituted alkoxy group, an unsubstituted or substituted alkyl group, an unsubstituted or substituted alkenyl group, an unsubstituted or substituted alkynyl group, an unsubstituted or substituted aryl group, or an unsubstituted or substituted heterocyclic ring, an unsubstituted or substituted amino group, or an unsubstituted or substituted thioalkyl group.)

An N-oxide compound represented by Formula (19) may be produced by oxidizing a compound represented by Formula (18) using conventional methods such as the use of an oxidizing agent. A compound represented by Formula (20) may be produced by reacting a conventional halogenating agent such as phosphorus oxychloride with the compound represented by Formula (19). And then, the compound represented by Formula (20) is subjected to a nucleophilic substitution reaction or a coupling reaction using an organic metal catalyst to synthesize a compound represented by Formula (21).

(Synthesis Method 9)

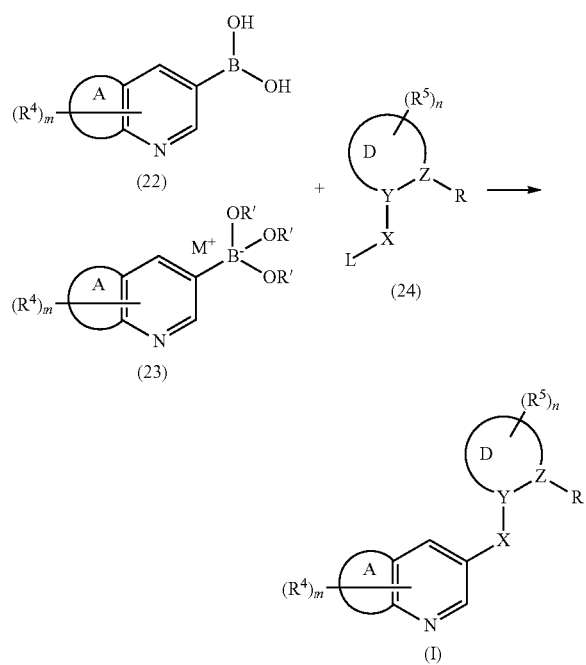

(In the formulae, R, $R^4$, $R^5$, A, D, X, Y, Z, m, and n represent the same meaning as those described above. R' represents a $C_{1-8}$ alkyl group. M represents an alkali metal such as lithium, sodium, or potassium. L represents a halogen atom.

The compound represented by Formula (I) may be prepared by a Suzuki coupling reaction of a boronic acid derivative represented by Formula (22) or Formula (23) and a halide derivative represented by Formula (24).

The N-oxide compound may be prepared by a conventional oxidation reaction. For example, in solvents or in the absence of solvents, it may be prepared by causing contact between the compound represented by Formula (I) and peroxide such as hydrogen peroxide.

In any reaction, after the reaction is completed, the resultant is subjected to a normal post reaction operation in an organic synthetic chemistry, followed by subjecting to a conventional separation and purification, if needed, to efficiently isolate a desired product.

The structure of the desired product may be identified and confirmed using $^1$H-NMR spectrum, IR spectrum, or mass spectrum measurements, or by elemental analysis or the like.

2) Agricultural Fungicide

An agricultural fungicide according to the present invention contains, as an active ingredient thereof, at least one selected from the group consisting of the nitrogen-containing heterocyclic compound, the salt thereof, and the N— oxide compound thereof.

The fungicide according to the present invention has an excellent fungicidal capacity over a wide variety of filamentous fungi, such as bacteria which belong to Oomycetes, Ascomycetes, Deuteromycetes, or Basidiomycetes.

The fungicide according to the present invention may be used to prevent various diseases that occur in the cultivation of agricultural crops including flowers, turf, and grass through seed treatment, foliar spraying, soil application or submerged application.

For example, it may be used to prevent:

sugar beet: Leaf spot (*Cercospora beticola*), Black root rot (*Aphanomyces cochlloides*), Root rot (*Thanatephorus cucumeris*), Leaf rot (*Thanatephorus cucumeris*);

peanut: Brown leaf spot (*Mycosphaerella arachidis*), Black rust (*Mycosphaerella berkeleyi*);

cucumber: Powdery mildew (*Sphaerotheca fuliginea*), Downy mildew (*Pseudoperonospora cubensis*), Gummy stem blight (*Mycosphaerella melonis*), Wilt (*Fusarium oxysporum*), Sclerotinia rot (*Sclerotinia sclerotiorum*), Gray mold (*Botrytis cinerea*), Anthracnose (*Colletotrichum orbiculare*), Scab (*Cladosporium cucumerinum*), Target leaf spot (*Corynespora cassicola*), Damping-off (*Pythium debaryanam, Rhizoctonia solani Kuhn*), Bacterial spot (*Pseudomonas syringae* pv. *Lecrymans*);

tomato: Gray mold (*Botrytis cinerea*), Leaf mold (*Cladosporium fulvum*), Phytophthora root rot (*Phytophthora infestans*);

eggplant: Gray mold (*Botrytis cinerea*), Black rot (*Corynespora melongenae*), Powdery mildew (*Erysiphe cichoracearum*), Sooty mold (*Mycovellosiella nattrassii*);

strawberry: Gray mold (*Botrytis cinerea*), Powdery mildew (*Sohaerotheca humuli*), Anthracnose (*Colletotrichum acutatum, Colletotrichum fragariae*), Phytophthora root rot (*Phytophthora cactorum*);

onion: Gray mold neck rot (*Botrytis allii*), Gray mold (*Botrytis cinerea*), Leaf blight (*Botrytis squamosa*), Downy mildew (*Peronospora destructor*);

cabbage: Clubroot (*Plasmodiophora brassicae*), Soft rot (*Erwinia carotovora*), Downy mildew (*Peronospora parasitica*);

kidney bean: Sclerotinia rot (*Sclerotinia sclerotiorum*), Gray mold (*Botrytis cinerea*);

apple: Powdery mildew (*Podosphaera leucotricha*), Scab (*Venturia inaequalis*), Monilia disease (*Monilinia mali*), Brooks fruit spot (*Mycosphaerella pomi*), Brown canker (*Valsa mali*), Alternaria blotch (*Alternaria mali*), Cedar apple rust (*Gymnosporangium yamadae*), White rot (*Botryosphaeria berengeriana*), Anthracnose (*Glomerella cingulata, Collectotrichum acutatum*), Marssonia blotch (*Diplocarpon mali*), Fly speck (*Zygophiala jamaicensis*), Sooty blotch (*Gloeodes pomigena*);

persimmon: Powdery mildew (*Phyllactinia kakicola*), Anthracnose (*Gloeosporium kaki*), Angular leaf spot (*Cercospora kaki*);

peach: Brown rot (*Monilinia fructicola*), Scab (*Cladosporium carpophilum*), Phomopsis bacterial rot (*Phomopsis* sp.);

cherry: Brown rot (*Monilinia fructicola*);

grape: Gray mold (*Botrytis cinerea*), Powdery mildew (*Uncinula necator*), Ripe rot (*Glomerella cingulata, Colletorichum acutatum*), Downy mildew (*Plasmopara viticola*), Bird's eye rot (*Elsinoe ampelina*), Leaf spot (*Pseudocercospora vitis*), Black rot (*Guignardia bidwellii*);

pear: Scab (*Venturia nashicola*), Cedar apple rust (*Gymnosporangium asiaticum*), Leaf spot (*Alternaria kikuchiana*), Black rot (*Botryosphaeria berenengeriana*), Powdery mildew (*Phyllactinia mali*);

tea: Collar rot (*Pestalotia theae*), Anthracnose (*Colletotrichum theae-sinensis*);

citrus: Scab (*Elsinoe fawcetti*), Blue mold (*Penicillium italicum*), Green mold (*Penicillium digitatum*), Gray mold (*Botrytis cinerea*), Melanose (*Diaporthe citri*), Bacterial canker (*Xanthomonas campestris* pv.Citri);

wheat: Powdery mildew (*Erysiphe graminis* f. sp. *tritici*), Petch (*Gibberella zeae*), Leaf rust (*Puccinia recondita*), Brown snow mold (*Pythium iwayamai*), Red snow mold (*Monographella nivalis*), Black eye spot (*Pseudocer-* cosporella herpotrichoides), Leaf blight (*Septoria tritici*), Glume blotch (*Leptosphaeria nodorum*), *Typhula* snow blight (*Typhula incarnata*), *Sclerotinia* snow blight (*Myriosclerotinia borealis*), Take-all (*Gaeumanomyces graminis*);

barley: Leaf stripe (*Pyrenophora graminea*), *Rhynchosporium* scald (*Rhynchosporium secalis*), Loose smut (*Ustilago tritici, U.nuda*);

rice: Neck rot (*Pyricularia oryzae*), Sheath blight (*Rhizoctonia solani*), Bakanae disease (*Gibberalla fujikuroi*), *Heliminthosporium* blight (*Cochliobolus niyabeanus*), Damping-off (*Pythium graminicolum*), Bacterial blight (*Xanthomonas oryzae*), Bacterial damping-off (*Burkholderia plantarii*), Brown stripe (*Acidovorax avenae*), Bacterial grain rot (*Burkholderia glumae*);

tobacco: *Sclerotinia* rot (*Sclerotinia sclerotiorum*), Powdery mildew (*Erysiphe cichoracearum*);

tulip: Gray mold (*Botrytis cinerea*);

bent grass: *Sclerotinia* snow blight (*Sclerotinia borealis*), Brown blight (*Pythium asphanidermatum*);

orchard grass: Powdery mildew (*Erysiphe graminis*);

soybean: Purple blotch (*Cercospora kikuchii*), Downy mildew (*Peronospora Manshurica*), Stem rot (*Phytophthora sojae*);

potato•tomato: *Phytophthora* root rot (*phytophthora infestans*);

or the like.

Also, the fungicide according to the present invention exhibits an excellent fungicidal effect on resistant bacteria as well. Examples of the resistant bacteria include: gray mold germs (*Botrytis cinerea*), sugar beet brown spot germs (*Cercospora beticola*), apple scab germs (*Venturia inaequalis*), pear scab germs (*Venturia nashicola*), resistant to a benzimidazole-based fungicide such as thiophanate-methyl, benomyl, or carbendazim; Gray mold germs (*Botrytis cinerea*) resistant to a dicarboximide-based fungicide (such as vinclozolin, procymidone, or iprodione), and the like.

Examples of diseases in which application of the fungicide according to the present invention is more preferable include Scab of apple, Gray mold of cucumber, Powdery mildew of wheat, Late blight of tomato, Leaf rust of wheat, Neck rot of rice, Wilt disease of cucumber, and the like.

Also, the fungicide according to the present invention is an agent with low phytotoxicity, low toxicity to fish or warm-blooded animals, and high safety.

The fungicide according to the present invention may be used in an agrochemically acceptable form, that is, in a form of an agrochemical formulation, such as a water-dispersible powder, granules, a powder, an emulsion, a water-soluble powder, a suspension, or water-dispersible granules.

Examples of an additive and a carrier used in the formulation of a solid include: vegetable powder such as soybean flour or wheat flour; mineral fine powder such as diatomite, apatite, plaster, talc, bentonite, pyrophylite, or clay; an organic or inorganic compound such as sodium benzoate, urea, or sulfate of soda; and the like.

Examples of a solvent used in the formulation of a liquid include: an aromatic hydrocarbon such as kerosene, xylene, or a petroleum-based aromatic hydrocarbon; cyclohexane, cyclohexanone, dimethyl formamide, dimethyl sulfoxide, an alcohol, acetone, trichloroethylene, methylisobutylketone, mineral oil, vegetable oil, water, and the like.

Also, in the formulations, in order to attain a uniform and stable form, a surfactant may be added as necessary.

The surfactant which may be added is not particularly limited. Examples of the surfactant include: a non-ionic surfactant such as polyoxyethylene-added alkylphenylether, polyoxyethylene-added alkylether, polyoxyethylene-added higher fatty acid ester, polyoxyethylene-added sorbitan higher fatty acid ester, polyoxyethylene-added tristyrylphenylether; a sulfuric ester salt of polyoxyethylene-added alkylphenylether, an alkylbenzene sulfonate, a sulfuric ester salt of higher alcohol, an alkylnaphthalene sulfonate, a polycarboxylate, a lignin sulfonate, a formaldehyde condensate of alkylnaphthalene sulfonate, an isobutylene-anhydrous maleic acid copolymer, and the like.

The thus obtained water-dispersible powder, the emulsion, a flowable agent, the water-soluble powder, or the water-dispersible granules is diluted with water to a predetermined concentration and used as a solution, a suspension, or an emulsion to be sprayed onto plants. Also, the powder and the granules are used sprayed onto plants as they are.

The amount of the fungicide according to the present invention is, normally, with respect to the total amount of the formulation, preferably 0.01 to 90% by weight, and more preferably 0.05 to 85% by weight.

The application rate of the fungicide according to the present invention, although it differs depending on weather conditions, formulation form, time of application, method of application, area of application, control target disease, or target crop, is, normally as an amount of active ingredient compound per 1 hectare, 1 to 1,000 g, and preferably 10 to 100 g.

When the water-dispersible powder, the emulsion, the suspension, the water-soluble powder, or the water-dispersible granules is diluted with water, the applied concentration is 1 to 1,000 ppm, and preferably 10 to 250 ppm.

The fungicide according to the present invention may be mixed with other fungicides or insecticides/acaricides, or synergists.

Representative examples of other fungicides, insecticides, acaricides, and plant growth regulators that may be mixed and used with the fungicide according to the present invention are shown below.

Fungicide:

benzoimidazole series such as benomyl, carbendazim, fuberidazole, thiabendazole, or thiophanate-methyl;

dicarboximide series such as chlozolinate, iprodione, procymidone, or vinclozoline;

DMI-fungicide such as imazalil, oxpoconazole, perfrazoate, prochloraz, triflumizole, triforine, pyrifenox, fenarimol, nuarimol, azaconazole, bitertanol, bromuconazole, cyproconazole, difenoconazole, diniconazole, epoxyconazole, fenbuconazole, fluquinconazole, fulsilazole, flutriafol, hexaconazole, imibenconazole, ipconazole, metconazole, myclobutanil, penconazole, propiconazole, prothioconazole, simeconazole, tebuconazole, tetraconzole, triadimefon, triadimenol, triticonazole, etaconazole, furconazole-cis, ipconazole, or imibenconazole;

phenylamide series such as benalaxyl, furalaxyl, metalaxyl, metalaxyl-M, oxadixyl, or ofurace;

amine series such as aldimorph, dodemorph, fenpropimorph, tridemorph, fenpropidine, piperalin, or spiroxamine;

phosphorothiolate series such as EDDP, iprobenfos, pyrazophos;

dithiolane series such as isoprothiolane;

carboxamide series such as benodanil, boscalid, carboxin, fenfuran, flutolanil, furametpyr, mepronil, oxycarboxin, penthiopyrad, or thifluzamide;

hydroxy-(2-amino)pyrimidine such as bupurimate, dimethirimol, or ethirimol;

AP fungicide (anilinopyrimidine) such as cyprodinil, mepanipyrim, or pyrimethanil;

N-phenylcarbamate such as diethofencarb; QoI-fungicide (Qo inhibitor) such as azoxystrobin, picoxystrobin, pyraclostrobin, kresoxim-methyl, trifloxystrobin, dimoxystrobin, metominostrobin, orysastrobin, famoxadone, fluoxastrobin, fenamidone, metominofen, pyribencarb;

PP fungicide (phenylpyrrole) such as fenpiconyl, fludioxonil;

quinoline series such as quinoxyfen;

AH fungicide (aromatic hydrocarbon) such as biphenyl, chloroneb, dicloran, quintozene, tecnazene, or tolktfos-methyl;

MBI-R such as phthalide, pyroquilon, or tricyclazole;
MBI-D such as carpropamid, diclocymet, or fenoxanil;
SBI agent such as fenhexamid, pyributicarb, or terbinafin;
phenylurea such as pencycuron;
QiI-fungicide (Qi inhibitor) such as cyazofamid;
benzamide such as zoxamide;
enopyranuron such as blasticidin, mildiomycin;
hexopyranosyl such as kasugamycin;
glucopyranocyl such as streptomycin, validamycin;
cyanoacetamide such as cymoxanil;
carbamate such as propamocarb, prothiocarb, or polycarbamate;
uncoupling agent such as binapacryl, dinocap, ferimzone, or fluazinam;
organotin compound such as triphenyltin acetate, triphenyltin chloride, or triphenyltin hydroxide;
organophosphate such as phosphoric acid, tolclofos-methyl, or fosetyl;
phthalamic acid such as techlofthalam;
benzotriazine such as triazoxide;
benzenesulfonamide such as flusulfamide;
pyridazinone such as diclomezin;
CAA fungicide (carboxylic acid amid) such as dimethomorph, flumorph, benthiavalicarb, iprovalicarb, or mandipropamid;
tetracycline such as oxytetracycline;
thiocarbamate such as methasulfocarb; or
other compounds such as etridiazole, polyoxin, oxolinic acid, hydroxyisoxazol, octhinoline, silthiofam, diflumetorim, acibenzolar-S-methyl, probenazole, tiadinil, ethaboxam, cyflufenamid, proquinazid, metrafenone, fluopicolide, copper (II) hydroxide, organocopper, sulfur, ferbam, manzeb, maneb, metiram, propineb, thiuram, zineb, ziram, captan, captafol, folpet, chlorothalonil, dichlofluanid, tolylfluanid, dodine, guazatine, iminoctadine, anilazine, dithianon, chloropicrin, dazomet, metam-sodium, chinomethionat, cyprofuram, silthiofam, ago-bacterium, or fluoroimide.

Insecticides•acaricides:
Organophosphorous and carbamate series insecticides:
fenthion, fenitrothion, diazinon, chlorpyrifos, ESP, vamidothion, phenthoate, dimethoate, formothion, malathon, trichlorhon, thiometon, phosmet, dichlorvos, acephate, EPBP, methyl parathion, oxydemeton-methyl, ethion, salithion, cyanophos, isoxathion, pyridaphenthion, phosalone, methidathion, sulprofos, chlorfenvinphos, tetrachlorvinphos, dimethylvinhos, propaphos, isofenphos, ethylthiometon, profenofos, pyraclofos, monocrotophos, Azinphosmethyl, aldicarb, methomyl, thiodicarb, carbofuran, carbosulfan, benfuracarb, furathiocarb, propoxur, BPMC, MTMC, MIPC, carbaryl, pirimicarb, ethiofencarb, fenoxycarb, EDDP or the like.

Pyrethroid series insecticides:
permethrin, cypermethrin, Deltamethrine, fenvalerate, fenpropathrin, pyrethrin, allethrin, tetramethrine, resmethrin, dimethrin, propathrin, phenothrin, prothrin, fluvalinate, cyfluthrin, cyhalothrin, flucythrinate, ethofenprox, cycroprothrin, tralomethrin, silafluofen, brofenprox, acrinathrin or the like.

Other insecticides of benzoyl urea series:
microbial agrochemicals such as diflubenzuron, chlorfluazuron, hexaflumuron, triflumuron, tetrabenzuron, flufenoxuron, flucycloxuron, buprofezin, pyriproxyfen, methoprene, benzoepin, diafenthiuron, acetamiprid, imidacloprid, nitenpyram, fipronil, cartap, thiocyclam, bensultap, nicotine sulfate, rotenone, metaldehyde, machine oil, BT, insect pathogenic viruses, or the like.

Nematocides:
Fenamiphos, fosthiazate or the like.

Acaricides:
chlorobenzilate, phenisobromolate, dicofol, amitraz, BPPS, benzomate, hexythiazox, fenbutatin oxide, polynactins, chinomethionat, CPCBS, tetradifon, avermectin, milbemectin, clofentezine, cyhexatin, pyridaben, fenpyroximate, tebufenpyrad, pyrimidifen, phenothiocarb, dienochloror the like.

Plant growth regulator:
abscisic acid, indolebutyric acid, uniconazole, ethylchlozate, ethephon, cloxyfonac, chlormequat, chlorella extract, calcium peroxide, cyanamide, dichlorprop, gibberellin, daminozide, decyl alcohol, trinexapac-ethyl, mepiquat chloride, paclobutrazol, paraffin, wax, piperonyl butoxide, pyraflufen-ethyl, flurprimidol, prohydrojasmon, prohexadione-calcium, benzylaminopurine, pendimethalin, forchlorfenuron, maleic hydrazide potassium, 1-naphthylacetamide, 4-CPA, MCPB, corrin, oxyquinoline sulfate, ethychlozate, butralin, 1-methylcyclopropene, aviglycine hydrochloride.

EXAMPLES

Hereinafter, the present invention is described in more detail with reference to examples, however, the present invention is not in the least limited by the following examples.

Example 1

Synthesis of
1-[2-(quinolin-3-yloxy)-phenyl]-ethanone

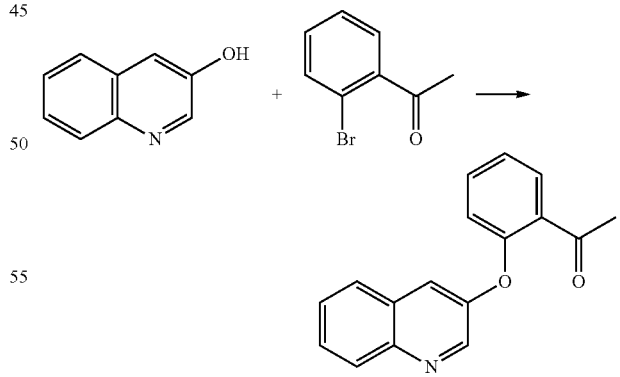

0.73 g of 3-quinolinol, 1.8 g of cesium carbonate, 0.18 g of dipivaloylmethane, 2.0 g of 2-bromoacetophenone, and 0.50 g of copper (I) chloride were dissolved in 10 ml of N-methylpyrrolidone, and the mixture was stirred for 3 hours at 130° C. The resultant was purified by silica gel column chromatography, and 0.82 g of 1-[2-(quinolin-3-yloxy)-phenyl]-ethanone (Compound Number 1) was obtained.

Compounds represented by Compound Numbers 2 to 13 were synthesized in the same manner as that of Example 1.

Example 2

Synthesis of 3-(2-t-butyl-phenoxy)-quinoline

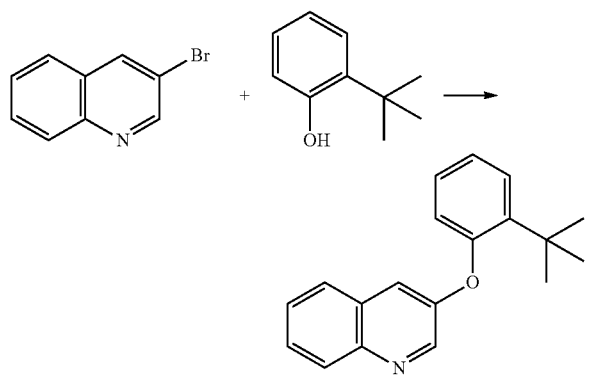

0.60 g of 2-t-butylphenol, 1.3 g of cesium carbonate, 0.07 g of dipivaloylmethane, 0.42 g of 3-bromoquinoline, and 0.20 g of copper (I) chloride were dissolved in 4 ml of N-methylpyrrolidone, and the mixture was stirred for one day at 130° C. The resultant was purified by silica gel column chromatography, and 0.04 g of 3-(2-t-butyl-phenoxy)-quinoline (Compound Number 14) was obtained.

Compounds represented by Compound Numbers 15 to 19 were synthesized in the same manner as that of Example 2.

Example 3

Synthesis of 2-chloro-6-(quinolin-3-yloxy)-benzamide

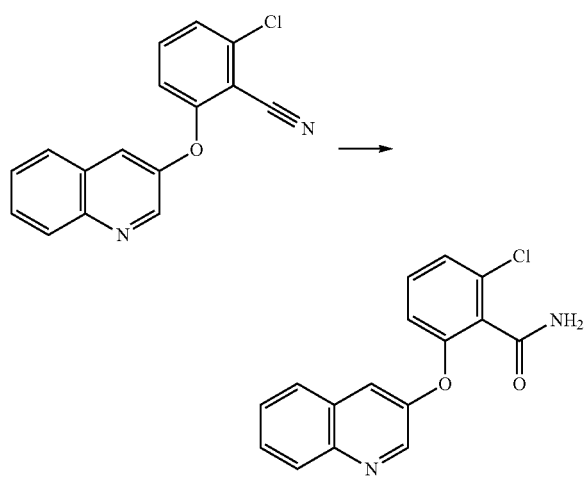

1.18 g of 2-chloro-6-(quinolin-3-yloxy)-benzonitrile was dissolved in 5 ml of 80% sulfuric acid and the mixture was stirred for 3 hours at 100° C. After being neutralized with an aqueous solution of sodium hydroxide, the liquid was separated with ethyl acetate, the organic layer was concentrated and 1.03 g of 2-chloro-6-(quinolin-3-yloxy)-benzamide (Compound Number 20) was obtained.

A compound represented by Compound Number 21 was synthesized in the same manner as that of Example 3.

Example 4

Synthesis of 2-bromo-N,N-dimethyl-6-(quinolin-3-yloxy)-benzamide

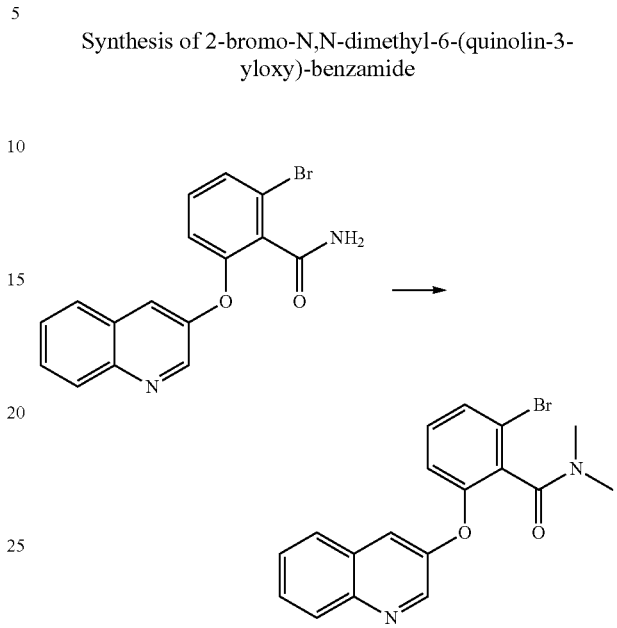

After 0.34 g of 2-bromo-6-(quinolin-3-yloxy)-benzamide was dissolved in 2 ml of N-methylpyrrolidone, 47 mg of sodium hydride was added thereto at room temperature. After 0.21 g of methyl iodide was added to the reaction solution, the mixture was heated to 100° C. and stirred for 4 hours. After the liquid was separated with ethyl acetate, the solvent was evaporated and the resultant was purified by silica gel column chromatography to obtain 0.11 g of 2-bromo-N,N-dimethyl-6-(quinolin-3-yloxy)-benzamide (Compound Number 22).

Example 5

Synthesis of 1-[2-(quinolin-3-yloxy)-phenyl]-ethanone oxime

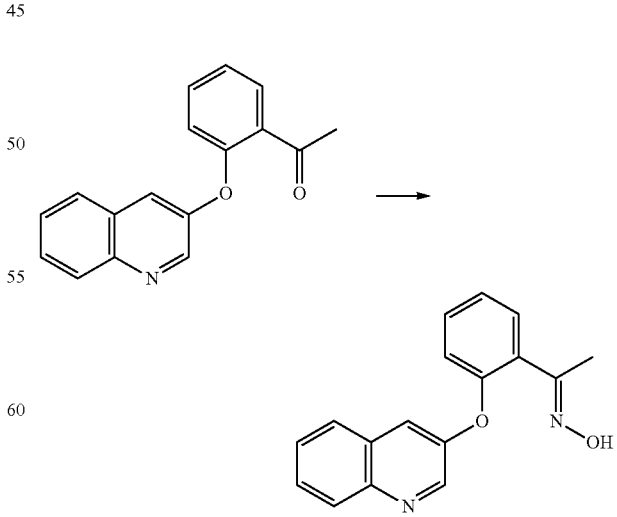

0.46 g of 1-[2-(quinolin-3-yloxy)-phenyl]-ethanone and 0.15 g of hydroxylamine hydrochloride were dissolved in 3 ml of pyridine and then the mixture was stirred for 24 hours at room temperature. After the reaction mixture was treated with dilute hydrochloric acid and separated with ethyl acetate, the organic layer was concentrated to obtain 0.54 g of 1-[2-(quinolin-3-yloxy)-phenyl]-ethanone oxime (Compound Number 23).

Compounds represented by Compound Numbers 24 to 26 were synthesized in the same manner as that of Example 5.

Example 6

Synthesis of 3-[2-(1,1-dimethoxy-ethyl)-phenoxy]-quinoline

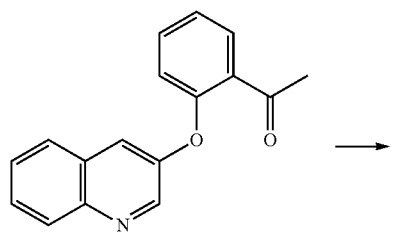

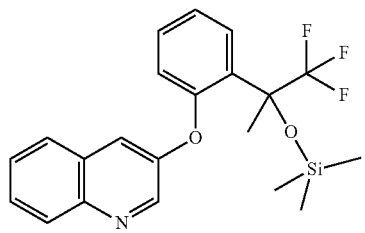

After 0.26 g of 1-[2-(quinolin-3-yloxy)-phenyl]-ethanone and 0.16 g of (trifluoromethyl)trimethylsilane were dissolved in 3 ml of tetrahydrofuran, 2 drops of tetrabutylammonium fluoride (1.0 M tetrahydrofuran solution) was added under ice-cooling and then stirred for 4 hours. After the reaction mixture was concentrated and purified by silica gel column chromatography to obtain 0.34 g of 3-[2-(2,2,2-trifluoro-1-methyl-1-trimethylsilanyloxy-ethyl)-phenoxy]-quinoline (Compound Number 28).

Example 8

Synthesis of 1,1,1-trifluoro-2-[2-(quinolin-3-yloxy)-phenyl]-propan-2-ol

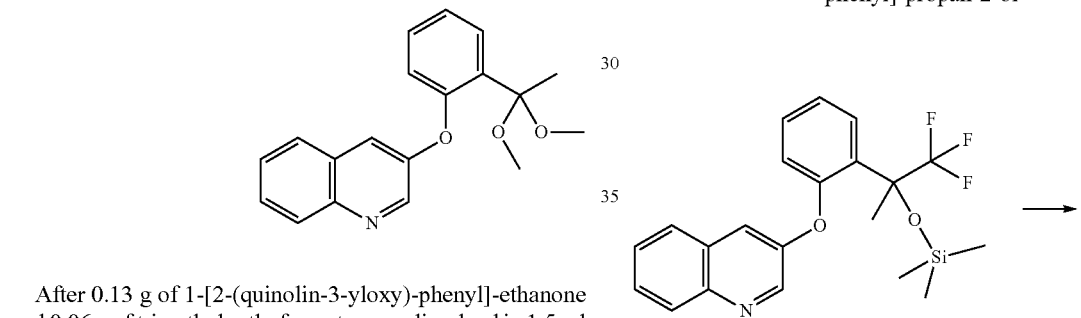

After 0.13 g of 1-[2-(quinolin-3-yloxy)-phenyl]-ethanone and 0.06 g of trimethyl orthoformate were dissolved in 1.5 ml of methanol, 0.02 g of tetrabutylammonium tribromide was added and the mixture was stirred for 4 days at room temperature. The reaction mixture was concentrated and then purified by silica gel column chromatography to obtain 0.08 g of 3-[2-(1,1-dimethoxy-ethyl)-phenoxy]-quinoline (Compound Number 27).

Example 7

Synthesis of 3-[2-(2,2,2-trifluoro-1-methyl-1-trimethylsilanyloxy-ethyl)-phenoxy]-quinoline

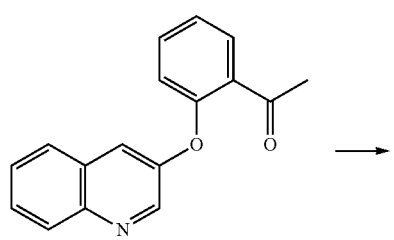

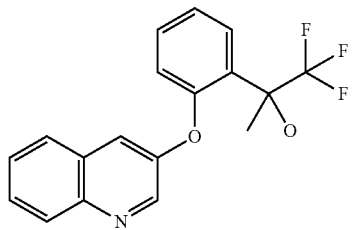

After 0.17 g of 3-[2-(2,2,2-trifluoro-1-methyl-1-trimethylsilanyloxy-ethyl)-phenoxy]-quinoline was dissolved in 1.5 ml of tetrahydrofuran, 1 ml of tetrabutylammonium fluoride (1.0 M tetrahydrofuran solution) was added and the mixture was stirred for 16 hours. The reaction mixture was concentrated and then purified by silica gel column chromatography to obtain 0.11 g of 1,1,1-trifluoro-2-[2-(quinolin-3-yloxy)-phenyl]-propan-2-ol (Compound Number 29).

Example 9

Synthesis of 2-[2-fluoro-6-(8-fluoro-quinolin-3-yloxy)-phenyl]-3,3-dimethyl-butan-2-ol

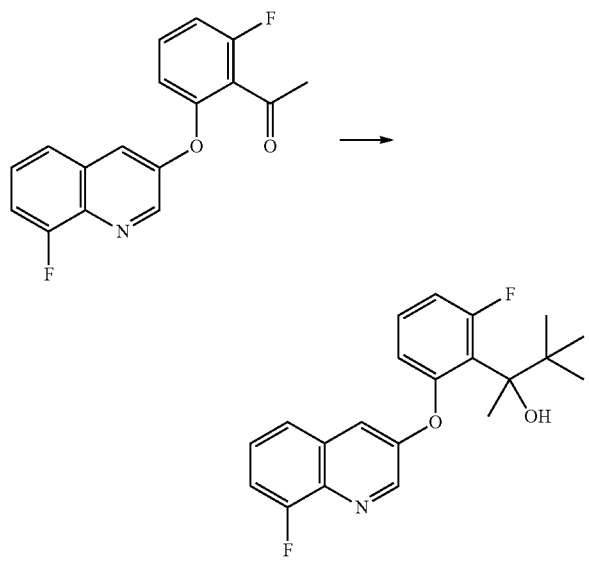

After 0.15 g of 1-[2-fluoro-6-(8-fluoro-quinolin-3-yloxy)-phenyl]-ethanone was dissolved in 1.5 ml of tetrahydrofuran, and then the solution was cooled to −78° C., 0.3 ml of t-butylmagnesium chloride (2.0 M diethyl ether solution) was added dropwise. After the reaction temperature was increased to room temperature, the reaction solution was treated with dilute hydrochloric acid, and then the liquid was separated with ethyl acetate. The organic layer was concentrated and then purified by silica gel column chromatography to obtain 0.04 g of 2-[2-fluoro-6-(8-fluoro-quinolin-3-yloxy)-phenyl]-3,3-dimethylbutan-2-ol (Compound Number 30).

Compounds represented by Compound Numbers 31 to 35 were synthesized in the same manner as that of Example 9.

Example 10

Synthesis of 2-[2-fluoro-6-(8-fluoroquinolin-3-yloxy)phenyl]propan-2-ol and 2-[2-fluoro-6-(8-fluoro-2-methylquinolin-3-yloxy)phenyl]propan-2-ol

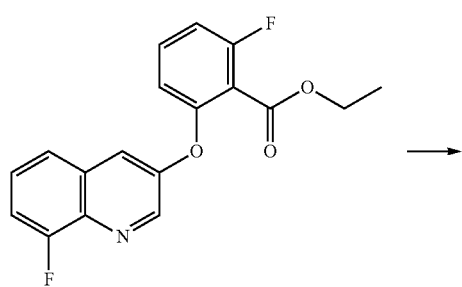

-continued

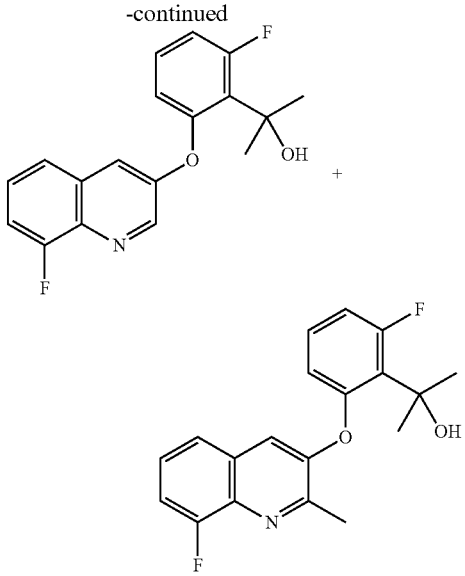

After 0.3 g of 2-fluoro-6-(8-fluoroquinolin-3-yloxy)-benzoic acid ethyl ester was dissolved in 4.5 ml of tetrahydrofuran, the solution was cooled to −78° C., and 0.77 ml of methylmagnesium chloride (3.0 M diethyl ether solution) was added dropwise. After the reaction temperature was increased to room temperature, the reaction solution was treated with dilute hydrochloric acid and the liquid was separated with ethyl acetate. The organic layer was concentrated and then purified by silica gel column chromatography to obtain 0.12 g of 2-[2-fluoro-6-(8-fluoroquinolin-3-yloxy)phenyl]propan-2-ol (Compound Number 36) and 0.05 g of 2-[2-fluoro-6-(8-fluoro-2-methylquinolin-3-yloxy)phenyl]propan-2-ol (Compound Number 37).

Compounds represented by Compound Numbers 38 to 49 were synthesized in the same manner as that of Example 10.

Example 11

Synthesis of 7-(quinolin-3-ylamino)-indan-1-one

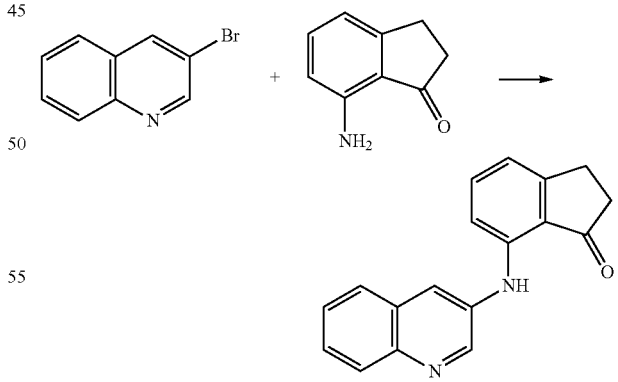

0.43 g of 3-bromoquinoline, 0.29 g of 7-aminoindan-1-one, 0.08 g of copper (I) iodide, 0.41 g of potassium carbonate, and 4 ml of N-methylpyrrolidone were mixed, and then the mixture was stirred for 2 hours at 200° C. The resultant mixture was purified by silica gel column chromatography to obtain 0.15 g of 7-(quinolin-3-ylamino)-indan-1-one (Compound Number 50).

A compound represented by Compound Number 51 was synthesized in the same manner as that of Example 11.

Example 12

Synthesis of 3-(t-butyl-benzyl)-8-fluoroquinoline

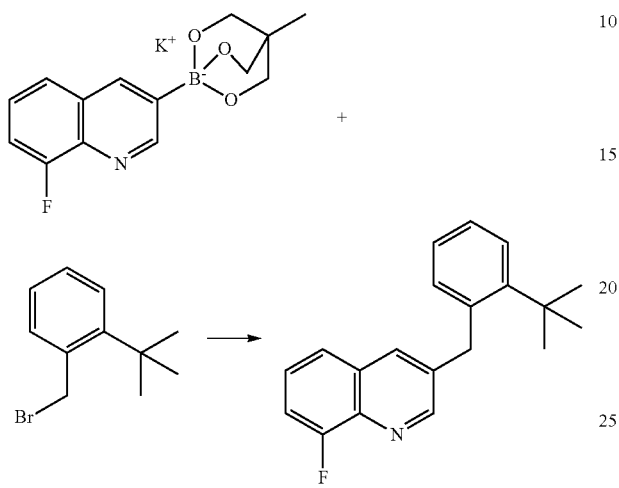

After 0.69 g of triol salt derived from 8-fluoroquinoline-3-boric acid and 1,1,1-tris(hydroxymethyl)ethane by a method reported in the literature (Angew. Chem. Int. Ed., 2008, 47, 928-931) and 0.45 g of 1-bromomethyl-2-t-butylbenzene were dissolved in 10 ml of toluene, 0.46 g of tetrakis triphenylphosphine palladium was added and the mixture was stirred for 3 hours. After the solvent of the reaction mixture was evaporated, the resultant was purified by silica gel column chromatography to obtain 0.14 g of 3-(t-butyl-benzyl)-8-fluoroquinoline (Compound Number 52).

A compound represented by Compound Number 53 was synthesized in the same manner as that of Example 12.

Example 13

Synthesis of (2-t-butyl-phenyl)-(8-fluoro-quinolin-3-yl)-methanol

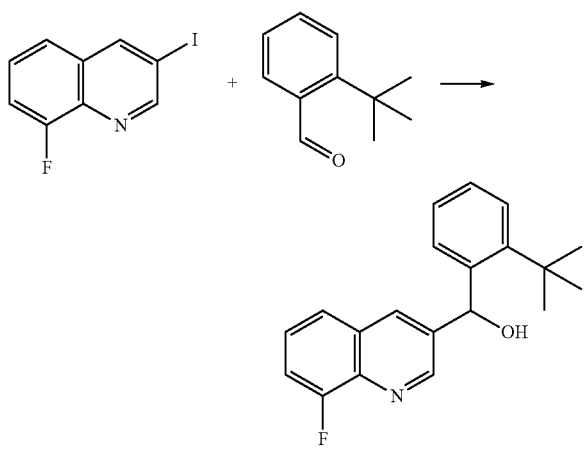

After 3 ml of tetrahydrofuran was cooled to −10° C., 0.91 ml of n-butyllithium (2.6 M hexane solution) and 1.35 ml of n-butylmagnesium chloride (0.91 M tetrahydrofuran solution) were added. After 30 minutes of stirring, 0.98 g of 8-fluoro-3-iodoquinoline was added and the mixture was stirred for 15 minutes. 0.49 g of 2-t-butylbenzaldehyde was added to the reaction solution and the mixture was stirred for 3 hours. After dilute hydrochloric acid was added to the reaction mixture, the liquid was separated with ethyl acetate. After the organic layer was concentrated and purified by silica gel column chromatography, 0.55 g of (2-t-butyl-phenyl)-(8-fluoro-quinolin-3-yl)-methanol (Compound Number 54) was obtained.

Compounds represented by Compound Numbers 55 to 56 were synthesized in the same manner as that of Example 13.

Example 14

Synthesis of (2-t-butyl-phenyl)-(8-fluoro-quinolin-3-yl)-methanone

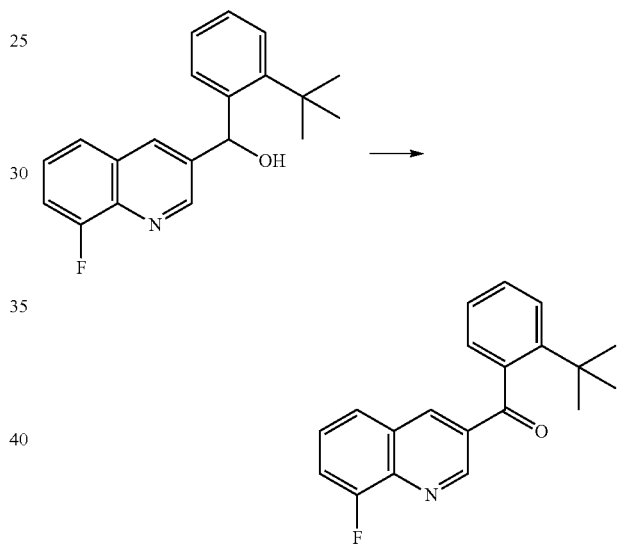

After 0.32 g of (2-t-butyl-phenyl)-(8-fluoro-quinolin-3-yl)-methanol was dissolved in 3 ml of dichloromethane, 0.51 g of Dess-Martin reagent was added and the mixture was stirred for 1 hour at room temperature. After water was added and then the liquid was separated with ethyl acetate, the organic layer was concentrated and purified by silica gel column chromatography to obtain 0.21 g of (2-t-butyl-phenyl)-(8-fluoro-quinolin-3-yl)-methanone (Compound Number 57).

Compounds represented by Compound Numbers 58 to 59 were synthesized in the same manner as that of Example 14.

Example 15

Synthesis of 2-chloro-3-(1,1-dimethylindan-7-yloxy)quinoline 0.2 g of 3-(1,1-dimethylindan-7-yloxy)quinolone was dissolved in 5 mL of chloroform, and 0.2 g of m-CPBA (70%) was added and stirred overnight at room temperature. After the reaction mixture was diluted with chloroform and washed with saturated sodium bicarbonate water, magnesium sulfate was added to dry the resultant. The solvent was evaporated under reduced pressure to obtain 0.2 g of 3-(1,1-dimethylindan-7-yloxy) quinoline-N-oxide.

The resultant was dissolved in phosphorus oxychloride and heated under reflux for 4 hours. Phosphorus oxychloride was evaporated under reduced pressure and the residue was dissolved in ethyl acetate and was washed with saturated sodium bicarbonate water. The organic layer was dried with magnesium sulfate and evaporated under reduced pressure. The crude product obtained was purified by silica gel column chromatography, and 0.13 g of 2-chloro-3-(1,1-dimethylindan-7-yloxy) quinoline (Compound Number 60) was obtained.

A compound represented by Compound Number 61 was synthesized in the same manner as that of Example 15.

Example 16

Synthesis of 3-(2-cyanophenoxy)quinoline

After 0.27 g of 3-hydroxyquinoline was dissolved in N-methyl-2-pyrrolidone, 0.087 g of sodium hydride (60% oil dispersion) was added under ice-cooling, and the mixture was stirred for 30 minutes. At the same temperature, 0.27 g of 2-fluorobenzonitrile was added and then the mixture was stirred for 6 hours at room temperature. After the reaction mixture was poured into ice water, extracted with ethyl acetate, and washed with saturated saline solution, the resultant was dried with magnesium sulfate. After the solvent was evaporated under reduced pressure, the crude product was purified by silica gel column chromatography to obtain 0.37 g of 3-(2-cyanophenoxy)quinoline (Compound Number 62).

Compounds represented by Compound Numbers 63 to 66 were synthesized in the same manner as that of Example 16.

Example 17

Synthesis of difluoro-[2-fluoro-6-(8-fluoroquinolin-3-yloxy)-ethyl acetate

Step 1) Synthesis of
8-fluoro-3-(3-fluoro-2-iodophenoxy)-quinoline

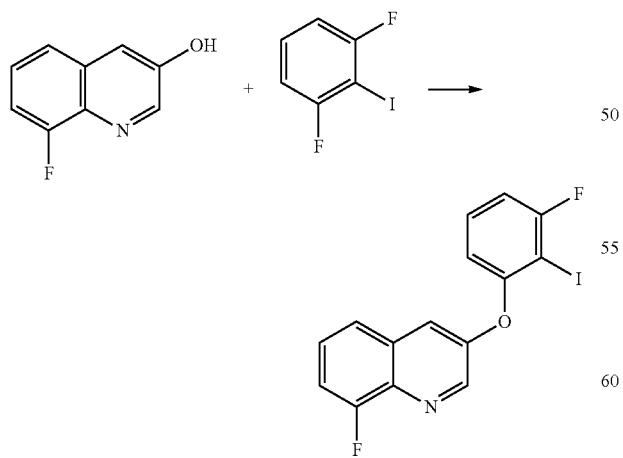

16 ml of N-methylpyrrolidone was added to 1.06 g of 8-fluoro-3-hydroxyquinoline, 1.94 g of 2,6-difluoroiodobenzene, and 1.7 g of potassium carbonate, and the mixture was stirred for 24 hours at 130° C. The reaction solution was purified by silica gel column chromatography, and 0.55 g of 8-fluoro-3-(3-fluoro-2-iodophenoxy)- quinoline was obtained.

Step 2) Synthesis of difluoro-[2-fluoro-6-(8-fluoroquinolin-3-yloxy)-ethyl acetate

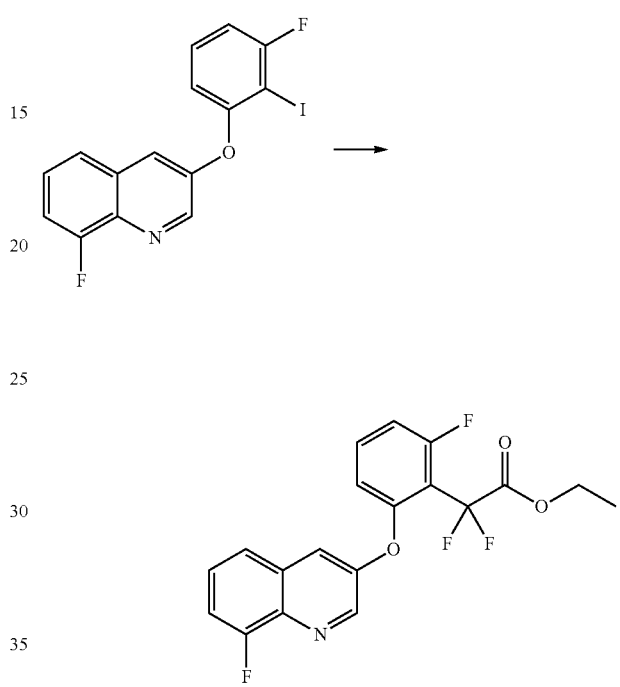

After 0.4 g of 8-fluoro-3-(3-fluoro-2-iodophenoxy)-quinoline was dissolved in 4 ml of dimethylsulfoxide, 0.25 g of copper (powder) and 0.41 g of bromodifluoroethyl acetate were added thereto, and then the mixture was stirred for 24 hours at 40° C. The reaction solution was purified by silica gel column chromatography, and 0.27 g of difluoro-[2-fluoro-6-(8-fluoroquinolin-3-yloxy)-ethyl acetate (Compound Number 292) was obtained.

Example 18

Synthesis of 1,1-difluoro-1-[2-fluoro-6-(8-fluoroquinolin-3-yloxy)-phenyl]-2-methyl-propan-2-ol

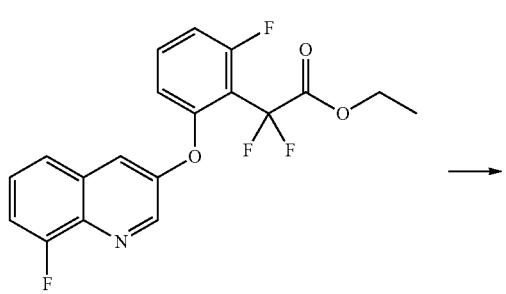

-continued

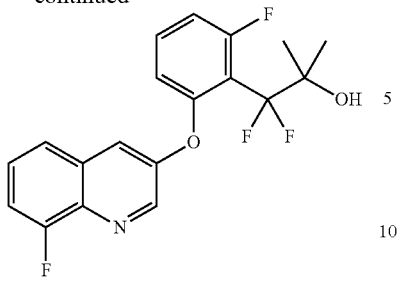

0.18 g of difluoro-[2-fluoro-6-(8-fluoroquinolin-3-yloxy)-ethyl acetate was dissolved in 3 ml of tetrahydrofuran and 0.4 ml of methylmagnesium chloride (3.0 M tetrahydrofuran solution) was added dropwise at 0° C. After the mixture was stirred for 2 hours at 0° C., dilute hydrochloric acid was added, and the liquid was separated with ethyl acetate. The organic layer was concentrated and purified by silica gel column chromatography to obtain 0.10 g of 1,1-difluoro-1-[2-fluoro-6-(8-fluoroquinolin-3-yloxy)-phenyl]-2-methyl-propan-2-ol (Compound Number 293).

Example 19

Synthesis of 1-[2-(7,8-difluoroquinolin-3-yloxy)-6-fluoro-phenyl]ethanone

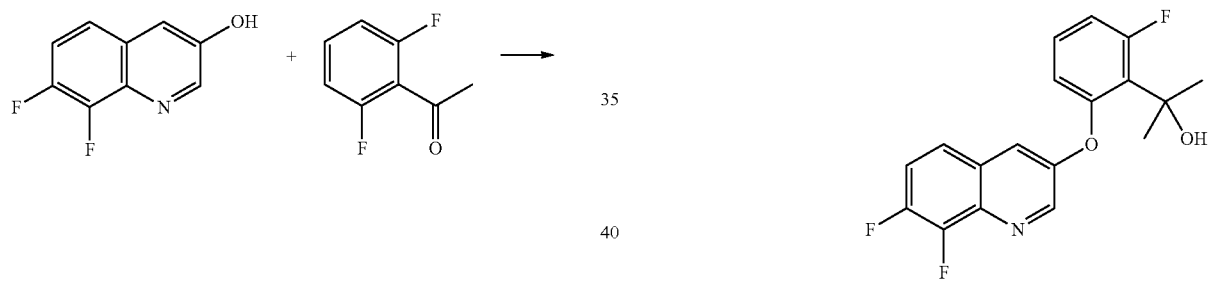

After 0.91 g of 7,8-difluoro-3-hydroxyquinoline and 0.94 g of 2,6-difluoroacetophenone were dissolved in 10 ml of dimethylformamide, 0.9 g of potassium carbonate was added. The reaction solution was heated to 100° C. and the mixture was stirred for 4.5 hours. Dilute hydrochloric acid was added to the reaction solution and the solution was separated by ethyl acetate. The organic layer was concentrated and purified by silica gel column chromatography to obtain 0.64 g of 1-[2-(7,8-difluoroquinolin-3-yloxy)-6-fluoro-phenyl]-ethanone (Compound Number 391).

Example 20

Synthesis of 2-[2-(7,8-difluoroquinolin-3-yloxy)-6-fluoro-phenyl]-propan-2-ol

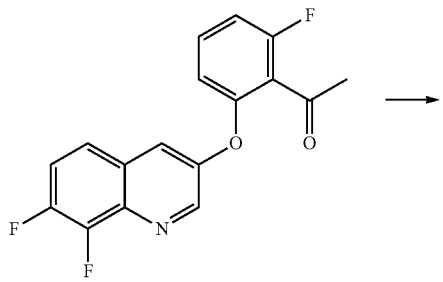

After 0.64 g of 1-[2-(7,8-difluoroquinolin-3-yloxy)-6-fluoro-phenyl]-ethanone was dissolved in 10 ml of tetrahydrofuran, the resultant was cooled to 0° C. and 1.5 ml of methylmagnesium chloride (3.0 M tetrahydrofuran solution) was added dropwise. Dilute hydrochloric acid was added to the reaction solution, and the liquid was separated with ethyl acetate. The organic layer was concentrated and purified by silica gel column chromatography to obtain 0.49 g of 2-[2-(7,8-difluoroquinolin-3-yloxy)-6-fluoro-phenyl]-propan-2-ol (Compound Number 124).

Example 21

Synthesis of 3-[2-(7,8-difluoroquinolin-3-yloxy)-6-fluoro-phenyl]-3-methyl-butan-2-one

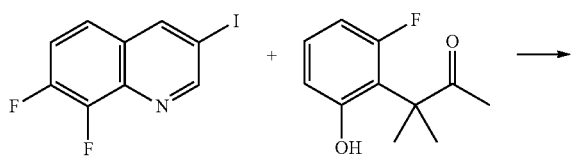

-continued

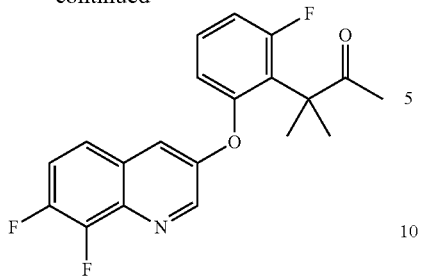

3 ml of N-methylpyrrolidone was added to 0.78 g of 7,8-difluoro-3-iodoquinoline, 0.26 g of 3-(2-fluoro-6-hydroxyphenyl)-3-methyl-butan-2-one, 1.05 g of cesium carbonate, 53 mg of dipivaloylmethane, and 0.27 g of copper (I) chloride. After 48 hours of stirring at 130° C., the reaction solution was filtered with CELITE and the liquid was separated with ethyl acetate. The organic layer was concentrated and purified by silica gel column chromatography to obtain 0.05 g of 3-[2-(7,8-difluoroquinolin-3-yloxy)-6-fluoro-phenyl]-3-methyl-butan-2-one (Compound Number 267).

Example 22

Synthesis of 2-fluoro-6-(8-fluoroquinolin-3-yloxy)-benzaldehyde

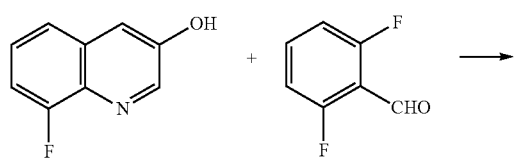

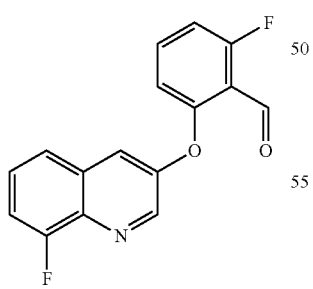

After 30 ml of acetonitrile was added to 3.0 g of 8-fluoro-3-hydroxyquinoline, 3.1 g of potassium carbonate and 3.5 g of 2,6-difluoroacetophenone were added. After the reaction solution was heated under reflux for 3 hours, the reaction solution was filtered with CELITE. After the filtrate was extracted with ethyl acetate, the organic layer was concentrated and purified by silica gel column chromatography to obtain 3.0 g of 2-fluoro-6-(8-fluoroquinolin-3-yloxy)-benzaldehyde (Compound Number 341).

Example 23

Synthesis of 1-[2-fluoro-6-(8-fluoroquinolin-3-yloxy)-phenyl]-propane-1,2-dione

Step 1) Synthesis of [2-fluoro-6-(8-fluoroquinolin-3-yloxy)-phenyl]-trimethylsilyloxy-acetonitrile

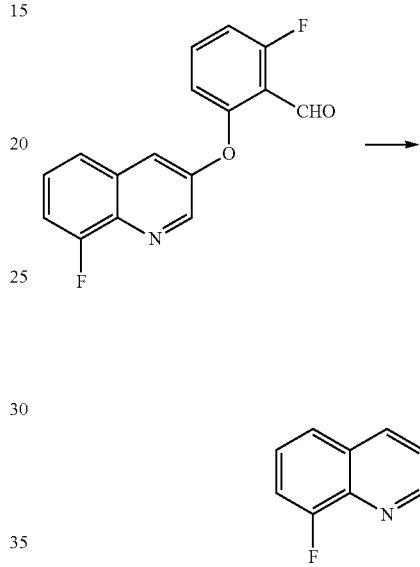

After 3.2 g of 2-fluoro-6-(8-fluoroquinolin-3-yloxy)-benzaldehyde was dissolved in 70 ml of dichloromethane and the resultant was cooled to 0° C., 1.3 g of titanium tetraisopropoxide was added. After the reaction solution was warmed to room temperature, 4.5 g of trimethylsilyl cyanide was added thereto, and the mixture was stirred for 2 hours. Dilute hydrochloric acid was added to the reaction solution and the solution was extracted with dichloromethane. The organic layer was concentrated and purified by silica gel column chromatography to obtain 3.1 g of [2-fluoro-6-(8-fluoroquinolin-3-yloxy)-phenyl]-trimethylsilyloxy-acetonitrile (approximately 90% purity).

Step 2) Synthesis of 1-[2-fluoro-6-(8-fluoroquinolin-3-yloxy)-phenyl]-1-hydroxy-propan-2-one

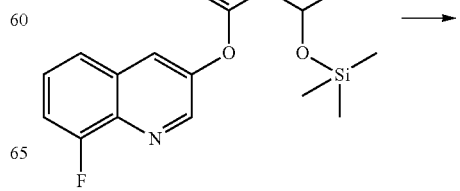

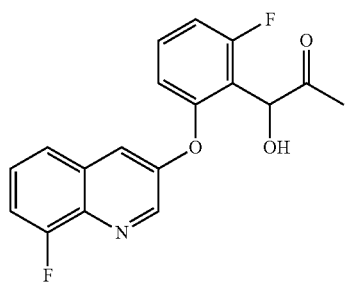

3.3 g of [2-fluoro-6-(8-fluoroquinolin-3-yloxy)-phenyl]-trimethylsilyloxy-acetonitrile (approximately 90% purity) was dissolved in 50 ml of diethyl ether and 5.7 ml of methylmagnesium bromide (3.0 M diethyl ether solution) was added dropwise at room temperature. After the mixture was stirred for 1 hour at room temperature, the resultant was heated under reflux for 3 hours, and then treated with dilute hydrochloric acid. The resultant was subjected to extraction with ethyl acetate, and then the organic layer was concentrated to obtain 3.9 g of crude product. 20 ml of 2N hydrochloric acid and 10 ml of tetrahydrofuran were added to 1.9 g of the crude product and the mixture was stirred for 4 hours at room temperature. The reaction solution was extracted with ethyl acetate and then purified by silica gel column chromatography to obtain 0.4 g of 1-[2-fluoro-6-(8-fluoroquinolin-3-yloxy)-phenyl]-1-hydroxy-propan-2-one.

Step 3) Synthesis of 1-[2-fluoro-6-(8-fluoroquinolin-3-yloxy)-phenyl]-propane-1,2-dione

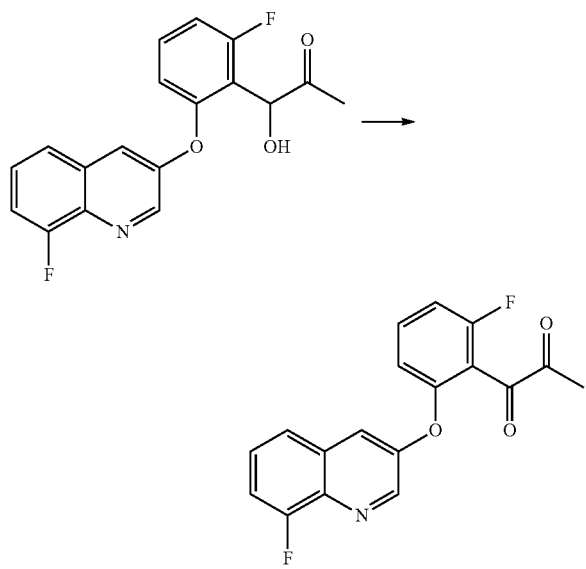

After 0.14 g of 1-[2-fluoro-6-(8-fluoroquinolin-3-yloxy)-phenyl]-1-hydroxy-propan-2-one was dissolved in 10 ml of dichloromethane, 0.91 g of Dess-Martin reagent was added thereto at 0° C. After 3 hours of stirring, the reaction solution was concentrated and purified by silica gel column chromatography to obtain 0.08 g of 1-[2-fluoro-6-(8-fluoroquinolin-3-yloxy)-phenyl]-propane-1,2-dione (Compound Number 396).

Example 24

Synthesis of 1-[2-fluoro-6-(8-fluoroquinolin-3-yloxy)-phenyl]-2-hydroxy-2-methyl-propan-1-one Step 1) Synthesis of 1-[2-fluoro-6-(8-fluoroquinolin-3-yloxy)-phenyl]-2-hydroxy-2-methyl-propane-1,2-diol

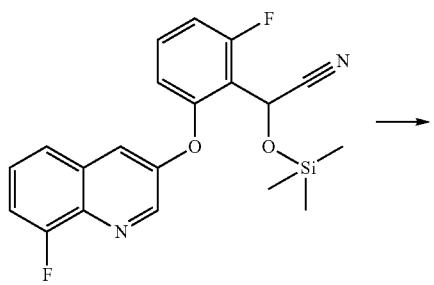

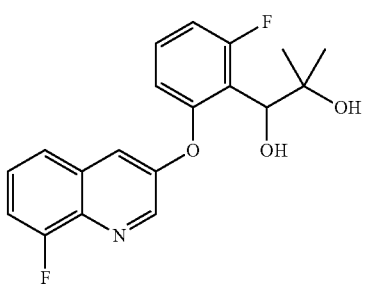

3.3 g of [2-fluoro-6-(8-fluoroquinolin-3-yloxy)-phenyl]-trimethylsilyloxy-acetonitrile was dissolved in 50 ml of diethyl ether and 5.7 ml of methylmagnesium bromide (3.0 M diethyl ether solution) was added dropwise at room temperature. After the mixture was stirred for 1 hour at room temperature, the resultant was heated under reflux for 3 hours, and then treated with dilute hydrochloric acid. The resultant was subjected to extraction with ethyl acetate and then the organic layer was concentrated to obtain 3.9 g of crude product. 1.9 g of the crude product was dissolved in 20 ml of tetrahydrofuran and 3.2 ml of methylmagnesium bromide (3.0 M diethyl ether solution) was added dropwise at 0° C. After 3 hours of stirring at 0° C., 20 ml of 2N hydrochloric acid was added and the mixture was stirred for one day at room temperature. The reaction solution was extracted with ethyl acetate and purified by silica gel column chromatography to obtain 0.25 g of 1-[2-fluoro-6-(8-fluoroquinolin-3-yloxy)-phenyl]-2-methyl-propane-1,2-diol as a crude product.

Step 2) Synthesis of 1-[2-fluoro-6-(8-fluoroquinolin-3-yloxy)-phenyl]-2-hydroxy-2-methyl-propan-1-one

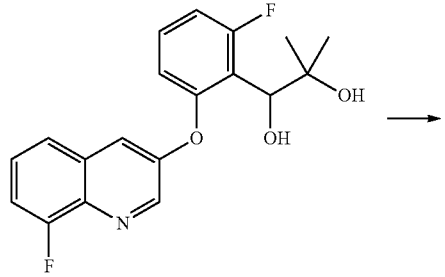

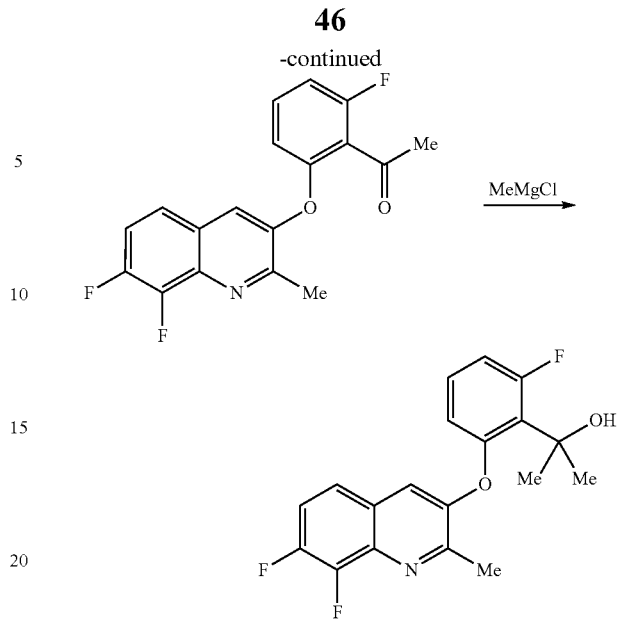

0.15 g of 1-[2-fluoro-6-(8-fluoroquinolin-3-yloxy)-phenyl]-2-methyl-propane-1,2-diol was dissolved in 10 ml of dichloromethane, and 0.20 g of Dess-Martin reagent was added thereto at 0° C. After 2 hours of stirring, the reaction solution was concentrated and purified by silica gel column chromatography to obtain 0.03 g of 1-[2-fluoro-6-(8-fluoroquinolin-3-yloxy)-phenyl]-2-hydroxy-2-methyl-propan-1-one (Compound Number 398).

Example 25

Synthesis of 2-[2-fluoro-6-(7,8-difluoro-2-methylquinolin-3-yloxy)phenyl]propan-2-ol

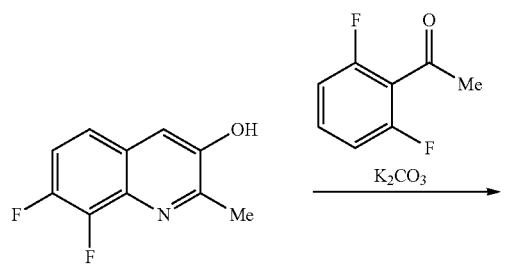

26.3 g of 7,8-difluoro-3-hydroxy-2-methylquinoline was dissolved in 200 mL of dimethylformamide. 27.2 g of 2,6-difluoroacetophenone and 24.0 g of potassium carbonate were added to the solution and the mixture was stirred for 4 hours at 100° C. After the thus obtained reaction solution was poured into ice water, and neutralized with dilute hydrochloric acid, the liquid was separated with ethyl acetate. The organic layer was concentrated and purified by silica gel column chromatography to obtain 17.0 g of 1-[2-fluoro-6-(7,8-difluoro-2-methylquinolin-3-yloxy)-phenyl]-ethanone.

After 11.0 g of 1-[2-fluoro-6-(7,8-difluoro-2-methylquinolin-3-yloxy)-phenyl]-ethanone obtained was dissolved in 80 ml of tetrahydrofuran and cooled to 0° C., 16.6 ml of methylmagnesium chloride (3.0 M tetrahydrofuran solution) was added dropwise. After the resultant was warmed to room temperature and stirred for 2 hours, the reaction solution was treated with dilute hydrochloric acid and the liquid was separated with ethyl acetate. The organic layer was concentrated and purified by silica gel column chromatography to obtain 10.0 g of 2-[2-fluoro-6-(7,8-difluoro-2-methylquinolin-3-yloxy)phenyl]propan-2-ol (Compound Number 125) was obtained.

Example 26

Synthesis of 2-[2-fluoro-6-(7,8-difluoroquinolin-3-yloxy)phenyl]propan-2-ol

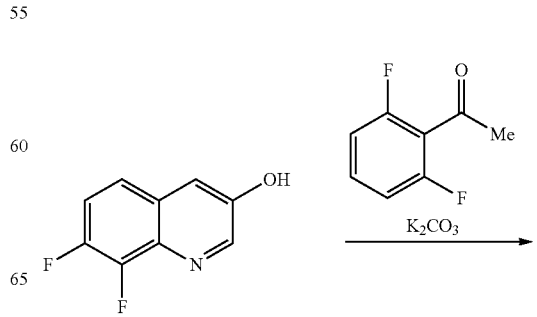

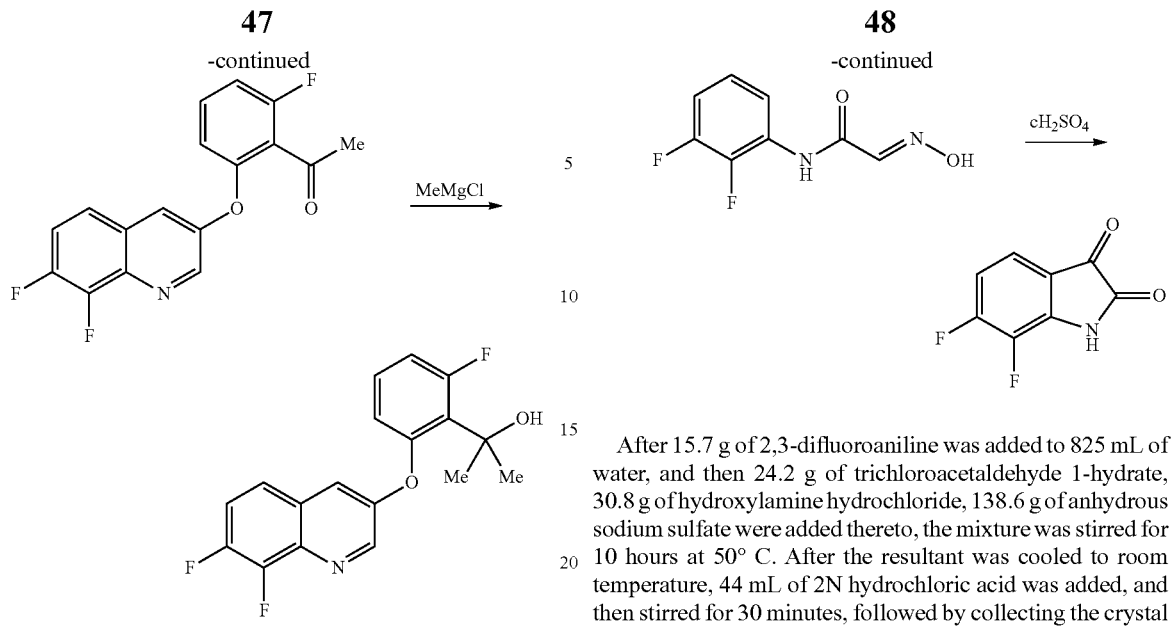

0.5 g of 7,8-difluoro-3-hydroxyquinoline was dissolved in 10 mL of dimethylformamide. 0.52 g of 2,6-difluoroacetophenone and 0.46 g of potassium carbonate were added to the solution, and the mixture was stirred for 2.5 hours at 100° C. The thus obtained reaction solution was poured into ice water and then neutralized with dilute hydrochloric acid, the liquid was separated with ethyl acetate. The organic layer was concentrated and purified by silica gel column chromatography to obtain 0.38 g of 1-[2-fluoro-6-(7,8-difluoroquinolin-3-yloxy)-phenyl]-ethanone (Compound Number 391).

After 0.38 g of 1-[2-fluoro-6-(7,8-difluoroquinolin-3-yloxy)-phenyl]-ethanone obtained was dissolved in 5 ml of tetrahydrofuran and cooled to 0° C., 1.4 ml of methylmagnesium bromide (3.0 M diethyl ether solution) was added dropwise. After the resultant was warmed to room temperature and stirred for 2 hours, the reaction solution was treated with dilute hydrochloric acid and the liquid was separated with ethyl acetate. The organic layer was concentrated and purified by silica gel column chromatography to obtain 0.33 g of 2-[2-fluoro-6-(7,8-difluoroquinolin-3-yloxy)phenyl]propan-2-ol (Compound Number 124).

Hereinafter, the intermediate product according to the present invention is described in more detail with reference to examples, however, the intermediate product according to the present invention is not in the least limited by the following examples.

Example 27

Synthesis of 7,8-difluoro-3-hydroxy-2-methylquinoline

Step 1) Synthesis of 6,7-difluoroisatin

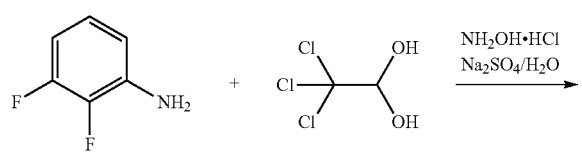

After 15.7 g of 2,3-difluoroaniline was added to 825 mL of water, and then 24.2 g of trichloroacetaldehyde 1-hydrate, 30.8 g of hydroxylamine hydrochloride, 138.6 g of anhydrous sodium sulfate were added thereto, the mixture was stirred for 10 hours at 50° C. After the resultant was cooled to room temperature, 44 mL of 2N hydrochloric acid was added, and then stirred for 30 minutes, followed by collecting the crystal by filtration. After the thus obtained crystals were dried, and then added to concentrated sulfuric acid heated to 70° C., the mixture was stirred for 1 hour at 80 to 90° C. The reaction solution was poured into ice, followed by subjecting to extraction with ethyl acetate, and then washing with saturated saline solution. After the organic layer was dried with magnesium sulfate, the solvent was evaporated under reduced pressure to obtain 26 g of a crude product of 6,7-difluoroisatin.

Step 2) Synthesis of 7,8-difluoro-3-hydroxy-2-methylquinoline

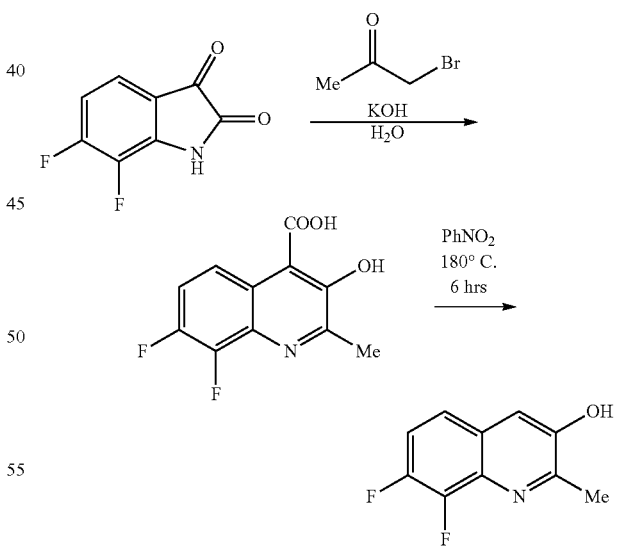

After 41 g of the crude product of 6,7-difluoroisatin was added to 200 mL of water, 75.3 g of potassium hydroxide (6 equivalents) was added thereto under ice-cooling and the mixture was stirred for 30 minutes. 42 g of bromoacetophenone (1.4 equivalents) was added dropwise to the suspension while maintaining the internal temperature of the reaction solution at 20 to 25° C., and the mixture was further stirred overnight at room temperature. After the resultant was neutralized with concentrated hydrochloric acid, the precipitated crystals were collected by filtration and washed with a small amount of water. The thus obtained crystals were sufficiently dried, and then added little by little to 100 mL of nitrobenzene heated to 130 to 140° C., and the mixture was stirred further for 1 hour at 150° C. After the reaction solution was cooled to room temperature, the precipitated crystals were washed with chloroform to obtain 26.3 g of 7,8-difluoro-3-hydroxy-2-methylquinoline.

$^1$H NMR (300 MHz, DMSO-d6) δ 2.57 (s, 3H), 7.4 to 7.7 (m, 3H), 10.60 (bs, 1H).

The following compound was produced using the same method.

8-fluoro-3-hydroxy-2-methylquinoline $^1$H NMR (300 MHz, DMSO-d6) δ 2.56 (s, 3H), 7.2 to 7.6 (m, 4H), 10.53 (bs, Example 28

Synthesis of 7,8-difluoro-3-hydroxyquinoline

Step 1) Synthesis of 7,8-difluoroquinoline

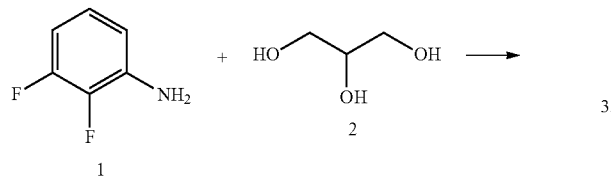

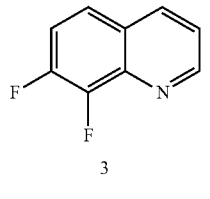

In a 3 L eggplant-shaped flask containing a stir bar, 80% sulfuric acid (607.7 g, 49.57 mol) was introduced and cooled to 0° C., and then 2,3-difluoroaniline (160.0 g, 1.24 mol) was slowly added. After the addition, the mixture was stirred for 1 hour at room temperature, sodium iodide (1.85 g, 12.3 mmol) was further added thereto, and then the mixture was heated in an oil bath until the temperature thereof reached 150° C. (temperature of the bath). When it reached this temperature, glycerin (125.5 g, 1.36 mol) was added dropwise over a period of one hour, and the mixture was stirred for 1 hour at 150° C. The temperature of the bath was further elevated to 180° C., and the water was evaporated over a period of 2 hours using a distillation apparatus. After confirming that the starting material had disappeared, the mixture was neutralized using 10N aqueous sodium hydroxide while cooling with an ice-water bath (the inner temperature is 60 to 70° C.). After the neutralization, before the inner temperature returned to room temperature, the resultant was subjected to extraction with ethyl acetate, and the extract was dried with magnesium sulfate, filtered, and concentrated. The thus obtained crude product was purified by silica gel column chromatography (normal hexane:ethyl acetate) to obtain 185.5 g of 7,8-difluoroquinoline (91%) as a hazel solid.

Step 2) Synthesis of 7,8-difluoro-3-iodoquinoline

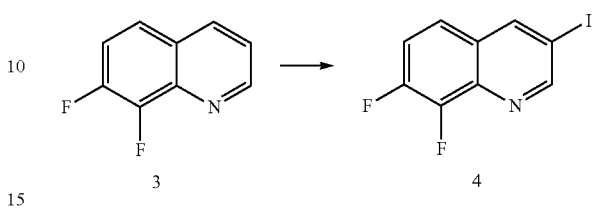

In a 3 L eggplant-shaped flask containing a stir bar, 7,8-difluoroquinoline (185.5 g, 1.12 mol), N-iodosuccinimide (505.4 g, 2.25 mol), and acetic acid (927 mL) were introduced and the mixture was stirred for 30 hours at 90° C. After cooling, the precipitated crystals was filtered and dried. On the other hand, the filtrate was concentrated under reduced pressure, the residual acetic acid was neutralized with sodium hydrogen carbonate, and the resultant was subjected to extraction with ethyl acetate. In addition, after the filtrate was dried with magnesium sulfate, filtered and concentrated, the thus obtained crude product was purified by silica gel column chromatography (normal hexane:ethyl acetate) to obtain 227.2 g (70%) of 7,8-difluoro-3-iodoquinoline was obtained as a hazel solid combined with the previously obtained crystals.

$^1$H-NMR (300 MHz, CDCl$_3$) δ 7.39 to 7.51 (m, 2H), 8.55 (m, 1H), 9.08 (d, 1H, J=2.1 Hz).

Step 3) Synthesis of 7,8-difluoro-3-hydroxyquinoline

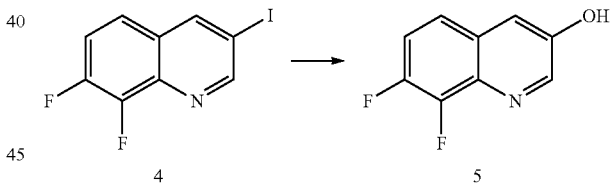

In a 3 L eggplant-shaped flask containing a stir bar, 7,8-difluoro-3-iodoquinoline (227.2 g, 0.78 mol), dimethylsulfoxide (600 mL), and water (600 mL) were introduced and sodium hydroxide (131.5 g, 2.34 mol), CuI (14.8 g, 0.078 mol), and 1,10-phenanthroline (28.1 g, 0.156 mol) were added. The mixture was further heated to 100° C. in an oil bath and was stirred for 24 hours. After cooling, the organic layer was removed by adding ethyl acetate and water. The thus obtained aqueous layer was neutralized with concentrated hydrochloric acid, and then the precipitated crystals were filtered and dried. On the other hand, after the filtrate was extracted with ethyl acetate, dried with magnesium sulfate, filtered and concentrated, the crude product obtained was purified by silica gel column chromatography (normal hexane:ethyl acetate) to obtain 133.7 g (95%) of 7,8-difluoro-3-hydroxyquinoline as a hazel solid combined with the previously obtained crystals.

$^1$H-NMR (300 MHz, CD$_3$OD) δ 7.39 to 7.60 (m, 3H), 8.59 (d, 1H, J=2.4 Hz).

The following compound was produced using the same method.

8-fluoro-3-hydroxyquinoline $^1$H-NMR (300 MHz, CDCl$_3$) δ 7.16 (m, 1H) δ 7.34 to 7.49 (m, 3H), 8.71 (d, 1H, J=2.7 Hz), 9.90 (bs, 1H).

The nitrogen-containing heterocyclic compounds obtained from the above examples are shown in Tables 1 to 19. In addition, compounds synthesized in the same manner as that of any of the above examples are further shown in Table 20 to Table 28. Also, Et represents an ethyl group, $^n$Pr represents an n-propyl group, $^i$Pr represents an i-propyl group, $^c$Pr represents a cyclopropyl group, $^n$Bu represents an n-butyl group, $^t$Bu represents a t-butyl group, Ph represents a phenyl group, Bn represents a benzyl group, and Tos represents toluene sulfonyl group. $^1$H-NMR of the compounds in each table is also shown in Table 29 to Table 41.

TABLE 1

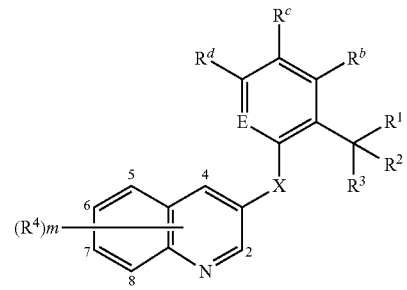

| Compound No. | (R$^4$)$_m$ | R$^1$ | R$^2$ | R$^3$ | R$^b$ | R$^c$ | R$^d$ | E | —X— | Physical property |
|---|---|---|---|---|---|---|---|---|---|---|
| 1 | — | | =O | —CH$_3$ | H | H | H | CH | —O— | 75-76 |
| 2 | — | | =O | —H | H | H | H | CH | —O— | 76-79 |
| 3 | — | | =O | —OEt | H | H | H | CH | —O— | amorphous |
| 4 | — | | =O | —OEt | H | H | H | OF | —O— | 72-74 |
| 5 | — | | =O | —OEt | H | H | F | CH | —O— | amorphous |
| 6 | — | | =O | —OEt | H | F | H | CH | —O— | 93-95 |
| 7 | — | | =O | —OEt | F | H | H | CH | —O— | amorphous |
| 8 | 8-F | | =O | —OEt | F | H | H | CH | —O— | amorphous |
| 9 | — | —F | —F | —F | H | H | H | CH | —O— | amorphous |
| 10 | 8-F | | =O | —CH$_3$ | F | H | H | CH | —O— | amorphous |
| 11 | — | | =O | —$^t$Bu | H | H | H | CH | —O— | amorphous |
| 12 | 8-F | | =O | —$^t$Bu | F | H | H | CH | —O— | amorphous |
| 13 | — | —F | —F | —F | H | H | H | N | —O— | amorphous |
| 14 | — | —CH$_3$ | —CH$_3$ | —CH$_3$ | H | H | H | CH | —O— | amorphous |
| 15 | 8-F | —CH$_3$ | —CH$_3$ | —CH$_3$ | H | H | H | CH | —O— | 77-79 |
| 16 | — | —CH$_3$ | —CH$_3$ | —(CH$_2$)$_2$— | H | H | CH | —O— | 90-94 |

TABLE 2

| Compound No. | (R$^4$)$_m$ | R$^1$ | R$^2$ | R$^3$ | R$^b$ | R$^c$ | R$^d$ | E | —X— | Physical property |
|---|---|---|---|---|---|---|---|---|---|---|
| 17 | — | —CH$_3$ | —CH$_3$ | —Et | H | H | H | CH | —O— | amorphous |
| 18 | 8-F | —CH$_3$ | —CH$_3$ | —Et | H | H | H | CH | —O— | amorphous |
| 19 | 8-F | —CH$_3$ | —CH$_3$ | —(CH$_2$)$_2$— | H | H | CH | —O— | 104-106 |
| 20 | — | | =O | —NH$_2$ | Cl | H | H | CH | —O— | 168-188 |
| 21 | — | | =O | —NH$_2$ | Br | H | H | CH | —O— | 204-206 |
| 22 | — | | =O | —N(CH$_3$)$_2$ | Br | H | H | CH | —O— | amorphous |
| 23 | — | | =N—OH | —CH$_3$ | H | H | H | CH | —O— | 125-126 |
| 24 | — | | =N—OCH$_3$ | —CH$_3$ | H | H | H | CH | —O— | amorphous |
| 25 | — | | =N—O$^t$Bu | —CH$_3$ | H | H | H | CH | —O— | amorphous |
| 26 | 8-F | | =N—OH | —CH$_3$ | F | H | H | CH | —O— | 171-173 |
| 27 | — | —OCH$_3$ | —CH$_3$ | —OCH$_3$ | H | H | H | CH | —O— | amorphous |
| 28 | — | —OSi(CH$_3$)$_3$ | —CH$_3$ | —CF$_3$ | H | H | H | CH | —O— | amorphous |
| 29 | — | —OH | —CH$_3$ | —CF$_3$ | H | H | H | CH | —O— | 158-160 |
| 30 | 8-F | —OH | —CH$_3$ | —$^t$Bu | F | H | H | CH | —O— | amorphous |
| 31 | — | —OH | —CH$_3$ | —$^t$Bu | H | H | H | CH | —O— | amorphous |
| 32 | — | —OH | —CH$_3$ | —Et | H | H | H | CH | —O— | 129-131 |
| 33 | 8-F | —OH | —CH$_3$ | —Et | H | H | H | CH | —O— | 122-124 |
| 34 | 8-F | —OH | —CH$_3$ | —(CH$_2$)$_2$— | H | H | CH | —O— | amorphous |
| 35 | 8-F | —OH | —$^t$Bu | —(CH$_2$)$_2$— | H | H | CH | —O— | amorphous |
| 36 | 8-F | —OH | —CH$_3$ | —CH$_3$ | F | H | H | CH | —O— | amorphous |
| 37 | 2-CH$_3$, 8-F | —OH | —CH$_3$ | —CH$_3$ | F | H | H | CH | —O— | amorphous |
| 38 | — | —OH | —CH$_3$ | —CH$_3$ | H | H | H | CH | —O— | amorphous |
| 39 | 2-$^t$Bu | | =O | —H | H | H | H | CH | —O— | amorphous |
| 40 | — | —OH | —CH$_3$ | —CH$_3$ | H | H | H | CF | —O— | amorphous |

TABLE 2-continued

| Compound No. | $(R^4)_m$ | $R^1$ | $R^2$ | $R^3$ | $R^b$ | $R^c$ | $R^d$ | E | —X— | Physical property |
|---|---|---|---|---|---|---|---|---|---|---|
| 41 | — | —OH | —CH$_3$ | —CH$_3$ | H | H | F | CH | —O— | amorphous |
| 42 | — | —OH | —CH$_3$ | —CH$_3$ | H | F | H | CH | —O— | amorphous |

TABLE 3

| Compound No. | $(R^4)_m$ | $R^1$ | $R^2$ | $R^3$ | $R^b$ | $R^c$ | $R^d$ | E | —X— | Physical property |
|---|---|---|---|---|---|---|---|---|---|---|
| 43 | — | —OH | —CH$_3$ | —CH$_3$ | F | H | H | CH | —O— | amorphous |
| 44 | 8-F | —OH | —CH$_3$ | —CH$_3$ | H | H | H | CH | —O— | 128-130 |
| 45 | — | —OH | —CH$_3$ | —CH$_3$ | H | H | H | N | —O— | 146-147 |
| 46 | 2-Et | —OH | —CH$_3$ | —CH$_3$ | H | H | H | CH | —O— | amorphous |
| 47 | 2-$^n$Bu | —OH | —CH$_3$ | —CH$_3$ | H | H | H | CH | —O— | amorphous |
| 48 | 8-F | —OH | —CH$_3$ | —Et | F | H | H | CH | —O— | amorphous |
| 49 | 8-Cl | —OH | —CH$_3$ | —CH$_3$ | F | H | H | CH | —O— | amorphous |
| 50 | — | =O | | —(CH$_2$)$_2$— | H | H | CH | —NH— | 130-132 |
| 51 | — | =O | | —Ph | H | H | H | CH | —NH— | amorphous |
| 52 | 8-F | —CH$_3$ | —CH$_3$ | —CH$_3$ | H | H | H | CH | —CH$_2$— | 108-111 |
| 53 | 8-F | =O | | —OEt | F | H | H | CH | —CH$_2$— | amorphous |
| 54 | 8-F | —CH$_3$ | —CH$_3$ | —CH$_3$ | H | H | H | CH | —CH(OH)— | 173-175 |
| 55 | — | —CH$_3$ | —CH$_3$ | —CH$_2$—OSi(CH$_3$)$_2$—$^t$Bu | H | H | H | CH | —CH(OH)— | 140-143 |
| 56 | — | —CH$_3$ | —CH$_3$ | —C(CH$_3$)$_2$—CH$_2$OH | H | H | H | CH | —CH(OH)— | 136-138 |
| 57 | 8-F | —CH$_3$ | —CH$_3$ | —CH$_3$ | H | H | H | CH | —CO— | 182-183 |
| 58 | — | —CH$_3$ | —CH$_3$ | —CH$_2$—OSi(CH$_3$)$_2$—$^t$Bu | H | H | H | CH | —CO— | 105-108 |
| 59 | — | —CH$_3$ | —CH$_3$ | —CH$_2$O-Tos | H | H | H | CH | —CO— | amorphous |
| 60 | 2-Cl | —CH$_3$ | —CH$_3$ | —(CH$_2$)$_2$— | H | H | CH | —O— | amorphous |
| 61 | 1-Oxide, 8-F | —CH$_3$ | —CH$_3$ | —Et | H | H | H | CH | —O— | amorphous |
| 62 | — | ≡N | | | H | H | H | CH | —O— | 92-95 |
| 63 | — | ≡N | | | F | H | H | CH | —O— | 149-151 |
| 64 | — | ≡N | | | Br | H | H | CH | —O— | 167-169 |
| 65 | — | ≡N | | | Cl | H | H | CH | —O— | 150-151 |
| 66 | — | ≡N | | | OMe | H | H | CH | —O— | 120-122 |

TABLE 4

| Compound No. | $(R^4)_m$ | $R^1$ | $R^2$ | $R^3$ | $R^b$ | $R^c$ | $R^d$ | E | —X— | Physical property |
|---|---|---|---|---|---|---|---|---|---|---|
| 67 | 2-CH$_3$ | —OH | —CH$_3$ | —CH$_3$ | H | H | H | CH | —O— | amorphous |
| 68 | 2-$^i$Pr | —OH | —CH$_3$ | —CH$_3$ | H | H | H | CH | —O— | amorphous |
| 69 | 2-OCH$_3$ | —OH | —CH$_3$ | —CH$_3$ | H | H | H | CH | —O— | amorphous |
| 70 | 2-OEt | —OH | —CH$_3$ | —CH$_3$ | H | H | H | CH | —O— | amorphous |
| 71 | 1-Oxide | —OH | —CH$_3$ | —CH$_3$ | H | H | H | CH | —O— | 154-155 |
| 72 | — | —OH | —CH$_3$ | —C(CH$_3$)$_2$OH | H | H | H | CH | —O— | amorphous |
| 73 | — | —OH | —CH$_3$ | —CO$_2$Et | H | H | H | CH | —O— | amorphous |
| 74 | 8-F | —OH | —CH$_3$ | —Ph | F | H | H | CH | —O— | amorphous |
| 75 | 8-F | —OH | —CH$_3$ | —CH$_2$Ph | F | H | H | CH | —O— | amorphous |
| 76 | 8-F | —OH | —CH$_3$ | —CH=CH$_2$ | F | H | H | CH | —O— | amorphous |
| 77 | 8-F | —OH | —CH$_3$ | —CH$_2$—CH=CH$_2$ | F | H | H | CH | —O— | amorphous |
| 78 | 2-CH=CH$_2$, 8-F | —OH | —CH$_3$ | —CH=CH$_2$ | F | H | H | CH | —O— | amorphous |
| 79 | 2-CH$_2$CH=CH$_2$, 8-F | —OH | —CH$_3$ | —CH$_2$—CH=CH$_2$ | F | H | H | CH | —O— | amorphous |
| 80 | 8-F | —OH | —CH$_3$ | —$^i$Pr | F | H | H | CH | —O— | amorphous |
| 81 | 8-F | —OH | —CH$_3$ | —C(CH$_3$)=CH$_2$ | F | H | H | CH | —O— | amorphous |
| 82 | 8-F | —OH | —CH$_3$ | —CH$_2$—(4-FPh) | F | H | H | CH | —O— | amorphous |
| 83 | 8-F | —OH | —CH$_3$ | —CH(CH$_3$)—CH=CH$_2$ | F | H | H | CH | —O— | amorphous |
| 84 | 8-F | —OH | —CH$_3$ | —CH$_3$ | F | H | H | CF | —O— | 149-150 |
| 85 | 2-CH$_3$, 8-F | —OH | —CH$_3$ | —CH$_3$ | F | H | H | CF | —O— | 111-113 |
| 86 | 8-F | —OH | —CH$_3$ | —$^c$Pr | F | H | H | CH | —O— | amorphous |
| 87 | 2-$^c$Pr, 8-F | —OH | —CH$_3$ | —$^c$Pr | F | H | H | CH | —O— | amorphous |
| 88 | 2-CH$_3$, 8-F | —OH | —CH$_3$ | —Et | F | H | H | CH | —O— | amorphous |
| 89 | 2-CH$_3$, 8-F | —OH | —CH$_3$ | —CH=CH$_2$ | F | H | H | CH | —O— | amorphous |
| 90 | 2-CH$_3$, 8-F | —OH | —CH$_3$ | —$^c$Pr | F | H | H | CH | —O— | amorphous |
| 91 | 2-CH$_3$, 8-F | —OH | —CH$_3$ | —CH$_2$—(4-CH$_3$OPh) | F | H | H | CH | —O— | amorphous |
| 92 | 2-CH$_3$, 8-F | —OH | —CH$_3$ | —CH$_2$—(4-FPh) | F | H | H | CH | —O— | amorphous |

TABLE 5

| Compound No. | $(R^4)_m$ | $R^1$ | $R^2$ | $R^3$ | $R^b$ | $R^c$ | $R^d$ | E | —X— | Physical property |
|---|---|---|---|---|---|---|---|---|---|---|
| 93 | 2-CH₃, 8-Cl | —OH | —CH₃ | —CH₃ | F | H | H | CH | —O— | 96-98 |
| 94 | 2,8-(CH₃)₂ | —OH | —CH₃ | —CH₃ | F | H | H | CH | —O— | amorphous |
| 95 | 8-F | —OH | —CH₃ | —CH₃ | Cl | H | H | CH | —O— | 120-123 |
| 96 | 8-F | —OH | —CH₃ | —Et | Cl | H | H | CH | —O— | 39-42 |
| 97 | 2-CH₃, 8-F | —OH | —CH₃ | —CH₃ | Cl | H | H | CH | —O— | amorphous |
| 98 | 8-F | —OH | —CH₃ | —CH₃ | Br | H | H | CH | —O— | 107-110 |
| 99 | 8-F | —OH | —CH₃ | —CH₃ | H | Cl | H | CH | —O— | 124-126 |
| 100 | 2-CH₃, 8-F | —OH | —CH₃ | —CH₃ | Br | H | H | CH | —O— | 93-94 |
| 101 | 8-F | —OH | —CH₃ | —CH₃ | H | CH₃ | H | CH | —O— | amorphous |
| 102 | 8-F | —OH | —CH₃ | —CH₃ | Cl | F | H | CH | —O— | 135-137 |
| 103 | — | —OH | —CH₃ | —CH₃ | Cl | H | H | CH | —O— | amorphous |
| 104 | 8-F | —OH | —CH₃ | —CH₃ | H | F | H | CH | —O— | 122-124 |
| 105 | 2-CH₃, 6-F | —OH | —CH₃ | —CH₃ | F | H | H | CH | —O— | amorphous |
| 106 | 2-CH₃, 7-F | —OH | —CH₃ | —CH₃ | F | H | H | CH | —O— | 98-100 |
| 107 | 2-CH₃ | —OH | —CH₃ | —CH₃ | F | H | H | CH | —O— | amorphous |
| 108 | 2-CH₃ | —OH | —CH₃ | —CH₃ | Cl | H | H | CH | —O— | amorphous |
| 109 | — | —OCH₃ | —CH₃ | —CH₃ | F | H | H | CH | —O— | 93-94 |
| 110 | 2-CH₃, 8-F | —OH | —CH₃ | —CH₃ | Cl | F | H | CH | —O— | 138-140 |
| 111 | — | —OH | —CH₃ | —CF₃ | F | H | H | CH | —O— | amorphous |
| 112 | — | —OH | —CF₃ | —CF₃ | H | H | H | CH | —O— | 170-172 |
| 113 | — | —OSi(CH₃)₃ | —CF₃ | —CF₃ | F | H | H | CH | —O— | amorphous |
| 114 | — | —OH | —CF₃ | —CF₃ | F | H | H | CH | —O— | 130-132 |
| 115 | — | —OH | —CH₃ | —CH₃ | Cl | F | H | CH | —O— | 115-116 |
| 116 | 5,8-F₂ | —OH | —CH₃ | —CH₃ | F | H | H | CH | —O— | 154-155 |
| 117 | 2-CH₃, 5,8-F₂ | —OH | —CH₃ | —CH₃ | F | H | H | CH | —O— | 124-126 |
| 118 | 2-CH₃, 7-Cl | —OH | —CH₃ | —CH₃ | F | H | H | CH | —O— | amorphous |

TABLE 6

| Compound No. | $(R^4)_m$ | $R^1$ | $R^2$ | $R^3$ | $R^b$ | $R^c$ | $R^d$ | E | —X— | Physical property |
|---|---|---|---|---|---|---|---|---|---|---|
| 119 | — | —OH | —CH₃ | —CH₃ | F | F | H | CH | —O— | amorphous |
| 120 | 5-F | —OH | —CH₃ | —CH₃ | F | H | H | CH | —O— | 90-92 |
| 121 | 2-CH₃, 5-F | —OH | —CH₃ | —CH₃ | F | H | H | CH | —O— | 95-97 |
| 122 | 8-F | —OH | —CF₃ | —CF₃ | F | H | H | CH | —O— | 151-153 |
| 123 | 8-F | —OH | —CH₃ | —CH₃ | F | CH₃ | H | CH | —O— | 118-120 |
| 124 | 7,8-F₂ | —OH | —CH₃ | —CH₃ | F | H | H | CH | —O— | 78-80 |
| 125 | 2-CH₃, 7,8-F₂ | —OH | —CH₃ | —CH₃ | F | H | H | CH | —O— | 108-110 |
| 126 | 7-F | —OH | —CH₃ | —CH₃ | F | H | H | CH | —O— | amorphous |
| 127 | 2-CH₃, 4,8-F₂ | —OH | —CH₃ | —CH₃ | F | H | H | CH | —O— | 130-132 |
| 128 | 2-CH₃, 7-F | —OH | —CH₃ | —Et | F | H | H | CH | —O— | $n_D^{20.7}$1.5580 |
| 129 | 8-F | —OSi(CH₃)₃ | —CH₃ | —CN | F | H | H | CH | —O— | |
| 130 | 8-F | —OH | —CH₃ | —COCH₃ | F | H | H | CH | —O— | |
| 131 | — | —OCH₃ | —H | —(CH₂)₂— | | H | H | CH | —O— | amorphous |
| 132 | — | —OCH₃ | —H | —CH₃ | H | H | H | CH | —O— | amorphous |
| 133 | — | —OEt | —H | —(CH₂)₂— | | H | H | CH | —O— | amorphous |
| 134 | — | —OⁿPr | —H | —(CH₂)₂— | | H | H | CH | —O— | amorphous |
| 135 | — | —OⁿBu | —H | —CH₃ | H | H | H | CH | —O— | amorphous |
| 136 | — | —OH | —H | —ᵗBu | H | H | H | CH | —O— | amorphous |
| 137 | — | —OH | —H | —(CH₂)₂— | | H | H | CH | —O— | amorphous |
| 138 | 8-F | —OH | —H | —CH₃ | F | H | H | CH | —O— | 149-151 |
| 139 | 2-CH₃, 8-F | —OH | —H | —ᵗBu | F | H | H | CH | —O— | 104-106 |
| 140 | 8-F | —OCH₃ | —H | —CH₃ | F | H | H | CH | —O— | amorphous |
| 141 | 8-F | —OH | —H | —CH₃ | Cl | F | H | CH | —O— | 139-141 |
| 142 | 8-F | —OCH₃ | —H | —CH₃ | Cl | F | H | CH | —O— | amorphous |
| 143 | 8-F | —OH | —H | —ᶜPr | Cl | H | H | CH | —O— | amorphous |
| 144 | 8-F | —OH | —H | —C(CH₃)=CH₂ | Cl | H | H | CH | —O— | 103-104 |

TABLE 7

| Compound No. | $(R^4)_m$ | $R^1$ | $R^2$ | $R^3$ | $R^b$ | $R^c$ | $R^d$ | E | —X— | Physical property |
|---|---|---|---|---|---|---|---|---|---|---|
| 145 | 8-F | —OH | —H | —ᵗBu | Cl | H | H | CH | —O— | amorphous |
| 146 | 8-F | —OH | —H | —CH₃ | Cl | H | H | CH | —O— | amorphous |
| 147 | 8-F | —OCH₃ | —H | —CH₃ | Cl | H | H | CH | —O— | amorphous |
| 148 | 8-F | —OH | —H | —CH₃ | Br | H | H | CH | —O— | amorphous |
| 149 | 8-F | —OCH₃ | —H | —CH₃ | Br | H | H | CH | —O— | amorphous |
| 150 | 8-F | —OCH₃ | —H | —CH₃ | CH₃ | H | H | CH | —O— | amorphous |
| 151 | 2-CH₃, 8-F | —OH | —H | —CH₃ | Cl | H | H | CH | —O— | 112-114 |
| 152 | 2-CH₃, 8-F | —OCH₃ | —H | —CH₃ | Cl | H | H | CH | —O— | amorphous |

TABLE 7-continued

| Compound No. | $(R^4)_m$ | $R^1$ | $R^2$ | $R^3$ | $R^b$ | $R^c$ | $R^d$ | E | —X— | Physical property |
|---|---|---|---|---|---|---|---|---|---|---|
| 153 | 8-F | —OCH$_3$ | —H | —CH$_3$ | CN | H | H | CH | —O— | amorphous |
| 154 | 8-OCH$_3$ | —OCH$_3$ | —H | —CH$_3$ | Br | H | H | CH | —O— | amorphous |
| 155 | 8-OCH$_3$ | —OCH$_3$ | —H | —CH$_3$ | OCH$_3$ | H | H | CH | —O— | amorphous |
| 156 | 8-F | —OCH$_2$CH=CH$_2$ | —H | —CH$_3$ | Cl | H | H | CH | —O— | amorphous |
| 157 | 8-F | —OH | —H | —Et | Cl | H | H | CH | —O— | amorphous |
| 158 | 8-F | —OSi(CH$_3$)$_3$ | —H | —CF$_3$ | Cl | H | H | CH | —O— | 115-117 |
| 159 | 8-F | —OH | —H | —CF$_3$ | Cl | H | H | CH | —O— | 174-176 |
| 160 | 8-F | —OCH$_2$Ph | —H | —CH$_3$ | Cl | H | H | CH | —O— | amorphous |
| 161 | 8-F | —OH | —H | —Ph | Cl | H | H | CH | —O— | amorphous |
| 162 | 8-F | —OH | —H | —CH=CH$_2$ | Cl | H | H | CH | —O— | 98-100 |
| 163 | 8-F | —OH | —H | —$^n$Bu | Cl | H | H | CH | —O— | amorphous |
| 164 | 8-F | —OH | —H | —C≡CH | Cl | H | H | CH | —O— | amorphous |
| 165 | 8-F | —OSi(CH$_3$)$_3$ | —H | —CN | Cl | H | H | CH | —O— | amorphous |
| 166 | 8-F | —OH | —H | —CH$_3$ | NO$_2$ | H | H | CH | —O— | 112-114 |
| 167 | 8-F | —OCH$_3$ | —H | —CH$_3$ | NO$_2$ | H | H | CH | —O— | amorphous |
| 168 | 8-F | —OCH$_3$ | —H | —CO$_2$CH$_3$ | Cl | H | H | CH | —O— | amorphous |
| 169 | 8-F | —OH | —H | —CN | Cl | H | H | CH | —O— | 174-175 |
| 170 | 8-F | —OSi(CH$_3$)$_3$ | —H | —COCH$_3$ | Cl | H | H | CH | —O— | amorphous |

TABLE 8

| Compound No. | $(R^4)_m$ | $R^1$ | $R^2$ | $R^3$ | $R^b$ | $R^c$ | $R^d$ | E | —X— | Physical property |
|---|---|---|---|---|---|---|---|---|---|---|
| 171 | 8-F | —OH | —H | —COCH$_3$ | Cl | H | H | CH | —O— | amorphous |
| 172 | 8-F | —OCH$_3$ | —H | —COCH$_3$ | Cl | H | H | CH | —O— | amorphous |
| 173 | 8-F | —OH | —H | —C(CH$_3$)$_2$OH | Cl | H | H | CH | —O— | amorphous |
| 174 | 8-F | —OH | —H | —CH$_2$Ph | Cl | H | H | CH | —O— | amorphous |
| 175 | 8-F | —OCH$_3$ | —H | —CH$_2$Ph | Cl | H | H | CH | —O— | amorphous |
| 176 | 8-F | —OH | —H | —CH$_3$ | Br | F | H | CH | —O— | 148-150 |
| 177 | 8-F | —OCH$_3$ | —H | —CH$_3$ | Br | F | H | CH | —O— | amorphous |
| 178 | 2-CH$_3$, 8-F | —OH | —H | —CH$_3$ | Cl | F | H | CH | —O— | 130-131 |
| 179 | 2-CH$_3$, 8-F | —OH | —H | —CH$_3$ | Br | F | H | CH | —O— | 119-121 |
| 180 | 8-F | —OCH$_3$ | —H | —C(CH$_3$)$_2$OH | Cl | H | H | CH | —O— | amorphous |
| 181 | 8-F | —OH | —H | —CO$_2$CH$_3$ | Cl | H | H | CH | —O— | amorphous |
| 182 | 8-F | —OH | —H | —CH$_2$CN | Cl | H | H | CH | —O— | 123-125 |
| 183 | 2-CH$_3$, 8-F | —OCH$_3$ | —H | —CH$_3$ | Cl | F | H | CH | —O— | 124-126 |
| 184 | 2-CH$_3$, 8-F | —OCH$_3$ | —H | —CH$_3$ | Br | F | H | CH | —O— | 108-110 |
| 185 | 8-F | —OH | —H | —CH$_3$ | CF$_3$ | H | H | CH | —O— | amorphous |
| 186 | 8-F | —OCH$_3$ | —H | —CH$_3$ | CF$_3$ | H | H | CH | —O— | amorphous |
| 187 | — | —OH | —H | —CH$_3$ | Cl | H | H | CH | —O— | 77-80 |
| 188 | — | —OCH$_3$ | —H | —CH$_3$ | Cl | H | H | CH | —O— | amorphous |
| 189 | — | —OH | —H | —CH$_3$ | H | H | H | CF | —O— | amorphous |
| 190 | — | —OH | —H | —CH$_3$ | Cl | H | H | CF | —O— | amorphous |
| 191 | — | —OH | —H | —CF$_3$ | H | H | H | CH | —O— | 157-159 |
| 192 | — | —OH | —H | —CH$_3$ | Cl | F | H | CH | —O— | 133-135 |
| 193 | — | —OH | —H | —CF$_3$ | F | H | H | CH | —O— | 129-131 |
| 194 | 5,8-F$_2$ | —OH | —H | —CH$_3$ | F | H | H | CH | —O— | 115-116 |
| 195 | 5-F | —OH | —H | —CH$_3$ | F | H | H | CH | —O— | 114-115 |
| 196 | 8-F | —OH | —H | —CF$_3$ | F | H | H | CH | —O— | 100-101 |

TABLE 9

| Compound No. | $(R^4)_m$ | $R^1$ | $R^2$ | $R^3$ | $R^b$ | $R^c$ | $R^d$ | E | —X— | Physical property |
|---|---|---|---|---|---|---|---|---|---|---|
| 197 | 7,8-F$_2$ | —OH | —H | —CH$_3$ | Cl | H | H | CH | —O— | 99-102 |
| 198 | 7,8-F$_2$ | —OCH$_3$ | —H | —CH$_3$ | Cl | H | H | CH | —O— | amorphous |
| 199 | 2-CH$_3$, 7,8-F$_2$ | —OH | —H | —CH$_3$ | Cl | H | H | CH | —O— | 135-136 |
| 200 | 2-CH$_3$, 7,8-F$_2$ | —OCH$_3$ | —H | —CH$_3$ | Cl | H | H | CH | —O— | 127-129 |
| 201 | 7-F | —OH | —H | —CH$_3$ | Cl | H | H | CH | —O— | 92-94 |
| 202 | 2-CH$_3$, 7-F | —OCH$_3$ | —H | —CH$_3$ | Cl | H | H | CH | —O— | 98-100 |
| 203 | 7-F | —OCH$_3$ | —H | —CH$_3$ | Cl | H | H | CH | —O— | amorphous |
| 204 | 8-F | —OH | —H | —C(=N—OCH$_3$)—CH$_3$ | Cl | H | H | CH | —O— | amorphous |
| 205 | 8-F | —OH | —H | —CH$_3$ | I | H | H | CH | —O— | 116-118 |
| 206 | 2-CH$_3$, 4,8-F$_2$ | —OH | —H | —CH$_3$ | F | H | H | CH | —O— | amorphous |
| 207 | 8-F | —N(CH$_3$)$_2$ | —H | —CH$_3$ | F | H | H | CH | —O— | $n_D^{20.3}$1.5836 |
| 208 | 8-F | —OCH$_3$ | —H | —CH$_3$ | I | H | H | CH | —O— | 61-63 |
| 209 | 8-F | —OCH$_3$ | —H | —CH$_3$ | CO$_2$CH$_3$ | H | H | CH | —O— | amorphous |
| 210 | 8-F | —OCH$_3$ | —H | —CH$_3$ | COCH$_3$ | H | H | CH | —O— | amorphous |
| 211 | 8-F | —OCH$_3$ | —H | —CH$_3$ | SCH$_3$ | H | H | CH | —O— | amorphous |
| 212 | 8-F | —OCH$_3$ | —H | —CH$_3$ | SO$_2$CH$_3$ | H | H | CH | —O— | amorphous |

TABLE 9-continued

| Compound No. | $(R^4)_m$ | $R^1$ | $R^2$ | $R^3$ | $R^b$ | $R^c$ | $R^d$ | E | —X— | Physical property |
|---|---|---|---|---|---|---|---|---|---|---|
| 213 | 8-F | —OCH$_3$ | —H | —CH$_3$ | OCH$_3$ | H | H | CH | —O— | |
| 214 | 8-F | —OCH$_3$ | —H | —CH$_3$ | $^c$Pr | H | H | CH | —O— | |
| 215 | 8-F | —OCH$_3$ | —H | —CH$_3$ | Ph | H | H | CH | —O— | amorphous |
| 216 | 8-F | —OCH$_3$ | —H | —CH$_3$ | N(CH$_3$)$_2$ | H | H | CH | —O— | |
| 217 | 8-F | —OCH$_3$ | —H | —OCH$_3$ | F | H | H | CH | —O— | amorphous |
| 218 | 8-F | —OEt | —H | —OEt | F | H | H | CH | —O— | amorphous |
| 219 | 8-F | —OH | —H | —H | Cl | H | H | CH | —O— | 141-143 |
| 220 | 8-F | —OCH$_3$ | —H | —H | Cl | H | H | CH | —O— | amorphous |
| 221 | 8-F | —OCH$_2$CH=CH$_2$ | —H | —H | Cl | H | H | CH | —O— | amorphous |
| 222 | 8-F | —OH | —H | —H | Br | H | H | CH | —O— | 142-144 |

TABLE 10

| Compound No. | $(R^4)_m$ | $R^1$ | $R^2$ | $R^3$ | $R^b$ | $R^c$ | $R^d$ | E | —X— | Physical property |
|---|---|---|---|---|---|---|---|---|---|---|
| 223 | 8-F | —OCH$_3$ | —H | —H | Br | H | H | CH | —O— | amorphous |
| 224 | 8-F | —NH—$^n$Bu | —H | —H | Cl | H | H | CH | —O— | amorphous |
| 225 | — | —CH$_3$ | —CH$_3$ | —C(CH$_3$)$_2$—CH$_2$OH | H | H | H | CH | —O— | amorphous |
| 226 | — | —CH$_3$ | —CH$_3$ | —C(CH$_3$)$_2$—CH$_2$O-Tos | H | H | H | CH | —O— | amorphous |
| 227 | — | —CH$_3$ | —CH$_3$ | —C(CH$_3$)$_2$OH | H | H | H | CH | —O— | amorphous |
| 228 | — | —CH$_3$ | —CH$_3$ | —CH$_2$OH | H | H | H | CH | —O— | 106-108 |
| 229 | — | —CH$_3$ | —CH$_3$ | —C(CH$_3$)$_2$—CHO | H | H | H | CH | —O— | 121-123 |
| 230 | — | —CH$_3$ | —CH$_3$ | —C(CH$_3$)$_2$—CH(CH$_3$)OH | H | H | H | CH | —O— | amorphous |
| 231 | — | —CH$_3$ | —CH$_3$ | —C(CH$_3$)$_2$—CH=N—OH | H | H | H | CH | —O— | 158-169 |
| 232 | — | —CH$_3$ | —CH$_3$ | —C(CH$_3$)$_2$—CN | H | H | H | CH | —O— | amorphous |
| 233 | — | —CH$_3$ | —CH$_3$ | —C(CH$_3$)$_2$—COCH$_3$ | H | H | H | CH | —O— | 107-109 |
| 234 | — | —CH$_3$ | —CH$_3$ | —CHO | H | H | H | CH | —O— | amorphous |
| 235 | — | —CH$_3$ | —CH$_3$ | —C(CH$_3$)$_2$—CH$_2$OH | F | H | H | CH | —O— | amorphous |
| 236 | 8-F | —CH$_3$ | —CH$_3$ | —C(CH$_3$)$_2$—CH$_2$OH | H | H | H | CH | —O— | 130-131 |
| 237 | 8-F | —CH$_3$ | —CH$_3$ | —C(CH$_3$)$_2$—CH$_2$OH | F | H | H | CH | —O— | 136-138 |
| 238 | 8-F | —CH$_3$ | —CH$_3$ | —C(CH$_3$)$_2$—CHO | H | H | H | CH | —O— | 148-149 |
| 239 | 8-F | —CH$_3$ | —CH$_3$ | —C(CH$_3$)$_2$—CHO | F | H | H | CH | —O— | 156-158 |
| 240 | 8-F | —CH$_3$ | —CH$_3$ | —C(CH$_3$)$_2$—COCH$_3$ | F | H | H | CH | —O— | 147-148 |
| 241 | 8-F | —CH$_3$ | —CH$_3$ | —CH$_2$OH | H | H | H | CH | —O— | amorphous |
| 242 | 8-F | —CH$_3$ | —CH$_3$ | —C(CH$_3$)$_2$OH | H | H | H | CH | —O— | 120-122 |
| 243 | — | —CH$_3$ | —CH$_3$ | —CH$_2$—C(CH$_3$)$_2$OH | H | H | H | CH | —O— | amorphous |
| 244 | — | —CH$_3$ | —CH$_3$ | —CH$_2$CH$_2$OH | H | H | H | CH | —O— | amorphous |
| 245 | — | —CH$_3$ | —CH$_3$ | —CH$_2$CHO | H | H | H | CH | —O— | 93-96 |
| 246 | — | —CH$_3$ | —CH$_3$ | —CH$_2$CH(CH$_3$)OH | H | H | H | CH | —O— | amorphous |
| 247 | — | —CH$_3$ | —CH$_3$ | —CH$_2$CH(OCH$_3$)$_2$ | H | H | H | CH | —O— | amorphous |
| 248 | — | —CH$_3$ | —CH$_3$ | —C(CH$_3$)$_2$—CH(OCH$_3$)$_2$ | H | H | H | CH | —O— | amorphous |

TABLE 11

| Compound No. | $(R^4)_m$ | $R^1$ | $R^2$ | $R^3$ | $R^b$ | $R^c$ | $R^d$ | E | —X— | Physical property |
|---|---|---|---|---|---|---|---|---|---|---|
| 249 | — | —CH$_3$ | —CH$_3$ | —C(CH$_3$)$_2$—CO$_2$H | H | H | H | CH | —O— | 181-184 |
| 250 | — | —CH$_3$ | —CH$_3$ | —C(CH$_3$)$_2$—CO$_2$CH$_3$ | H | H | H | CH | —O— | 123-125 |
| 251 | 2-CH$_3$ | —CH$_3$ | —CH$_3$ | —C(OH$_3$)$_2$OH | H | H | H | CH | —O— | amorphous |
| 252 | 2-CH$_3$ | —CH$_3$ | —CH$_3$ | —CH$_2$CH$_2$OH | H | H | H | CH | —O— | amorphous |
| 253 | — | —CH$_3$ | —CH$_3$ | —CH(CH$_3$)OH | H | H | H | CH | —O— | amorphous |
| 254 | — | —CH$_3$ | —CH$_3$ | —CH(OH)Et | H | H | H | CH | —O— | amorphous |
| 255 | — | —CH$_3$ | —CH$_3$ | —CH(OH)—C(CH$_3$)=CH$_2$ | H | H | H | CH | —O— | amorphous |
| 256 | 2-CH$_3$ | —CH$_3$ | —CH$_3$ | —C(CH$_3$)$_2$—CH(CH$_3$)OH | H | H | H | CH | —O— | amorphous |
| 257 | 2-CH$_3$ | —CH$_3$ | —CH$_3$ | —C(CH$_3$)$_2$—COCH$_3$ | H | H | H | CH | —O— | amorphous |
| 258 | 8-F | —CH$_3$ | —CH$_3$ | —CH$_2$CH$_2$OH | H | H | H | CH | —O— | amorphous |
| 259 | 2-CH$_3$, 8-F | —CH$_3$ | —CH$_3$ | —CH$_2$CH$_2$OH | H | H | H | CH | —O— | amorphous |
| 260 | — | —CH$_3$ | —CH$_3$ | —COCH$_3$ | H | H | H | CH | —O— | amorphous |
| 261 | 2-CH$_3$, 8-F | —CH$_3$ | —CH$_3$ | —CH$_2$CH$_2$OCH$_3$ | H | H | H | CH | —O— | amorphous |
| 262 | 8-F | —CH$_3$ | —CH$_3$ | —COCH$_3$ | F | H | H | CH | —O— | amorphous |
| 263 | — | —CH$_3$ | —CH$_3$ | —C(CH$_3$)$_2$OH | F | H | H | CH | —O— | amorphous |
| 264 | 8-F | —CH$_3$ | —CH$_3$ | —C(CH$_3$)$_2$OH | F | H | H | CH | —O— | 139-141 |
| 265 | — | —CH$_3$ | —CH$_3$ | —COCH$_3$ | F | H | H | CH | —O— | amorphous |
| 266 | 7-F | —CH$_3$ | —CH$_3$ | —COCH$_3$ | F | H | H | CH | —O— | viscous oil |
| 267 | 7,8-F$_2$ | —CH$_3$ | —CH$_3$ | —COCH$_3$ | F | H | H | CH | —O— | viscous oil |
| 268 | 8-F | —CH$_3$ | —CH$_3$ | —CH(CH$_3$)OH | H | H | H | CH | —O— | viscous oil |
| 269 | 8-F | —CH$_3$ | —CH$_3$ | —COCH$_3$ | H | H | H | CH | —O— | viscous oil |
| 270 | 2-CH$_3$, 8-F | —CH$_3$ | —CH$_3$ | —CN | H | H | H | CH | —O— | viscous oil |
| 271 | — | —CH$_3$ | —CH$_3$ | —CN | H | H | H | CH | —O— | amorphous |
| 272 | 8-F | —CH$_3$ | —CH$_3$ | —CN | H | H | H | CH | —O— | 126-128 |

TABLE 11-continued

| Compound No. | $(R^4)_m$ | $R^1$ | $R^2$ | $R^3$ | $R^b$ | $R^c$ | $R^d$ | E | —X— | Physical property |
|---|---|---|---|---|---|---|---|---|---|---|
| 273 | 8-F | —CH₃ | —CH₃ | —CONH₂ | H | H | H | CH | —O— | 172-175 |
| 274 | 8-F | —CH₃ | —CH₃ | —CON(CH₃)₂ | H | H | H | CH | —O— | 164-166 |

TABLE 12

| Compound No. | $(R^4)_m$ | $R^1$ | $R^2$ | $R^3$ | $R^b$ | $R^c$ | $R^d$ | E | —X— | Physical property |
|---|---|---|---|---|---|---|---|---|---|---|
| 275 | 8-F | —CH₃ | —CH₃ | —SO₂CH₃ | F | H | H | CH | —O— | 175-177 |
| 276 | — | —H | —CH₃ | —CH₃ | H | H | H | CH | —O— | 96-98 |
| 277 | — | —H | —CH₃ | —Et | H | H | H | CH | —O— | amorphous |
| 278 | — | —H | —CH₃ | —$^i$Pr | H | H | H | CH | —O— | amorphous |
| 279 | — | —H | —CH₃ | —$^n$Bu | H | H | H | CH | —O— | $n_D^{20.6}$1.6215 |
| 280 | 2-CH₃, 8-F | —OH | —H | —COCH₃ | F | H | H | CH | —O— | amorphous |
| 281 | — | —H | —H | —C(CH₃)₂OH | H | H | H | CH | —O— | 131-132 |
| 282 | — | —H | —H | —H | H | H | H | CH | —O— | 46-48 |
| 283 | — | —H | —H | —H | F | H | H | CH | —O— | 74-75 |
| 284 | 8-F | —H | —H | —H | F | H | H | CH | —O— | 82-83 |
| 285 | — | —CH=CH—CH=CH— | | | H | H | CH | —O— | 105-106 | |
| 286 | — | —(CH₂)₄— | | | H | H | CH | —O— | amorphous | |
| 287 | — | —(CH₂)₃— | | | H | H | CH | —O— | 68-70 | |
| 288 | — | —CH=CH—CH₂CH₂— | | | H | H | CH | —O— | 67-59 | |
| 289 | — | —F | —F | —CO₂Et | F | H | H | CH | —O— | 106-109 |
| 290 | — | —F | —F | —CH₂OH | F | H | H | CH | —O— | 129-131 |
| 291 | — | —F | —F | —C(CH₃)₂OH | F | H | H | CH | —O— | 99-101 |
| 292 | 8-F | —F | —F | —CO₂Et | F | H | H | CH | —O— | $n_D^{20.4}$1.5400 |
| 293 | 8-F | —F | —F | —C(CH₃)₂OH | F | H | H | CH | —O— | 114-116 |
| 294 | 8-F | —F | —F | —COCH₃ | F | H | H | CH | —O— | 60-63 |
| 295 | 8-F | —F | —F | —CON(CH₃)OCH₃ | F | H | H | CH | —O— | amorphous |
| 296 | 2-CH₃, 8-F | —F | —F | —COCH₃ | F | H | H | CH | —O— | 104-106 |
| 297 | 8-F | —(CH₂)₂— | | —OCH₂Ph | F | H | H | CH | —O— | amorphous |
| 298 | 8-F | —(CH₂)₂— | | —OH | F | H | H | CH | —O— | 128-130 |
| 299 | — | —(CH₂)₂— | | —OCH₂Ph | F | H | H | CH | —O— | 91-93 |
| 300 | — | —(CH₂)₂— | | —OH | F | H | H | CH | —O— | 123-124 |

TABLE 13

| Compound No. | $(R^4)_m$ | $R^1$ | $R^2$ | $R^3$ | $R^b$ | $R^c$ | $R^d$ | E | —X— | Physical property |
|---|---|---|---|---|---|---|---|---|---|---|
| 301 | 8-F | —(CH₂)₂— | | —OH | Cl | H | H | CH | —O— | |
| 302 | 2-CH₃, 8-F | —(CH₂)₂— | | —OH | Cl | H | H | CH | —O— | |
| 303 | 8-F | —(CH₂)₂— | | —OCH₂Ph | Cl | H | H | CH | —O— | |
| 304 | 2-CH₃, 8-F | —(CH₂)₂— | | —OCH₂Ph | Cl | H | H | CH | —O— | |
| 305 | — | =CH₂ | | —CH₃ | H | H | H | CH | —O— | 72-74 |
| 306 | 2-Cl | =CH₂ | | —CH₃ | H | H | H | CH | —O— | amorphous |
| 307 | 2-OH | =CH₂ | | —CH₃ | H | H | H | CH | —O— | 135-139 |
| 308 | 8-F | —O—CH₂— | | —CH₃ | F | H | H | CH | —O— | amorphous |
| 309 | — | —(CH₂)₄— | | —C(CH₃)₂OH | H | H | H | CH | —O— | 86-88 |
| 310 | 8-F | —(CH₂)₂— | | —CN | F | H | H | CH | —O— | 142-144 |
| 311 | 2-CH₃, 8-F | —(CH₂)₂— | | —CN | F | H | H | CH | —O— | 132-134 |
| 312 | 8-F | —(CH₂)₂— | | —COCH₃ | F | H | H | CH | —O— | |
| 313 | 2-CH₃, 8-F | —(CH₂)₂— | | —COCH₃ | F | H | H | CH | —O— | |
| 314 | 2-CH₃, 8-F | =N—OH | | —CH₃ | F | H | H | CH | —O— | 168-170 |
| 315 | 8-F | =N—OH | | —CH₃ | Cl | H | H | CH | —O— | 155-158 |
| 316 | 8-F | =N—OH | | —CH₃ | Br | H | H | CH | —O— | 145-147 |
| 317 | 8-F | =N—OH | | —CH₃ | Cl | F | H | CH | —O— | 199-202 |
| 318 | 2-CH₃, 7-F | =N—OCH₃ | | —CH₃ | F | H | H | CH | —O— | $n_D^{20.5}$1.5712 |
| 319 | 2-CH₃, 7-F | =N—OEt | | —CH₃ | F | H | H | CH | —O— | $n_D^{20.6}$1.5629 |
| 320 | — | =N—O$^t$Bu | | —H | F | H | H | CH | —O— | 105-107 |
| 321 | 8-F | ≡N | | Ph | F | H | H | CH | —O— | 184-185 |
| 322 | — | | | Ph | H | H | H | CH | —O— | 85-86 |
| 323 | — | —OH | —CH₃ | —CH₃ | F | H | H | CH | —CH₂— | 148-149 |
| 324 | 8-F | —OH | —CH₃ | —CH₃ | H | H | H | CH | —CH₂— | 114-116 |
| 325 | 2-CH₃, 8-F | —OH | —CH₃ | —CH₃ | H | H | H | CH | —CH₂— | 159-161 |
| 326 | — | —CH₃ | —CH₃ | —C(CH₃)₂—CH₂OH | H | H | H | CH | —CH₂— | 115-117 |

TABLE 14

| Compound No. | $(R^4)_m$ | $R^1$ | $R^2$ | $R^3$ | $R^b$ | $R^c$ | $R^d$ | E | —X— | Physical property |
|---|---|---|---|---|---|---|---|---|---|---|
| 327 | 8-F | —OH | —H | —CH$_3$ | Cl | H | H | CH | —CH$_2$— | 151-153 |
| 328 | 8-F | —OCH$_3$ | —H | —OCH$_3$ | Cl | H | H | CH | —CH$_2$— | amorphous |
| 329 | 8-F | =O | | —OEt | H | H | H | CH | —CH$_2$— | amorphous |
| 330 | — | =O | | —OEt | F | H | H | CH | —CH$_2$— | amorphous |
| 331 | 7-F | =O | | —OEt | F | H | H | CH | —CH$_2$— | viscous oil |
| 332 | 8-F | =O | | —H | Cl | H | H | CH | —CH$_2$— | 111-112 |
| 333 | 8-F | —OH | —CH$_3$ | —CH$_3$ | F | H | H | CH | —CO— | 192-193 |
| 334 | — | —OH | —H | —CH=CH$_2$ | H | H | H | CH | —CO— | amorphous |
| 335 | 8-F | =C(CH$_3$)$_2$ | | —H | F | H | H | CH | —CO— | 43-45 |
| 336 | — | —OCH$_2$CH$_2$O— | | —H | H | H | H | CH | —CO— | 134-136 |
| 337 | — | =CH$_2$ | | —H | H | H | H | CH | —CO— | 92-95 |
| 338 | — | =CH$_2$ | | —CH$_3$ | H | H | H | CH | —CO— | 125-128 |
| 339 | — | =C(CH$_3$)$_2$ | | —H | H | H | H | CH | —CO— | amorphous |
| 340 | — | —CH=CH—CH=CH— | | | | H | H | CH | —CO— | viscous oil |
| 341 | 8-F | =O | | —H | F | H | H | CH | —CO— | 179-181 |
| 342 | — | =O | | —H | H | H | H | CH | —CO— | 120-122 |
| 343 | — | =O | | —CH=CH$_2$ | H | H | H | CH | —CO— | amorphous |
| 344 | 8-F | —H | —H | —C(CH$_3$)=CH$_2$ | H | H | H | CH | —CO— | amorphous |
| 345 | — | —H | —H | —CH$_2$—N$_3$ | H | H | H | CH | —CO— | amorphous |
| 346 | — | —H | —H | —Ph | Cl | H | H | CH | —CO— | 115-117 |
| 347 | — | —H | —H | —C(CH$_3$)=CH$_2$ | F | H | H | CH | —CO— | amorphous |
| 348 | 8-F | —H | —H | —C(CH$_3$)=CH$_2$ | F | H | H | CH | —CO— | 89-92 |
| 349 | 8-F | —OCH$_2$CH$_2$O— | | —H | F | H | H | CH | —CH(OH)— | 159-161 |
| 350 | 8-F | —OH | —CH$_3$ | —CH$_3$ | F | H | H | CH | —CH(OH)— | amorphous |
| 351 | — | =CH$_2$ | | —H | H | H | H | CH | *1 | amorphous |
| 352 | — | =O | | —CO$_2$Et | H | H | H | CH | —O— | amorphous |

TABLE 15

| Compound No. | $(R^4)_m$ | $R^1$ $R^2$ | $R^3$ | $R^b$ | $R^c$ | $R^d$ | E | —X— | Physical property |
|---|---|---|---|---|---|---|---|---|---|
| 353 | 8-F | =O | —CH$_3$ | Cl | H | H | CH | —O— | amorphous |
| 354 | 8-F | =O | —CH$_3$ | *2 | H | H | CH | —O— | 146-148 |
| 355 | 8-F | =O | —CH$_3$ | Br | H | H | CH | —O— | amorphous |
| 356 | 8-F | =O | —CH$_3$ | F | H | H | CF | —O— | 103-104 |
| 357 | 8-F | =O | *3 | F | H | H | CH | —O— | amorphous |
| 358 | 2-CH$_3$, 8-F | =O | —CH$_3$ | F | H | H | CH | —O— | 96-100 |
| 359 | 2-CH$_3$, 8-F | =O | —CH$_3$ | Cl | H | H | CH | —O— | amorphous |
| 360 | 2-CH$_3$, 8-F | =O | —CH$_3$ | Br | H | H | CH | —O— | amorphous |
| 361 | 8-F | =O | —CH$_3$ | Cl | F | H | CH | —O— | amorphous |
| 362 | 2,4-(CH$_3$)$_2$, 8-F | =O | —CH$_3$ | F | H | H | CH | —O— | 164-65 |
| 363 | 8-F | =O | —$^c$Pr | Cl | H | H | CH | —O— | amorphous |
| 364 | 8-F | =O | —C(CH$_3$)=CH$_2$ | Cl | H | H | CH | —O— | amorphous |
| 365 | 8-F | =O | —$^t$Bu | Cl | H | H | CH | —O— | amorphous |
| 366 | 2-CH$_3$, 8-Cl | =O | —CH$_3$ | F | H | H | CH | —O— | 100-102 |
| 367 | 2,8-(CH$_3$)$_2$ | =O | —CH$_3$ | F | H | H | CH | —O— | amorphous |
| 368 | 8-F | =O | —Ph | Cl | H | H | CH | —O— | amorphous |
| 369 | 8-F | =O | —CH=CH$_2$ | Cl | H | H | CH | —O— | 77-79 |
| 370 | 8-F | =O | —C≡CH | Cl | H | H | CH | —O— | 121-123 |
| 371 | 8-F | =O | —$^n$Bu | Cl | H | H | CH | —O— | amorphous |
| 372 | 8-F | =O | —CH$_2$Cl | F | H | H | CH | —O— | 113-116 |
| 373 | 8-F | =O | —CHCl$_2$ | F | H | H | CH | —O— | amorphous |
| 374 | 8-F | =O | —CCl$_3$ | F | H | H | CH | —O— | amorphous |
| 375 | 8-F | =O | —COCH$_3$ | Cl | H | H | CH | —O— | amorphous |
| 376 | 8-F | =O | —C(CH$_3$)$_2$OH | Cl | H | H | CH | —O— | amorphous |
| 377 | 8-F | =O | —$^i$Pr | Cl | H | H | CH | —O— | amorphous |
| 378 | 8-F | =O | —CH$_3$ | Br | F | H | CH | —O— | 132-135 |

TABLE 16

| Compound No. | $(R^4)_m$ | $R^1$ $R^2$ | $R^3$ | $R^b$ | $R^c$ | $R^d$ | E | —X— | Physical property |
|---|---|---|---|---|---|---|---|---|---|
| 379 | 2-CH$_3$, 8-F | =O | —CH$_3$ | Cl | F | H | CH | —O— | 126-128 |
| 380 | 2-CH$_3$, 8-F | =O | —CH$_3$ | Br | F | H | CH | —O— | 126-128 |
| 381 | — | =O | —CH$_3$ | Cl | H | H | CH | —O— | 38-40 |
| 382 | 2-CH$_3$, 6-F | =O | —CH$_3$ | F | H | H | CH | —O— | amorphous |
| 383 | 2-CH$_3$, 7-F | =O | —CH$_3$ | F | H | H | CH | —O— | amorphous |
| 384 | 8-F | =O | —CH$_2$O—COCH$_3$ | F | H | H | CH | —O— | amorphous |
| 385 | — | =O | —CF$_3$ | F | H | H | CH | —O— | 100-104 |
| 386 | — | =O | —CH$_3$ | Cl | F | H | CH | —O— | 112-124 |

TABLE 16-continued

| Compound No. | $(R^4)_m$ | $R^1$ | $R^2$ | $R^3$ | $R^b$ | $R^c$ | $R^d$ | E | —X— | Physical property |
|---|---|---|---|---|---|---|---|---|---|---|
| 387 | 5,8-F$_2$ | =O | | —CH$_3$ | F | H | H | CH | —O— | 45-48 |
| 388 | 5-F | =O | | —CH$_3$ | F | H | H | CH | —O— | amorphous |
| 389 | 2-CH$_3$, 7-Cl | =O | | —CH$_3$ | F | H | H | CH | —O— | amorphous |
| 390 | 8-F | =O | | —CF$_3$ | F | H | H | CH | —O— | amorphous |
| 391 | 7,8-F$_2$ | =O | | —CH$_3$ | F | H | H | CH | —O— | 128-130 |
| 392 | 7,8-F$_2$ | =O | | —CH$_3$ | Cl | H | H | CH | —O— | 105-107 |
| 393 | 2-CH$_3$, 8-F | =O | | —COCH$_3$ | Cl | H | H | CH | —O— | 113-114 |
| 394 | 7-F | =O | | —CH$_3$ | F | H | H | CH | —O— | 97-99 |
| 395 | 2-CH$_3$, 8-F | =O | | —COCH$_3$ | F | H | H | CH | —O— | 169-170 |
| 396 | 8-F | =O | | —COCH$_3$ | F | H | H | CH | —O— | 96-98 |
| 397 | 2-CH$_3$, 8-F | =O | | —C(CH$_3$)$_2$OH | F | H | H | CH | —O— | amorphous |
| 398 | 8-F | =O | | —C(CH$_3$)$_2$OH | F | H | H | CH | —O— | amorphous |
| 399 | 8-F | =O | | —C(=N—OCH$_3$)—CH$_3$ | Cl | H | H | CH | —O— | 118-119 |
| 400 | 2-CH$_3$, 4,8-F$_2$ | =O | | —CH$_3$ | F | H | H | CH | —O— | 155-156 |
| 401 | — | =O | | —NHPh | H | H | H | CH | —O— | amorphous |
| 402 | — | =O | | —OCH$_3$ | Cl | H | H | CH | —O— | amorphous |
| 403 | — | =O | | —OCH$_3$ | Br | H | H | CH | —O— | amorphous |
| 404 | 8-F | =O | | —OEt | H | Cl | H | CH | —O— | 88-90 |

TABLE 17

| Compound No. | $(R^4)_m$ | $R^1$ | $R^2$ | $R^3$ | $R^b$ | $R^c$ | $R^d$ | E | —X— | Physical property |
|---|---|---|---|---|---|---|---|---|---|---|
| 405 | 8-F | =O | | —OEt | H | CH$_3$ | H | CH | —O— | 88-90 |
| 406 | 8-F | =O | | —OCH$_3$ | Cl | H | H | CH | —O— | $n_D^{20.8}$1.6008 |
| 407 | 8-F | =O | | —O$^i$Pr | Cl | H | H | CH | —O— | $n_D^{20.7}$1.5809 |
| 408 | 8-F | =O | | —O—CH$_2$Ph | Cl | H | H | CH | —O— | 114-116 |
| 409 | 8-F | =O | | —OEt | F | CH$_3$ | H | CH | —O— | amorphous |
| 410 | 8-F | =O | | —O$^t$Bu | Cl | H | H | CH | —O— | amorphous |
| 411 | 8-F | =O | | —O—C(CH$_3$)$_2$—CO$_2$Et | Cl | H | H | CH | —O— | $n_D^{22.4}$1.5411 |
| 412 | 8-F | =O | | —H | Cl | F | H | CH | —O— | 153-155 |
| 413 | 8-F | =O | | —H | Cl | H | H | CH | —O— | 133-135 |
| 414 | 8-F | =O | | —H | Br | H | H | CH | —O— | 111-114 |
| 415 | 8-F | =O | | —H | Bn | H | H | CH | —O— | 92-94 |
| 416 | 8-F | =O | | —H | NO$_2$ | H | H | CH | —O— | 106-109 |
| 417 | 8-F | =O | | —H | Br | F | H | CH | —O— | 140-142 |
| 418 | 8-F | =O | | —H | CF$_3$ | H | H | CH | —O— | 125-127 |
| 419 | — | =O | | —H | Cl | H | H | CH | —O— | 82-85 |
| 420 | — | =O | | —H | Cl | F | H | CH | —O— | 136-138 |
| 421 | 5,8-F$_2$ | =O | | —H | F | H | H | CH | —O— | 118-121 |
| 422 | 5-F | =O | | —H | F | H | H | CH | —O— | 92-94 |
| 423 | 7,8-F$_2$ | =O | | —H | Cl | H | H | CH | —O— | 142-144 |
| 424 | 7-F | =O | | —H | Cl | H | H | CH | —O— | 122-123 |
| 425 | 2-CH$_3$, 8-F | —F | —F | —C(CH$_3$)$_2$OH | F | H | H | CH | —O— | 110-112 |
| 426 | 2-CH$_3$, 8-F | —F | —F | —CH(CH$_3$)OH | F | H | H | CH | —O— | 163-165 |
| 427 | 2-CH$_3$, 8-F | —F | —F | —CH(CH$_3$)OCH$_3$ | F | H | H | CH | —O— | amorphous |
| 428 | 2-CH$_3$, 8-F | —F | —F | —C(CH$_3$)(Et)OH | F | H | H | CH | —O— | amorphous |
| 429 | 2-CH$_3$, 8-F | —F | —F | —CH(CH$_3$)OCH$_2$OCH$_3$ | F | H | H | CH | —O— | 141-143 |
| 430 | 8-F | —(CH$_2$)$_2$— | | —CO$_2$Et | F | H | H | CH | —O— | amorphous |

TABLE 18

| Compound No. | $(R^4)_m$ | $R^1$ | $R^2$ | $R^3$ | $R^b$ | $R^c$ | $R^d$ | E | —X— | Physical property |
|---|---|---|---|---|---|---|---|---|---|---|
| 431 | 8-F | —(CH$_2$)$_2$— | | —C(CH$_3$)$_2$OH | F | H | H | CH | —O— | amorphous |
| 432 | 8-F | —CH$_3$ | —CH$_3$ | —CN | F | H | H | CH | —O— | 110-112 |
| 433 | 8-F | —NHCO$_2^t$Bu | —CH$_3$ | —CH$_3$ | F | H | H | CH | —O— | 127-129 |
| 434 | 8-F | —(CH$_2$)$_2$— | | —NHCO$_2^t$Bu | F | H | H | CH | —O— | 132-134 |
| 435 | 8-F | —NH$_2$ | —CH$_3$ | —CH$_3$ | F | H | H | CH | —O— | amorphous |
| 436 | 8-F | —NHCOCH$_3$ | —CH$_3$ | —CH$_3$ | F | H | H | CH | —O— | 144-146 |
| 437 | 8-F | —NHCOCF$_3$ | —CH$_3$ | —CH$_3$ | F | H | H | CH | —O— | amorphous |
| 438 | — | —OCH$_2$CH$_2$O— | | —H | H | H | H | CH | —CH(OH)— | 80-83 |
| 439 | 2-CH$_3$, 7,8-F$_2$ | —OCH$_3$ | —CH$_3$ | —CH$_3$ | F | H | H | CH | —O— | 97-98 |
| 440 | 2-CH$_3$, 8-F | —OCH$_3$ | —CH$_3$ | —CH$_3$ | F | H | H | CH | —O— | 94-95 |
| 441 | 2-CH$_3$, 7-F | —OCH$_3$ | —CH$_3$ | —CH$_3$ | F | H | H | CH | —O— | 104-105 |
| 442 | 8-F | —N(CH$_3$)$_2$ | —H | —CN | Cl | H | H | CH | —O— | amorphous |
| 443 | 8-F | —NHCOCH$_3$ | —H | —CN | Cl | H | H | CH | —O— | amorphous |
| 444 | 8-F | —N(Bn)COCH$_3$ | —CH$_3$ | —CH$_3$ | F | H | H | CH | —O— | 195-197 |
| 445 | 8-F | Pyrrolidin-1-yl | —H | —CH$_3$ | F | H | H | CH | —O— | $n_D^{20.6}$1.5593 |
| 446 | 8-F | —OCH$_3$ | —H | —CH$_3$ | NHCO$_2^t$Bu | H | H | CH | —O— | amorphous |

TABLE 18-continued

| Compound No. | (R⁴)ₘ | R¹ | R² | R³ | Rᵇ | Rᶜ | Rᵈ | E | —X— | Physical property |
|---|---|---|---|---|---|---|---|---|---|---|
| 447 | 8-F | —OCH₃ | —H | —CH₃ | NH2 | H | H | CH | —O— | amorphous |
| 448 | 8-F | —OCH₃ | —H | —CH₃ | NHCH₃ | H | H | CH | —O— | amorphous |
| 449 | 2-CH₃, 8-F | —CH₃ | —CH₃ | —SO₂CH₃ | F | H | H | CH | —O— | 138-141 |
| 450 | 7,8-F₂ | —CH₃ | —CH₃ | —SO₂CH₃ | F | H | H | CH | —O— | 157-160 |
| 451 | 2-CH₃, 7,8-F₂ | —CH₃ | —CH₃ | —SO₂CH₃ | F | H | H | CH | —O— | 172-175 |

TABLE 19

| Compound No. | (R⁴)ₘ | R¹ | R² | R³ | Rᵇ | Rᶜ | Rᵈ | E | —X— | Physical property |
|---|---|---|---|---|---|---|---|---|---|---|
| 452 | 8-F | —CH₃ | —CH₃ | —SO₂Et | F | H | H | CH | —O— | 150-152 |
| 453 | 8-F | —CH₃ | —H | —SO₂CH₃ | Cl | H | H | CH | —O— | amorphous |

*1 = " —C(=N—CH₂CH=CH₂)— "

*2 = "8-Fluoro-quinolin-3-yloxy"

*3 = "

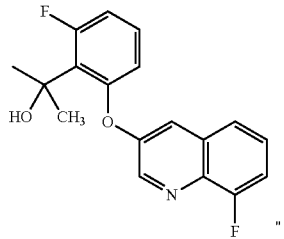

"

TABLE 20

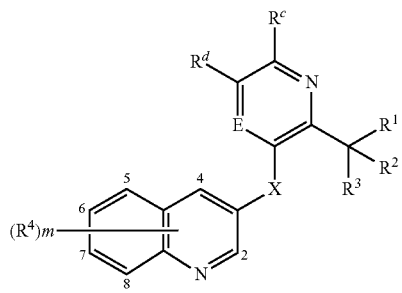

| Compound No. | (R⁴)ₘ | R¹ | R² | R³ | Rᶜ | Rᵈ | E | —X— | Physical property |
|---|---|---|---|---|---|---|---|---|---|
| a-1 | — | | ≡N | | H | H | CH | —O— | 149-150 |
| a-2 | — | —OH | —CH₃ | —CH₃ | H | H | CH | —O— | amorphous |
| a-3 | 8-F | =O | | —H | H | H | CH | —O— | 138-140 |
| a-4 | 2-ᵗBu, 8-F | =O | | —H | H | H | CH | —O— | 150-151 |
| a-5 | 8-F | —OH | —CH₃ | —ᵗBu | H | H | CH | —O— | 110-112 |
| a-6 | 8-F | =O | | —ᵗBu | H | H | CH | —O— | 90-91 |
| a-7 | 2-CH₃, 8-F | —OH | —CH₃ | —CH₃ | H | H | CH | —O— | amorphous |
| a-8 | 8-F | —OH | —CH₃ | —CH₃ | H | H | CH | —O— | amorphous |
| a-9 | 2-CH₃, 8-F | =O | | —CH₃ | H | H | CH | —O— | 133-134 |
| a-10 | 2-CH₃, 8-F | —OH | —CH₃ | —ᵗBu | H | H | CH | —O— | 133-136 |
| a-11 | 8-F | —CH₃ | —CH₃ | —CN | H | H | CH | —O— | |
| a-12 | 8-F | —CH₃ | —CH₃ | —CO₂Et | H | H | CH | —O— | |
| a-13 | 8-F | —F | —F | —C(CH₃)₂OH | H | H | CH | —O— | |
| a-14 | 8-F | —CH₃ | —CH₃ | —C(CH₃)₂OH | H | H | CH | —O— | |
| a-15 | 8-F | —CH₃ | —CH₃ | —COCH₃ | H | H | CH | —O— | |

TABLE 21

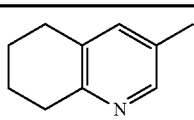

| Compound No | Q | R¹ | R² | R³ | $R^b$ | $R^c$ | $R^d$ | E | —X— | Physical property |
|---|---|---|---|---|---|---|---|---|---|---|
| b-1 | 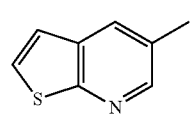 | —CH₃ | —CH₃ | —C(CH₃)₂OH | H | H | H | CH | —O— | viscous oil |
| b-2 | 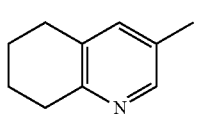 | —CH₃ | —CH₃ | —C(CH₃)₂OH | H | H | H | CH | —O— | 133-135 |
| b-3 | 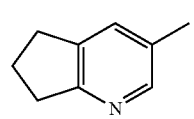 | —CH₃ | —CH₃ | —C(CH₃)₂OH | F | H | H | CH | —O— | viscous oil |
| b-4 | 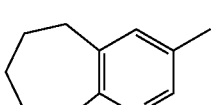 | —CH₃ | —CH₃ | —C(CH₃)₂OH | H | H | H | CH | —O— | viscous oil |
| b-5 | 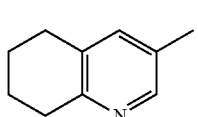 | —CH₃ | —CH₃ | —C(CH₃)₂OH | H | H | H | CH | —O— | viscous oil |
| b-6 | 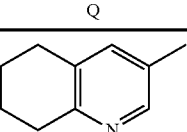 | =O | | —CH₃ | F | H | H | CH | —O— | viscous oil |

TABLE 22

| Compound No. | Q | R¹ | R² | R³ | $R^b$ | $R^c$ | $R^d$ | E | —X— | Physical property |
|---|---|---|---|---|---|---|---|---|---|---|
| b-7 | 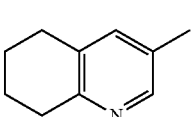 | —OH | —CH₃ | —CH₃ | F | H | H | CH | —O— | viscous oil |
| b-8 | 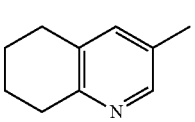 | —OH | —CH₃ | —ᵗBu | F | H | H | CH | —O— | viscous oil |
| b-9 | 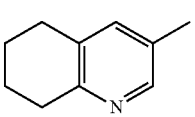 | —OH | —H | —CH₃ | F | H | H | CH | —O— | viscous oil |
| b-10 |  | —OCH₃ | —H | —CH₃ | F | H | H | CH | —O— | viscous oil |

TABLE 22-continued

| Compound No. | Q | R¹ | R² | R³ | $R^b$ | $R^c$ | $R^d$ | E | —X— | Physical property |
|---|---|---|---|---|---|---|---|---|---|---|
| b-11 | 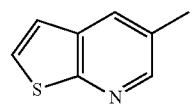 | =O | | —CH₃ | F | H | H | CH | —O— | viscous oil |
| b-12 | 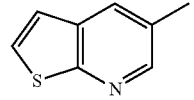 | —OH | —CH₃ | —CH₃ | F | H | H | CH | —O— | viscous oil |
| b-13 | 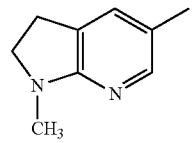 | —CH₃ | —CH₃ | —C(CH₃)₂OH | H | H | H | CH | —O— | viscous oil |
| b-14 | 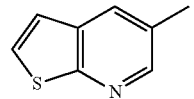 | —OH | —H | —CH₃ | F | H | H | CH | —O— | viscous oil |

TABLE 23

| Compound No. | Q | R¹ | R² | R³ | $R^b$ | $R^c$ | $R^d$ | E | —X— | Physical property |
|---|---|---|---|---|---|---|---|---|---|---|
| b-15 | 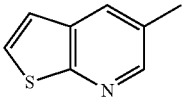 | —OCH₃ | —H | —CH₃ | F | H | H | CH | —O— | viscous oil |
| b-16 | 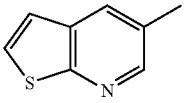 | —OH | —CH₃ | —ᵗBu | F | H | H | CH | —O— | amorphous |
| b-17 | 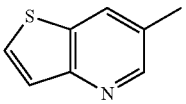 | =O | | CH₃ | F | H | H | CH | —O— | 78-80 |
| b-18 | 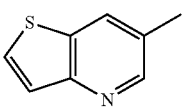 | —OH | —CH₃ | —CH₃ | F | H | H | CH | —O— | 101-102 |
| b-19 | 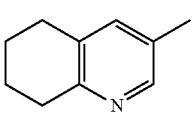 | =C(CH₃)₂ | —H | | F | H | H | CH | —CO— | viscous oil |
| b-20 | 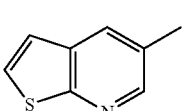 | =C(CH₃)₂ | —H | | F | H | H | CH | —CO— | amorphous |
| b-21 | 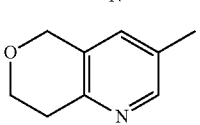 | =O | | —CH₃ | F | H | H | CH | —O— | viscous oil |

TABLE 23-continued

| Compound No. | Q | $R^1$ | $R^2$ | $R^3$ | $R^b$ | $R^c$ | $R^d$ | E | —X— | Physical property |
|---|---|---|---|---|---|---|---|---|---|---|
| b-22 | | —OH | —CH₃ | —CH₃ | F | H | H | CH | —O— | viscous oil |

TABLE 24

| Compound No. | Q | $R^1$ | $R^2$ | $R^3$ | $R^b$ | $R^c$ | $R^d$ | E | —X— | Physical property |
|---|---|---|---|---|---|---|---|---|---|---|
| b-23 | | =O | | —CH₃ | F | H | H | CH | —O— | viscous oil |
| b-24 | | —OH | —CH₃ | —CH₃ | F | H | H | CH | —O— | 87-89 |
| b-25 | | —OH | —CH₃ | —CH₃ | F | H | H | CH | —O— | |
| b-26 | | —OH | —CH₃ | —CH₃ | F | H | H | CH | —O— | |

TABLE 25

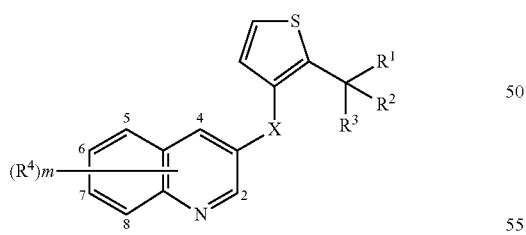

| Compound No. | $(R^4)_m$ | $R^1$ | $R^2$ | $R^3$ | —X— | Physical property |
|---|---|---|---|---|---|---|
| c-1 | 8-F | =O | | —OCH₃ | —O— | |
| c-2 | 8-F | =O | | —H | —O— | 135-137 |
| c-3 | 8-F | =O | | —CH₃ | —O— | 138-139 |
| c-4 | 8-F | —OH | —CH₃ | —CH₃ | —O— | 129-131 |
| c-5 | 8-F | —OH | —H | —CH₃ | —O— | 96-98 |

TABLE 26

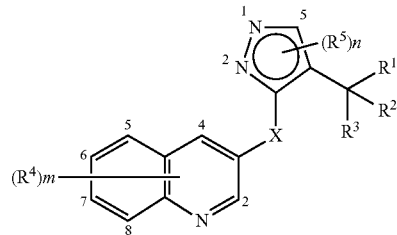

| Compound No. | $(R^4)_m$ | $R^1$ | $R^2$ | $R^3$ | $(R^5)_n$ | —X— | Physical property |
|---|---|---|---|---|---|---|---|
| d-1 | 8-F | =O | | —OCH$_3$ | 2-CH$_3$, 5-CF$_3$ | —O— | |
| d-2 | 8-F | =O | | —H | 2-CH$_3$, 5-CF$_3$ | —O— | |
| d-3 | 8-F | =O | | —CH$_3$ | 2-CH$_3$, 5-CF$_3$ | —O— | |
| d-4 | 8-F | —OH | —H | —CH$_3$ | 2-CH$_3$, 5-CF$_3$ | —O— | 160-162 |
| d-5 | 8-F | —OCH$_3$ | —H | —CH$_3$ | 2-CH$_3$, 5-CF$_3$ | —O— | $n_D^{20.6}$1.5056 |
| d-6 | 8-F | —OH | —H | —$^i$Pr | 2-CH$_3$, 5-CF$_3$ | —O— | |
| d-7 | 8-F | —OH | —H | —$^c$Pr | 2-CH$_3$, 5-CF$_3$ | —O— | |
| d-8 | 8-F | —OH | —H | —CF$_3$ | 2-CH$_3$, 5-CF$_3$ | —O— | |
| d-9 | 8-F | —OH | —H | —C(CH$_3$)$_2$OH | 2-CH$_3$, 5-CF$_3$ | —O— | |
| d-10 | 8-F | —OH | —H | —C(CH$_3$)$_2$—COCH$_3$ | 2-CH$_3$, 5-CF$_3$ | —O— | |
| d-11 | 8-F | —OH | —H | —C(CH$_3$)$_2$—CO$_2$CH$_3$ | 2-CH$_3$, 5-CF$_3$ | —O— | |

TABLE 27

| Compound No. | $(R^4)_m$ | $R^1$ | $R^2$ | $R^3$ | $(R^5)_n$ | —X— | Physical property |
|---|---|---|---|---|---|---|---|
| d-12 | 8-F | —OH | —H | —CH$_2$Ph | 2-CH$_3$, 5-CF$_3$ | —O— | |
| d-13 | 8-F | —OH | —H | —CH=CH$_2$ | 2-CH$_3$, 5-CF$_3$ | —O— | |
| d-14 | 8-F | —OH | —H | —C≡CH | 2-CH$_3$, 5-CF$_3$ | —O— | |
| d-15 | 8-F | —OH | —H | —COCH$_3$ | 2-CH$_3$, 5-CF$_3$ | —O— | |
| d-16 | 2-CH$_3$, 8-F | —OH | —H | —CH$_3$ | 2-CH$_3$, 5-CF$_3$ | —O— | |
| d-17 | 2-CH$_3$, 8-F | —OH | —H | —$^i$Pr | 2-CH$_3$, 5-CF$_3$ | —O— | |
| d-18 | 2-CH$_3$, 8-F | —OH | —H | —$^c$Pr | 2-CH$_3$, 5-CF$_3$ | —O— | |
| d-19 | 2-CH$_3$, 8-F | —OH | —H | —CF$_3$ | 2-CH$_3$, 5-CF$_3$ | —O— | |
| d-20 | 2-CH$_3$, 8-F | —OH | —H | —C(CH$_3$)$_2$OH | 2-CH$_3$, 5-CF$_3$ | —O— | |
| d-21 | 2-CH$_3$, 8-F | —OH | —H | —CH=CH$_2$ | 2-CH$_3$, 5-CF$_3$ | —O— | |
| d-22 | 2-CH$_3$, 8-F | —OH | —H | —C≡CH | 2-CH$_3$, 5-CF$_3$ | —O— | |
| d-23 | 8-F | —OH | —CH$_3$ | —CH$_3$ | 2-CH$_3$, 5-Cl | —O— | |
| d-24 | 8-F | —OH | —CH$_3$ | —$^i$Pr | 2-CH$_3$, 5-Cl | —O— | |
| d-25 | 8-F | —OH | —CH$_3$ | —$^c$Pr | 2-CH$_3$, 5-Cl | —O— | |
| d-26 | 8-F | —OH | —CH$_3$ | —CF$_3$ | 2-CH$_3$, 5-Cl | —O— | |
| d-27 | 8-F | —OH | —CH$_3$ | —C(CH$_3$)$_2$OH | 2-CH$_3$, 5-Cl | —O— | |
| d-28 | 8-F | —OH | —CH$_3$ | —C(CH$_3$)$_2$—COCH$_3$ | 2-CH$_3$, 5-Cl | —O— | |
| d-29 | 8-F | —OH | —CH$_3$ | —C(CH$_3$)$_2$—CO$_2$CH$_3$ | 2-CH$_3$, 5-Cl | —O— | |
| d-30 | 8-F | —OH | —CH$_3$ | —CH$_2$Ph | 2-CH$_3$, 5-Cl | —O— | |
| d-31 | 8-F | —OH | —CH$_3$ | —CH=CH$_2$ | 2-CH$_3$, 5-Cl | —O— | |
| d-32 | 8-F | —OH | —CH$_3$ | —C≡CH | 2-CH$_3$, 5-Cl | —O— | |
| d-33 | 8-F | —OH | —CH$_3$ | —COCH$_3$ | 2-CH$_3$, 5-Cl | —O— | |
| d-34 | 2-CH$_3$, 8-F | —OH | —CH$_3$ | —CH$_3$ | 2-CH$_3$, 5-Cl | —O— | |
| d-35 | 2-CH$_3$, 8-F | —OH | —CH$_3$ | —$^i$Pr | 2-CH$_3$, 5-Cl | —O— | |

TABLE 28

| Compound No. | $(R^4)_m$ | $R^1$ | $R^2$ | $R^3$ | $(R^5)_n$ | —X— | Physical property |
|---|---|---|---|---|---|---|---|
| d-36 | 2-CH$_3$, 8-F | —OH | —CH$_3$ | —$^c$Pr | 2-CH$_3$, 5-Cl | —O— | |
| d-37 | 2-CH$_3$, 8-F | —OH | —CH$_3$ | —CF$_3$ | 2-CH$_3$, 5-Cl | —O— | |
| d-38 | 2-CH$_3$, 8-F | —OH | —CH$_3$ | —C(CH$_3$)$_2$OH | 2-CH$_3$, 5-Cl | —O— | |
| d-39 | 2-CH$_3$, 8-F | —OH | —CH$_3$ | —CH=CH$_2$ | 2-CH$_3$, 5-Cl | —O— | |
| d-40 | 2-CH$_3$, 8-F | —OH | —CH$_3$ | —C≡CH | 2-CH$_3$, 5-Cl | —O— | |

TABLE 29

| Compound No | ¹H-NMR |
|---|---|
| 3 | 1.16(t, 3H), 4.23(q, 2H), 7.13(d, 1H), 7.29-7.64(m, 6H), 8.02(m, 1H), 8.08(d, 1H), 8.83(d, 1H). |
| 5 | 1.19(t, 3H), 4.24(q, 2H), 6.80(m, 1H), 7.01(m, 1H), 7.43(d, 1H), 7.50-7.71(m, 3H), 8.04-8.16(m, 2H), 8.83(br, 1H). |
| 7 | 1.22(t, 3H), 4.31(q, 2H), 6.79(d, 1H), 6.99(t, 1H), 7.38(m, 1H), 7.51-7.72(m, 4H), 8.11(d, 1H), 8.81(d, 1H) |
| 8 | 1.20(t, 3H), 4.32(q, 2H), 6.85(d, 1H), 7.03(t, 1H), 7.30-7.54(m, 5H), 8.85(d, 1H). |
| 9 | 7.03(d, 1H), 7.27(d, 1H), 7.30-7.77(m, 6H), 8.12(d, 1H), 8.81(d, 1H). |
| 10 | 2.61(s, 3H), 6.79(m, 1H), 7.01(t, 1H), 7.31-7.43(m, 2H), 7.47-7.50(m, 2H), 7.58(m, 1H), 8.83(d, 1H). |
| 11 | 1.28(s, 9H), 6.97(d, 1H), 7.17-7.26(m, 2H), 7.26(m, 1H), 7.52(t, 1H), 7.56(d, 1H), 7.63(m, 1H), 7.69(d, 1H), 8.09(d, 1H), 8.77(d, 1H). |
| 12 | 1.28(s, 9H), 6.76(d, 1H), 6.98(t, 1H), 7.27-7.50(m, 4H), 7.59(m, 1H), 8.87(d, 1H). |
| 13 | 7.13(m, 1H), 7.54(m, 1H), 7.69(m, 1H), 7.79(m, 1H), 7.96-8.04(m, 2H), 8.14(d, 1H), 8.25(br, 1H), 8.83(d, 1H). |
| 14 | 1.35(d, 9H), 6.82(d, 1H), 7.03-7.14(m, 2H), 7.38-7.56(m, 5H), 8.02(d, 1H), 8.73(s, 1H). |
| 17 | 0.71(t, 3H), 1.39(s, 6H), 1.84(q, 2H), 6.90(m, 1H), 7.12-7.23(m, 2H), 7.41(d, 1H), 7.43-7.68(m, 4H), 8.10(d, 1H), 8.80(br, 1H). |
| 18 | 0.66(t, 3H), 1.37(s, 6H), 1.85(q, 2H), 6.64(d, 1H), 6.84-6.93(m, 2H), 7.07(m, 1H), 7.15-7.26(m, 2H), 7.41-7.47(m, 2H), 8.82(d, 1H). |
| 22 | 2.88(s, 3H), 3.12(s, 3H), 6.88(d, 1H), 7.20(t, 1H), 7.41(d, 1H), 7.54(t, 1H), 7.63-7.73(m, 3H), 8.10(d, 1H), 8.79(d, 1H). |
| 24 | 2.19(s, 3H), 3.89(s, 3H), 7.03(d, 1H), 7.26(m, 1H), 7.36-7.43(m, 2H), 7.48-7.55(m, 2H), 7.59-7.67(m, 2H), 8.09(d, 1H), 8.81(d, 1H). |
| 25 | 1.18(s, 9H), 2.18(s, 3H), 7.05(d, 1H), 7.26(m, 1H), 7.35-7.64(m, 6H), 8.08(d, 1H), 8.80(d, 1H) |
| 27 | 1.73(s, 3H), 3.17(s, 6H), 6.98(d, 1H), 7.19(t, 1H), 7.29(m, 1H), 7.48-7.68(m, 4H), 7.82(dd, 1H), 8.08(d, 1H), 8.79(d, 1H) |
| 28 | 0.20(s, 9H), 1.76(d, 1H), 4.57(br, 1H), 6.62(d, 1H), 6.92(m, 1H), 7.15(m, 1H), 7.33(m, 1H), 7.33(m, 1H), 7.46-7.51(m, 2H), 7.70(s, 1H), 8.83(br, 1H). |
| 30 | 1.06(s, 9H), 1.76(d, 1H), 4.57(br, 1H), 6.62(d, 1H), 6.92(m, 1H), 7.15(m, 1H), 7.33(m, 1H), 7.46-7.51(m, 2H), 7.70(s, 1H), 8.83(br. 1H). |
| 31 | 1.03(s, 9H), 1.60(s, 1H), 1.68(s, 3H), 6.86(m, 1H), 7.13-7.24(m, 2H), 7.51-7.71(m, 5H), 8.11(d, 1H), 8.79(d, 1H). |
| 34 | 1.70(s, 3H), 2.22-2.37(m, 2H), 2.43(br, 1H), 2.91(m, 1H), 3.08(m, 1H), 6.72(d, 1H), 7.07(d, 1H), 7.24(t, 1H), 7.32(m, 1H), 7.45-7.49(m, 2H), 7.59(m, 1H), 8.88(d, 1H). |
| 35 | 1.07(s, 9H), 2.13(m, 1H), 2.65(m, 1H), 2.93-2.99(m, 3H), 6.69(d, 1H), 7.03(d, 1H), 7.19(t, 1H), 7.33(m, 1H), 7.45-7.52(m, 2H), 7.67(m, 1H), 8.85(d, 1H). |

TABLE 30

| Compound No | ¹H-NMR |
|---|---|
| 36 | 1.75(d, 6H), 3.79(d, 1H), 6.69(m, 1H), 6.958m, 1H), 7.20(m, 1H), 7.35(m, 1H), 7.45-7.51(m, 2H), 7.59(d, 1H), 8.83(d, 1H). |
| 37 | 1.76(d, 6H), 2.80(s, 3H), 3.87(br, 1H), 6.58(d, 1H), 6.93(m, 1H), 7.19(m, 1H), 7.29-7.45(m, 4H). |
| 38 | 1.70(s, 6H), 3.01(br, 1H), 6.87(d, 1H), 7.15-7.25(m, 2H), 7.54(t, 1H), 7.60-7.71(m, 4H), 8.12(d, 1H), 8.81(d, 1H). |
| 39 | 1.28(s, 9H), 7.03(s, 1H), 7.36(d, 1H), 7.52-7.72(m, 4H), 7.95(d, 1H), 8.13(d, 1H), 8.87(d, 1H), 10.42(s, 1H). |
| 40 | 1.64(s, 6H), 2.53(s, 1H), 7.12(m, 1H), 7.21-7.32(m, 2H), 7.50-7.67(m, 4H), 8.11(d, 1H), 8.85(d, 1H). |
| 41 | 1.70(s, 6H), 2.77(s, 1H), 6.56(m, 1H), 6.86(m, 1H), 7.54-7.75(m, 5H), 8.13(d, 1H), 8.80(d, 1H). |
| 42 | 1.68(s, 6H), 2.88(s, 1H), 6.84-6.97(m, 2H), 7.44(m, 1H), 7.52-7.57(m, 2H), 7.62-7.71(m, 2H), 8.12(d, 1H), 8.79(d, 1H). |
| 43 | 1.77(d, 6H), 4.00(d, 1H), 6.66(m, 1H), 6.90(m, 1H), 8.18(m, 1H), 8.53-7.73(m, 4H), 8.12(d, 1H), 8.79(d, 1H). |
| 46 | 1.43(t, 3H), 1.72(s, 6H), 2.95(s, 1H), 3.14(q, 2H), 6.80(d, 1H), 7.16-7.25(m, 2H), 7.43-7.48(m, 2H), 7.60-7.67(m, 3H), 8.07(d, 1H). |
| 47 | 0.94(t, 3H), 1.16(m, 2H), 1.72(s, 6H), 1.87(m, 2H), 2.92(s, 1H), 3.10(t, 2H), 6.81(d, 1H), 7.14-7.23(m, 2H), 7.43-7.48(m, 2H), 7.59-7.67(m, 3H), 8.07(d, 1H). |
| 48 | 0.93(t, 3H), 1.72(d, 3H), 1.95(m, 1H), 2.08(m, 1H), 3.87(d, 1H), 6.68(d, 1H), 6.95(m, 1H), 7.21(m, 1H), 7.36(m, 1H), 7.44-7.51(m, 2H), 7.59(m, 1H), 8.82(d, 1H). |
| 49 | 1.75(d, 6H), 3.76(d, 1H), 6.69(m, 1H), 6.94(m, 1H), 7.20(m, 1H), 7.47(d, 1H), 7.59-7.66(m, 2H), 7.78(dd, 1H), 8.90(d, 1H). |
| 51 | 6.81-6.84(m, 1H), 7.39-7.64(m, 8H), 7.72-7.76(m, 3H), 7.99(d, 1H), 8.07(d, 1H), 8.89(d, 1H), 10.29(s, 1H). |
| 53 | 1.19(t, 3H), 4.25(q, 2H), 4.31(s, 2H), 7.04(d, 1H), 7.32-7.53(m, 5H), 7.86(s, 1H), 8.84(d, 1H). |
| 59 | 0.94(s, 6H), 1.26(s, 6H), 2.45(s, 3H), 3.91(s, 2H), 7.03(m, 1H), 7.28-7.37(m, 3H), 7.40(m, 1H), 7.53(d, 1H), 7.61(t, 1H), 7.80-7.88(m, 4H), 8.16(d, 1H), 8.40(d, 1H), 9.27(d, 1H). |
| 60 | 1.37(s, 6H), 1.98(t, 1H), 2.98(t, 1H), 6.72(d, 1H), 7.08(d, 1H), 7.17(t, 1H), 7.47-7.65(m, 3H), 8.02(dd, 1H). |

TABLE 30-continued

| Compound No | ¹H-NMR |
|---|---|
| 61 | 6.96(m, 1H), 7.16-7.32(m, 2H), 7.39-7.49(m, 3H), 7.57(m, 1H), 7.99(d, 1H), 8.45(br, 1H). |
| 67 | 1.72 (s, 6H), 2.77 (s, 3H), 3.01 (br, 1H), 6.79 (d, 1H), 7.13-7.25 (m, 2H), 7.43-7.49 (m, 2H), 7.59-7.67 (m, 3H), 8.05 (d, 1H). |
| 68 | 1.43 (d, 6H), 1.73 (s, 6H), 3.01 (s, 1H), 3.64 (m, 1H), 6.78 (d, 1H), 7.12-7.25 (m, 2H), 7.41-7.46 (m, 2H), 7.58-7.65 (m, 3H), 8.08 (d, 1H). |
| 69 | 1.70 (s, 3H), 3.57 (s, 1H), 4.11 (s, 3H), 6.83 (d, 1H), 7.11-7.23 (m, 2H), 7.38 (t, 1H), 7.54-7.62 (m, 4H), 7.88 (d, 1H). |

TABLE 31

| Compound No. | ¹H-NMR |
|---|---|
| 70 | 1.35 (t, 3H), 1.71 (s, 6H), 3.61 (s, 1H), 4.56 (q, 2H), 6.84 (d, 1H), 7.11-7.20 (m, 2H), 7.39 (t, 1H), 7.53-7.63 (m, 4H), 7.85 (d, 1H). |
| 72 | 1.26 (s, 3H), 1.36 (s, 3H), 1.76 (s, 3H), 2.17 (s, 1H), 4.01 (s, 1H), 6.89 (d, 1H), 7.17-7.28 (m, 2H), 7.54 (t, 1H), 7.60-7.71 (m, 4H), 8.11 (d, 1H), 8.78 (d, 1H). |
| 73 | 1.15 (t, 3H), 1.86 (s, 3H), 3.80 (s, 1H), 3.94-4.08 (m, 2H), 6.95 (d, 1H), 7.23-7.37 (m, 2H), 7.49-7.55 (m, 2H), 7.61-7.71 (m, 3H), 8.10 (d, 1H), 8.72 (d, 1H). |
| 74 | 2.04 (s, 3H), 4.27 (s, 1H), 6.60 (d, 1H), 6.94-7.04 (m, 3H), 7.10-7.46 (m, 8H), 8.31 (d, 1H). |
| 75 | 1.84 (d, 3H), 3.12 (d, 1H), 3.36 (d, 1H), 4.17 (d, 1H), 6.50 (d, 1H), 6.89-7.50 (m, 11H), 8.51 (d, 1H). |
| 76 | 1.83 (d, 3H), 3.92 (d, 1H), 5.01 (d, 1H), 5.16 (d, 1H), 6.25 (dd, 1H), 6.69 (d, 1H), 6.95 (dd, 1H), 7.22 (m, 1H), 7.33 (m, 1H), 7.47-7.50 (m, 2H), 7.56 (d, 1H), 8.76 (d, 1H). |
| 77 | 1.74 (d, 3H), 2.62 (m, 1H), 2.89 (m, 1H), 3.87 (d, 1H), 5.10 (d, 1H), 5.78 (m, 1H), 6.69 (d, 1H), 6.94 (dd, 1H), 7.19 (m, 1H), 7.33 (m, 1H), 7.48-4.50 (m, 2H), 7.58 (d, 1H), 8.82 (d, 1H). |
| 78 | 1.84 (d, 3H), 3.97 (d, 1H), 5.03 (d, 1H), 5.17 (d, 1H), 5.71 (dd, 1H), 6.27 (dd, 1H), 6.58 (d, 1H), 6.76 (dd, 1H), 6.93 (dd, 1H), 7.16-7.42 (m, 5H), 7.46 (d, 1H). |
| 79 | 1.73 (d, 3H), 2.62 (m, 1H), 2.86 (m, 1H), 3.89-3.95 (m, 3H), 5.07-5.20 (m, 4H), 5.82 (m, 1H), 6.18 (m, 1H), 6.64 (d, 1H), 6.94 (dd, 1H), 7.16-7.41 (m, 5H). |
| 80 | 0.95 (d, 3H), 0.99 (d, 3H), 1.67 (d, 3H), 2.30 (m, 1H), 3.81 (d, 1H), 6.67 (d, 1H), 6.94 (m, 1H), 7.17 (m, 1H), 7.33 (m, 1H), 7.45-7.51 (m, 2H), 7.61 (d, 1H), 8.81 (d, 1H). |
| 81 | 1.75 (s, 3H), 1.85 (d, 3H), 4.00 (d, 1H), 4.77 (s, 1H), 4.95 (s, 1H), 6.68 (d, 1H), 6.95 (m, 1H), 7.22 (m, 1H), 7.35 (m, 1H), 7.48-7.51 (m, 2H), 7.57 (d, 1H), 8.72 (d, 1H). |
| 82 | 1.81 (d, 3H), 3.09 (d, 1H), 3.35 (d, 1H), 4.13 (s, 1H), 6.57 (d, 1H), 6.80-7.04 (m, 6H), 7.10-7.51 (m, 4H), 8.65 (d, 1H). |
| 83 | 1.09 (d, 3H), 1.67-1.70 (m, 3H), 2.84 (t, 2/3H), 2.95 (t, 1/3H), 3.72 (d, 1/3H), 3.94 (d, 2/3H), 4.97-5.10 (m, 2H), 5.78-5.95 (m, 1H), 6.68 (d, 1H), 6.90-6.96 (m, 1H), 7.16-7.25 (m, 1H), 7.31-7.38 (m, 1H), 7.47-7.50 (m, 2H), 7.59-7.62 (m, 1H), 8.81-8.83 (m, 1H). |
| 86 | 0.39-0.45 (m, 3H), 0.55 (m, 1H), 1.51 (dd, 1H), 1.73 (d, 3H), 3.74 (d, 1H), 6.68 (m, 1H), 6.95 (m, 1H), 7.22 (m, 1H), 7.35 (m, 1H), 7.47-7.50 (m, 2H), 7.59 (d, 1H), 8.82 (d, 1H). |
| 87 | 0.40-0.51 (m, 3H), 0.59 (m, 1H), 1.09 (m, 2H), 1.38 (m, 2H), 1.55 (m, 1H), 1.76 (d, 3H), 2.54 (m, 1H), 4.08 (d, 1H), 6.62 (d, 1H), 6.91 (dd, 1H), 7.13-7.40 (m, 4H), 7.45 (s, 1H). |
| 88 | 0.95 (t, 3H), 1.73 (d, 3H), 1.98 (m, 1H), 2.08 (m, 1H), 2.79 (s, 3H), 3.96 (d, 1H), 6.58 (d, 1H), 6.92 (m, 1H), 7.19 (m, 1H), 7.29-7.46 (m, 4H). |
| 89 | 1.74 (d, 3H), 2.76 (s, 3H), 3.99 (d, 1H), 5.02 (d, 1H), 5.18 (d, 1H), 6.28 (m, 1H), 6.58 (d, 1H), 6.94 (m, 1H), 7.21 (m, 1H), 7.29-7.42 (m, 4H). |
| 90 | 0.39-0.47 (m, 3H), 0.58 (m, 1H), 1.50 (m, 1H), 1.74 (d, 3H), 2.80 (s, 3H), 3.85 (d, 1H), 6.59 (d, 1H), 6.95 (m, 1H), 7.18 (m, 1H), 7.28-7.46 (m, 4H). |

TABLE 32

| Compound No. | ¹H-NMR |
|---|---|
| 91 | 1.83 (d, 3H), 2.63 (s, 3H), 3.06 (d, 1H), 3.30 (d, 1H), 3.67 (s, 3H), 4.21 (br, 1H), 6.43 (d, 1H), 6.68 (d, 2H), 6.89-6.96 (m, 3H), 7.16 (m, 1H), 7.27-7.41 (m, 4H). |
| 92 | 1.82 (d, 3H), 2.64 (s, 3H), 3.10 (d, 1H), 3.34 (d, 1H), 4.25 (br, 1H), 6.45 (d, 1H), 6.81-7.02 (m, 6H), 7.17 (m, 1H), 7.26-7.42 (m, 3H). |
| 94 | 1.78 (d, 6H), 2.74 (s, 3H), 2.81 (s, 3H), 4.23 (d, 1H), 6.52 (d, 1H), 6.86 (dd, 1H), 7.10 (m, 1H), 7.37 (t, 1H), 7.48-7.51 (m, 3H). |
| 97 | 1.81 (s, 6H), 2.82 (s, 3H), 4.02 (s, 1H), 6.80 (dd, 1H), 7.17 (m, 1H), 7.26-7.32 (m, 3H), 7.37-7.40 (m, 2H). |
| 101 | 1.68 (s, 6H), 2.40 (s, 3H), 6.82 (d, 1H), 7.07 (m, 1H), 7.2-7.6 (m, 5H), 8.86 (d, 1H). |
| 103 | 1.82 (s, 6H), 4.12 (s, 1H), 6.86 (dd, 1H), 7.15 (m, 1H), 7.28 (m, 1H), 7.47-7.56 (m, 2H), 7.62-7.70 (m, 2H), 8.10 (d, 1H), 8.77 (d, 1H). |
| 105 | 1.76 (d, 3H), 2.76 (s, 3H), 3.93 (d, 1H), 6.58 (d, 1H), 6.92 (m, 1H), 7.13-7.27 (m, 2H), 7.35-7.42 (m, 2H), 8.02 (m, 1H). |
| 107 | 1.78 (d, 6H), 2.75 (s, 3H), 6.55 (m, 1H), 6.89 (m, 1H), 7.14 (m, 1H), 7.4-7.7 (m, 4H), 8.05 (dd, 1H). |
| 108 | 1.82 (s, 6H), 2.77 (s, 3H), 4.18 (s, 1H), 6.77 (dd, 1H), 7.13 (m, 1H), 7.25-7.35 (m, 2H), 7.46 (m, 1H), 7.59-7.64 (m, 2H), 8.04 (d, 1H). |
| 111 | 2.62 (s, 3H), 6.75 (d, 1H), 6.96 (t, 1H), 7.36 (m, 1H), 7.55 (t, 1H), 7.61 (d, 1H), 7.65-7.76 (m, 2H), 8.12 (d, 1H), 8.79 (d, 1H). |

TABLE 32-continued

| Compound No. | ¹H-NMR |
| --- | --- |
| 113 | 0.20 (s, 9H), 6.73 (d, 1H), 6.97 (m, 1H), 7.36 (m, 1H), 7.54-7.77 (m, 4H), 8.12 (d, 1H), 8.71 (d, 1H). |
| 118 | 1.76 (d, 3H), 2.74 (s, 3H), 3.92 (d, 1H), 6.55 (m, 1H), 6.91 (m, 1H), 7.17 (m, 1H), 7.41-7.51 (m, 2H), 7.57 (d, 1H), 8.04 (d, 1H). |
| 119 | 1.77 (d, 6H), 3.88 (d, 1H), 6.63 (m, 1H), 7.04 (m, 1H), 7.53-7.59 (m, 2H), 7.65-7.73 (m, 2H), 8.12 (d, 1H), 8.79 (d, 1H). |
| 126 | 1.77 (d, 6H), 3.97 (d, 1H), 6.64 (m, 1H), 6.91 (m, 1H), 7.17 (dt, 1H), 7.36 (dt, 1H), 7.63 (d, 1H), 7.68-7.77 (m, 2H), 8.80 (d, 1H). |
| 131 | 2.17-2.25 (m, 2H), 2.83-2.93 (m, 1H), 3.16-3.27 (m, 1H), 3.33 (s, 3H), 4.88 (t, 1H), 6.84 (d, 1H), 7.14 (d, 1H), 7.30 (d, 1H), 7.48-7.54 (m, 2H), 7.59-7.68 (m, 2H), 8.10 (d, 1H), 8.85 (d, 1H). |
| 132 | 1.44 (d, 3H), 3.25 (s, 3H), 4.73 (q, 1H), 6.96-6.99 (m, 1H), 7.26-7.33 (m, 2H), 7.41 (d, 1H), 7.51 (t, 1H), 7.58-7.66 (m, 3H), 8.10 (d, 1H), 8.82(d, 1H). |
| 133 | 0.99 (t, 3H), 2.16-2.25 (m, 1H), 2.88-2.92 (m, 1H), 3.16-3.25 (m, 1H), 3.35-3.43 (m, 1H), 3.48-3.56 (m, 1H), 4.97 (dd, 1H), 6.87 (d, 1H), 7.13 (d, 1H), 7.29 (t, 1H), 7.46-7.52 (m, 2H), 7.58-7.67 (m, 2H), 8.09 (d, 1H), 8.84 (d, 1H). |
| 134 | 0.74 (t, 3H), 1.35-1.43 (m, 2H), 2.17-2.25 (m, 2H), 2.89 (m, 1H), 3.22 (m, 1H), 3.29 (m, 1H), 3.44 (m, 1H), 4.98 (m, 1H), 6.85 (d, 1H), 7.13 (d, 1H), 7.29 (t, 1H), 7.46-7.52 (m, 2H), 7.58-7.67 (m, 2H), 8.10 (d, 1H), 8.84 (d, 1H). |

TABLE 33

| Compound No. | ¹H-NMR |
| --- | --- |
| 135 | 0.87 (t, 3H), 1.43 (d, 3H), 1.54 (m, 2H), 3.28 (m, 2H), 4.81 (m, 1H), 6.95 (m 1H), 7.26-7.30 (m, 2H), 7.39 (d, 1H), 7.51 (m, 1H), 7.59-7.66 (m, 3H), 8.10 (d, 1H), 8.82(d, 1H). |
| 136 | 1.00 (s, 9H), 1.99 (br, 1H), 4.89 (d, 1H), 6.91 (d, 1H), 7.23 (m, 1H), 7.48 (d, 1H), 7.53 (d, 1H), 7.60-7.68 (m, 4H), 8.10 (d, 1H), 8.80 (d, 1H). |
| 137 | 2.11 (m, 1H), 2.49 (m, 1H), 2.85 (br, 1H), 2.91 (m, 1H), 3.20 (m, 1H), 5.50 (m, 1H), 6.76 (d, 1H), 7.11 (d, 1H), 7.26 (t, 1H), 7.52 (t, 1H), 7.55-7.71 (m, 3H), 8.13 (d, 1H), 8.82 (s, 1H). |
| 140 | 1.60 (d, 3H), 3.24 (s, 3H), 4.86 (q, 1H), 6.78 (d, 1H), 7.01 (t, 1H), 7.25-7.35 (m, 2H), 7.42-7.50 (m, 3H), 8.83 (d, 1H). |
| 142 | 1.61 (d, 3H), 3.18 (s, 3H), 5.03 (q, 1H), 6.94 (dd, 1H), 7.15 (t, 1H), 7.27-7.37 (m, 2H), 7.41-7.49 (m, 2H), 8.81 (d, 1H). |
| 143 | 0.44-0.67 (m, 4H), 1.62 (m, 1H), 2.86 (d, 1H), 4.57 (t, 1H), 6.84 (dd, 1H), 7.20 (t, 1H), 7.26 (m, 1H), 7.34 (m, 1H), 7.47-7.50 (m, 2H), 7.61 (d, 1H), 8.86 (d, 1H). |
| 145 | 1.10 (s, 9H), 3.32 (d, 1H), 5.18 (d, 1H), 6.76 (dd, 1H), 7.14 (t, 1H), 7.24 (m, 1H), 7.37 (m, 1H), 7.47-7.53 (m, 2H), 7.71 (d, 1H), 8.83 (d, 1H). |
| 146 | 1.65 (d, 3H), 2.99 (d, 1H), 5.50 (m, 1H), 6.81 (d, 1H), 7.15-7.27 (m, 2H), 7.36 (m, 1H), 7.48-7.50 (m, 2H), 7.60 (m, 1H), 8.86 (d, 1H). |
| 147 | 1.62 (d, 3H), 3.20 (s, 3H), 5.07 (q, 1H), 6.91 (dd, 1H), 7.22-7.35 (m, 3H), 7.41-7.49 (m, 3H), 8.81 (d, 1H). |
| 148 | 1.65 (d, 3H), 3.00 (d, 1H), 5.47 (m, 1H), 6.84 (d, 1H), 7.10 (t, 1H), 7.30-7.51 (m, 4H), 7.61 (d, 1H), 8.86 (d, 1H). |
| 149 | 1.61 (d, 3H), 3.19 (s, 3H), 5.06 (q, 1H), 6.96 (d, 1H), 7.17 (t, 1H), 7.28 (m, 1H), 7.43-7.51 (m, 4H), 8.81 (d, 1H). |
| 150 | 1.50 (d, 3H), 2.54 (s, 3H), 3.16 (s, 3H), 4.92 (q, 1H), 6.84 (d, 1H), 7.08 (d, 1H), 7.21 (t, 1H), 7.26-7.34 (m, 2H), 7.38-7.46 (m, 2H), 8.84 (d, 1H). |
| 152 | 1.61 (d, 3H), 2.83 (s, 3H), 3.16 (s, 3H), 5.05 (q, 1H), 6.85 (dd, 1H), 7.21-7.32 (m, 4H), 7.34-7.40 (m, 2H). |
| 153 | 1.63 (d, 3H), 3.29 (s, 3H), 4.97 (q, 1H), 7.18 (d, 1H), 7.32-7.51 (m, 5H), 7.61 (d, 1H), 8.83 (d, 1H). |
| 154 | 1.62 (d, 3H), 3.22 (s, 3H), 4.09 (s, 3H), 5.08 (q, 1H), 6.91 (d, 1H), 6.97 (m, 1H), 7.13 (t, 1H), 7.25 (m, 1H), 7.41-7.47 (m, 3H), 8.76 (d, 1H). |
| 155 | 1.58 (d, 3H), 3.20 (s, 3H), 3.90 (s, 3H), 4.09 (s, 3H), 5.00 (q, 1H), 6.58 (d, 1H), 6.78 (d, 1H), 6.95 (d, 1H), 7.21-7.28 (m, 2H), 7.39-7.4 (m, 2H), 8.78 (br, 1H). |
| 156 | 1.63 (d, 3H), 3.82 (d, 2H), 4.98 (dd, 1H), 5.15 (dd, 1H), 5.21 (q, 1H), 5.70 (m, 1H), 6.92 (dd, 1H), 7.24-7.33 (m, 3H), 7.39-7.49 (m, 3H), 8.82 (d, 1H). |
| 157 | 1.02 (t, 3H), 1.92-2.08 (m, 2H), 2.84 (d, 1H), 5.23 (m, 1H), 6.80 (dd, 1H), 7.18 (t, 1H), 7.24 (m, 1H), 7.35 (m, 1H), 7.45-7.51 (m, 2H), 7.60 (m, 1H), 8.84 (d, 1H). |

TABLE 34

| Compound No. | ¹H-NMR |
| --- | --- |
| 160 | 1.65 (d, 3H), 4.33 (d, 1H), 4.38 (d, 1H), 5.25 (d, 1H), 6.93 (dd, 1H), 7.13 (m 5H), 7.25-7.42 (m, 6H), 8.79 (d, 1H). |
| 161 | 6.56 (d, 1H), 6.78 (m, 1H), 7.2-7.5 (m, 11H), 8.50 (d, 1H). |
| 163 | 0.85 (t, 3H), 1.2-1.4 (m, 4H), 1.9-2.1 (m, 2H), 2.90 (d, 1H), 5.31 (m, 1H), 6.80 (dd, 1H), 7.1-7.6 (m, 6H), 8.83 (d, 1H). |
| 164 | 2.25 (m, 1H), 3.53 (d, 1H), 6.07 (dd, 1H), 6.86 (m, 1H), 7.2-7.7 (m, 6H), 8.85 (d, 1H). |
| 165 | 0.13 (s, 9H), 6.45 (s, 1H), 6.94 (d, 1H), 7.29-7.38 (m, 3H), 7.48-7.50 (m, 2H), 7.59 (m, 1H), 8.86 (d, 1H). |

TABLE 34-continued

| Compound No. | $^1$H-NMR |
|---|---|
| 167 | 1.62 (d, 3H), 3.20 (s, 3H), 5.08 (q, 1H), 6.91 (dd, 1H), 7.21-7.34 (m, 3H), 7.42-7.47 (m, 3H), 8.81 (d, 1H). |
| 168 | 3.51 (s, 3H), 3.65 (s, 3H), 5.44 (s, 1H), 6.89 (m, 1H), 7.2-7.6 (m, 6H), 8.78 (d, 1H). |
| 170 | 0.02 (s, 9H), 2.26 (s, 3H), 5.52 (s, 1H), 6.86 (dd, 1H), 7.2-7.6 (m, 6H), 8.75 (d, 1H). |
| 171 | 2.22 (s, 3H), 4.13 (d, 1H), 5.66 (d, 1H), 6.91 (m, 1H), 7.3-7.6 (m, 6H), 8.76 (d, 1H). |
| 172 | 2.34 (s, 3H), 3.46 (s, 3H), 5.28 (s, 1H), 6.9 (m, 1H), 7.2-7.26 (m, 6H), 8.81 (d, 1H). |
| 173 | 1.26 (s, 3H), 1.45 (s, 3H), 3.67 (d, 1H), 5.27 (d, 1H), 6.83 (d, 1H), 7.1-7.5 (m, 6H), 7.66 (bs, 1H), 8.82 (d, 1H). |
| 174 | 2.97 (d, 1H), 3.31 (m, 2H), 5.59 (m, 1H), 6.75 (d, 1H), 7.13-7.49 (m, 11H), 8.77 (br, 1H). |
| 175 | 3.19 (s, 3H), 3.28-3.44 (m, 2H), 5.18 (t, 1H), 6.82 (d, 1H), 7.11-7.49 (m, 11H), 8.67 (br, 1H). |
| 177 | 1.60 (d, 3H), 3.17 (s, 3H), 5.04 (q, 1H), 6.97 (dd, 1H), 7.13 (t, 1H), 7.26-7.36 (m, 2H), 7.42-7.49 (m, 2H), 8.81 (d, 1H). |
| 180 | 1.23 (s, 3H), 1.40 (s, 3H), 3.20 (s, 3H), 4.87 (s, 1H), 6.94 (d, 1H), 7.26-7.35 (m, 3H), 7.45-7.48 (m, 3H), 8.75 (d, 1H). |
| 181 | 3.59 (d, 1H), 3.70 (s, 3H), 5.79 (d, 1H), 6.8-6.95 (m, 1H), 7.2-7.6 (m, 6H), 8.77 (d, 1H). |
| 185 | 1.71 (t, 3H), 3.06 (m, 1H), 5.34 (m, 1H), 7.08 (d, 1H), 7.32-7.41 (m, 2H), 7.49-7.52 (m, 3H), 7.67 (dd, 1H), 8.86 (d, 1H). |
| 186 | 1.67 (d, 3H), 3.16 (s, 3H), 4.85 (q, 1H), 7.21 (d, 1H), 7.32 (m, 1H), 7.41-7.47 (m, 4H), 7.58 (d, 1H), 8.80 (d, 1H). |
| 188 | 1.63 (d, 3H), 3.23 (s, 3H), 5.10 (q, 1H), 6.89 (dd, 1H), 7.18-7.29 (m, 2H), 7.45 (d, 1H), 7.52 (t, 1H), 7.60-7.69 (m, 2H), 8.10 (d, 1H), 8.78 (d, 1H). |
| 189 | 1.48 (d, 3H), 1.97 (d, 1H), 5.17 (m, 1H), 7.15 (m, 1H), 7.24-7.35 (m, 2H), 7.45-7.52 (m, 2H), 7.58-7.63 (m, 2H), 8.09 (d, 1H), 8.87 (d, 1H). |
| 190 | 1.61 (d, 3H), 2.69 (m, 1H), 5.43 (m, 1H), 7.09 (t, 1H), 7.27-7.34 (m, 2H), 7.52 (t, 1H), 7.60-7.67 (m, 2H), 8.10 (d, 1H), 8.87 (d, 1H). |
| 198 | 1.61 (d, 3H), 2.83 (s, 3H), 3.16 (s, 3H), 5.04 (q, 1H), 6.84 (dd, 1H), 7.19-7.36 (m, 5H). |

TABLE 35

| Compound No | $^1$H-NMR |
|---|---|
| 203 | 1.62 (d, 3H), 3.22 (s, 3H), 5.09 (q, 1H), 6.87 (dd, 1H), 7.1-7.4 (m, 3H), 7.46 (d, 1H), 7.6-7.8 (m, 2H), 8.78 (d, 1H). |
| 204 | 1.78 (s, 3H), 3.74 (s, 3H), 4.14 (d, 1H), 5.85 (d, 1H), 6.93 (m, 1H), 7.2-7.5 (m, 6H), 8.78 (d, 1H). |
| 206 | 1.77 (d, 1H), 2.71 (s, 3H), 5.52 (m, 1H), 6.24 (dd, 1H), 6.83 (m, 1H), 7.07 (m, 1H), 7.42-7.77 (m, 2H), 7.80 (m, 1H). |
| 207 | 1.52 (dd, 3H), 2.29 (s, 6H), 3.95 (q, 1H), 6.78 (d, 1H), 6.97 (m, 1H), 7.23-7.34 (m, 2H), 7.43-7.47 (m, 3H), 8.84 (d, 1H). |
| 209 | 1.60 (d, 3H), 3.19 (s, 3H), 3.92 (s, 3H), 4.82 (q, 1H), 7.0-7.1 (m, 1H), 7.2-7.5 (m, 6H), 8.84 (d, 1H). |
| 210 | 1.59 (d, 3H), 2.59 (s, 3H), 3.23 (s, 3H), 4.76 (q, 1H), 6.99 (dd, 1H), 7.11 (dd, 1H), 7.2-7.5 (m, 5H), 8.85 (d, 1H). |
| 211 | 1.60 (d, 3H), 2.51 (s, 3H), 3.23 (s, 3H), 5.04 (q, 1H), 6.78 (dd, 1H), 7.12 (d, 1H), 7.2-7.5 (m, 5H), 8.83 (d, 1H). |
| 212 | 1.74 (d, 3H), 3.24 (s, 3H), 3.26 (s, 3H), 5.48 (q, 1H), 7.2-7.5 (m, 5H), 8.03 (d, 1H), 8.81 (d, 1H). |
| 215 | 1.60 (d, 3H), 3.02 (s, 3H), 4.48 (q, 1H), 7.02 (dd, 1H), 7.12 (dd, 1H), 7.2-7.55 (m, 10H), 8.85 (d, 1H). |
| 217 | 3.42 (s, 6H), 5.65 (s, 1H), 6.79 (d, 1H), 7.01 (t, 1H), 7.29-7.37 (m, 2H), 7.45-7.48 (m, 3H), 8.86 (d, 1H). |
| 218 | 1.11 (t, 6H), 3.49 (m, 2H), 3.74 (m, 2H), 5.78 (s, 1H), 6.80 (d, 1H), 7.01 (t, 1H), 7.27-7.36 (m, 2H), 7.43-7.49 (m, 3H), 8.86 (d, 1H). |
| 220 | 3.35 (s, 3H), 4.66 (s, 2H), 6.92 (dd, 1H), 7.29-7.35 (m, 3H), 7.44-7.46 (m, 3H), 8..88 (d, 1H). |
| 221 | 3.99 (m, 2H), 4.70 (s, 2H), 5.08 (d, 1H), 5.17 (d, 1H), 5.78 (m, 1H), 6.93 (dd, 1H), 7.28-7.35 (m, 3H), 7.44-7.49 (m, 3H), 8.88 (d, 1H). |
| 223 | 3.36 (s, 3H), 4.66 (s, 2H), 6.96 (d, 1H), 7.22 (t, 1H), 7.33 (m, 1H), 7.45-7.52 (m, 3H), 8.88 (d, 1H). |
| 224 | 0.83 (t, 3H), 1.30 (m, 2H), 1.40 (m, 2H), 2.60 (t, 2H), 3.99 (s, 2H), 6.90 (d, 1H), 7.20-7.37 (m, 3H), 7.44-7.50 (m, 3H), 8.87 (d, 1H). |
| 225 | 0.99 (s, 6H), 1.48 (s, 6H), 1.63 (d, 1H), 3.57 (d, 1H), 6.93 (d, 1H), 7.14-7.26 (m, 2H), 7.44-7.71 (m, 5H), 8.09 (d, 1H), 8.77 (br, 1H). |
| 226 | 0.95 (s, 6H), 1.42 (s, 6H), 2.43 (s, 3H), 4.01 (s, 2H), 6.87 (d, 1H), 7.11 (m, 1H), 7.20 (m, 1H), 7.28 (d, 2H), 7.40-7.54 (m, 3H), 7.59-7.74 (m, 4H), 8.10 (d, 1H), 8.68 (d, 1H). |
| 227 | 1.23 (s, 6H), 1.52 (s, 6H), 2.49 (s, 1H), 6.94 (d, 1H), 7.18-7.26 (m, 2H), 7.49-7.68 (m, 5H), 8.10 (d, 1H), 8.77 (d, 1H). |
| 230 | 0.87 (s, 3H), 1.04 (s, 3H), 1.22 (s, 3H), 1.52 (d, 6H), 1.68 (d, 1H), 4.08 (m, 1H), 6.94 (m, 1H), 7.15-7.26 (m, 2H), 7.46-7.54 (m, 2H), 7.59-7.68 (m, 3H), 8.10 (d, 1H), 8.78 (d, 1H). |
| 232 | 1.38 (s, 6H), 1.65 (s, 6H), 6.95 (m, 1H), 7.19-7.31 (m, 2H), 7.47 (d, 1H), 7.52 (m, 1H), 7.60-7.69 (m, 3H), 8.10 (d, 1H), 8.75 (d, 1H). |

TABLE 36

| Compound No | ¹H-NMR |
|---|---|
| 234 | 1.49 (s, 6H), 6.92 (m, 1H), 7.19-7.33 (m, 2H), 7.48-7.71 (m, 5H), 8.02 (d, 1H), 8.72 (d, 1H), 9.72 (s, 1H). |
| 235 | 1.05 (s, 6H), 1.57(s, 6H), 3.64 (d, 1H), 6.73 (d, 1H), 6.87 (m, 1H), 7.15 (m, 1H), 7.81-7.55 (m, 2H), 7.61-7.73 (m, 2H), 8.10 (d, 1H), 8.75 (d, 1H). |
| 243 | 1.08 (s, 6H), 1.52 (s, 6H), 2.26 (s, 2H), 6.88 (m, 1H), 7.17 (m, 1H), 7.36 (s, 2H), 7.50-7.70 (m, 4H), 8.81 (d, 1H), 8.91 (d, 1H). |
| 244 | 1.02 (br, 1H), 1.46 (s, 6H), 2.19 (t, 2H), 3.56 (m, 2H), 6.90 (d, 1H), 7.13-7.24 (m, 2H), 7.43 (d, 1H), 7.49-7.54 (m, 2H), 7.60-7.70 (m, 2H), 8.10 (d, 1H), 8.81 (d, 1H). |
| 246 | 1.06 (d, 3H), 1.50 (d, 6H), 1.96 (dd, 1H), 2.15 (dd, 1H), 3.83 (m, 1H), 6.89 (dd, 1H), 7.13-7.26 (m, 2H), 7.46-7.55 (m, 2H), 7.59-7.70 (m, 3H), 8.11 (d, 1H), 8.82 (d, 1H). |
| 247 | 1.47 (s, 6H), 2.21 (d, 2H), 3.16 (s, 6H), 4.19 (t, 1H), 6.87 (dd, 1H), 7.13-7.20 (m, 2H), 7.44 (m, 1H), 7.49 (t, 1H), 7.54-7.70 (m, 3H), 8.10 (d, 1H), 8.81 (d, 1H). |
| 248 | 0.99 (s, 6H), 1.49 (s, 6H), 3.43 (s, 6H), 3.95 (s, 1H), 6.93 (d, 1H), 7.12-7.24 (m, 2H), 7.42 (d, 1H), 7.48-7.67 (m, 4H), 8.09 (d, 1H), 8.78 (d, 1H). |
| 251 | 1.26 (s, 6H), 1.56 (s, 6H), 2.48 (s, 1H), 2.79 (s, 1H), 6.88 (m, 1H), 7.19-7.30 (m, 3H), 7.43 (t, 1H), 7.56-7.61 (m, 3H), 8.02 (d, 1H). |
| 252 | 0.97 (t, 1H), 1.47 (s, 6H), 2.19 (t, 2H), 2.84 (s, 3H), 3.57 (m, 1H), 6.83 (dd, 1H), 7.11-7.23 (m, 2H), 7.37 (t, 1H), 7.41-7.46 (m, 2H), 7.56-7.62 (m, 2H), 8.02 (d, 1H). |
| 253 | 1.09 (d, 3H), 1.40 (s, 3H), 1.45 (s, 3H), 1.72 (bs, 1H), 4.54 (m 1H), 6.89 (dd, 1H), 7.1-7.3 (m, 2H), 7.4-7.7 (m, 5H), 8.09 (d, 1H), 8.77 (d, 1H). |
| 254 | 0.91 (t, 3H), 1.2-1.5 (m, 8H), 1.6-1.7 (m, 1H), 4.1-4.2 (m, 1H), 6.90 (dd, 1H), 7.1-7.3 (m, 2H), 7.4-7.7 (m, 5H), 8.10 (d, 1H), 8.77 (d, 1H). |
| 255 | 1.43 (s, 3H), 1.49 (s, 3H), 1.57 (s, 3H), 1.75 (d, 1H), 4.8-5.0 (m, 3H) 6.91 (dd, 1H), 7.1-7.3 (m, 2H), 7.4-7.7 (m, 5H), 8.10 (d, 1H), 8.81 (d, 1H). |
| 256 | 0.89 (s, 3H), 1.05-1.10 (m, 6H), 1.23 (br, 6H), 2.81 (s, 3H), 4.09 (m, 1H), 6.88 (d, 1H), 7.18-7.26 (m, 3H), 7.42 (t, 1H), 7.55-7.64 (m, 3H), 8.01 (d, 1H). |
| 257 | 1.24 (s, 6H), 1.53 (br, 6H), 1.88 (s, 3H), 2.83 (s, 3H), 6.87 (d, 1H), 7.13-7.26 (m, 3H), 7.41-7.46 (m, 2H), 7.56-7.60 (m, 2H), 8.03 (d, 1H). |
| 258 | 1.11 (br, 1H), 1.45 (s, 6H), 2.37 (t, 2H), 3.55 (m, 2H), 6.90 (m, 1H), 7.15-7.34 (m, 3H), 7.42-7.46 (m, 3H), 7.53 (d, 1H), 8.84 (d, 1H). |
| 259 | 0.98 (br, 1H), 1.46 (s, 6H), 2.17 (t, 2H), 2.86 (s, 3H), 3.57 (m, 2H), 6.86 (d, 1H), 7.15-7.30 (m, 3H), 7.36-7.37 (m, 3H), 7.45 (m, 1H). |
| 260 | 1.51 (s, 6H), 2.11 (s, 3H), 6.91 (dd, 1H), 7.2-7.3 (m, 2H), 7.5-7.7 (m, 5H), 8.11 (d, 1H), 8.71 (d, 1H). |
| 261 | 1.47 (s, 6H), 2.28 (t, 2H), 2.84 (s, 3H), 3.66 (s, 3H), 4.04 (t, 2H), 6.84 (m, 1H), 7.12-7.28 (m, 3H), 7.30-7.45 (m, 4H). |

TABLE 37

| Compound No. | ¹H-NMR |
|---|---|
| 262 | 1.59 (s, 6H), 2.18 (s, 3H), 6.72 (m, 1H), 6.96 (m, 1H), 7.2-7.6 (m, 5H), 8.73 (d, 1H). |
| 263 | 1.3 (s, 6H), 1.63 (s, 6H), 6.74 (d, 1H), 6.91 (m, 1H), 7.18 (m, 1H), 7.5-7.8 (m, 4H), 8.10 (d, 1H), 8.75 (d, 1H). |
| 265 | 1.60 (s, 6H), 2.18 (s, 3H), 6.70 (d, 1H), 6.92 (m, 1H), 7.20 (m, 1H), 7.5-7.8 (m, 2H), 8.10 (d, 1H), 8.69 (d, 1H). |
| 266 | 1.59 (d, 6H), 2.18 (s, 3H), 6.68 (d, 2H), 6.92 (dd, 1H), 6.96-7.24 (m, 1H), 7.31-7.37 (m, 1H), 7.55 (d, 1H), 7.67-7.75 (m, 2H), 8.69 (d, 1H). |
| 267 | 1.59 (d, 6H), 2.18 (s, 3H), 6.70 (d, 1H), 6.96 (dd, 1H), 7.19-7.25 (m, 1H), 7.40-7.49 (m, 2H), 7.53 (d, 1H), 8.75 (d, 1H). |
| 268 | 0.87 (d, 3H), 1.39 (s, 3H), 1.44 (s, 3H), 1.85 (s, 1H), 4.50 (m 1H), 6.91 (d, 1H), 7.16-7.33 (m, 3H), 7.43-7.52 (m, 3H), 8.81 (d, 1H). |
| 269 | 1.51 (s, 6H), 2.14 (s, 3H), 6.92 (d, 1H), 7.22-7.36 (m, 3H), 7.44-7.48 (m, 2H), 7.50-7.58 (m, 2H), 8.73 (d, 1H). |
| 270 | 1.88 (s, 6H), 2.86 (s, 3H), 6.88 (d, 1H), 7.18-7.43 (m, 5H), 7.50-7.56 (m, 2H). |
| 271 | 1.89 (s, 6H), 6.93 (d, 1H), 7.20 (m, 1H), 7.31 (m, 1H), 7.54 (t, 1H), 7.63-7.73 (m, 2H), 8.12 (d, 1H), 8.83 (d, 1H). |
| 277 | 0.82 (t, 3H), 1.20 (t, 3H), 1.64 (m, 1H), 3.04 (m, 1H), 6.98 (m, 1H), 7.19-7.26 (m, 2H), 7.32-7.39 (m, 2H), 7.49 (t, 1H), 7.52-7.65 (m, 2H), 8.10 (d, 1H), 8.83 (br, 1H). |
| 278 | 0.79 (d, 3H), 0.94 (d, 3H), 1.21 (d, 3H), 1.78-1.90 (m, 1H), 2.80-2.90 (m, 1H), 6.94-6.99 (m, 1H), 7.18-7.4 (m, 2H), 7.35 (d, 1H), 7.49 (t, 1H), 7.58-7.65 (m, 3H), 8.09 (d, 1H), 8.93 (br, 1H). |
| 280 | 2.24 (s, 3H), 2.72 (s, 3H), 4.13 (d, 1H), 5.51 (d, 1H), 6.69 (d, 1H), 7.02 (t, 1H), 7.2-7.6 (m, 5H). |
| 286 | 1.73-1.82 (m, 4H), 2.66-2.70 (m, 2H), 2.82-2.84 (m, 2H), 6.82 (d, 1H), 6.98 (d, 1H), 7.13 (t, 1H), 7.31 (d, 1H), 7.48-7.76 (m, 4H), 8.07-8.14 (m, 2H), 8.83 (d, 1H). |
| 289 | 1.26 (t, 3H), 4.25 (q, 2H), 6.73 (d, 1H), 7.01 (t, 1H), 7.41 (m, 1H), 7.56 (t, 1H), 7.63 (d, 1H), 7.66-7.75 (m, 2H), 8.12 (d, 1H), 8.74 (d, 1H). |
| 295 | 3.13 (s, 3H), 3.63 (s, 3H), 6.76 (d, 1H), 7.03 (m, 1H), 7.31-7.52 (m, 4H), 7.60 (dd, 1H), 8.78 (d, 1H). |
| 297 | 1.01 (m, 2H), 1.31 (m, 2H), 4.53 (s, 2H), 6.79 (d, 1H), 6.98 (t, 1H), 7.08-7.11 (m, 2H), 7.16-7.18 (m, 3H), 7.28-7.49 (m, 5H), 8.87 (d, 1H). |
| 308 | 1.66 (s, 3H), 2.93 (d, 1H), 2.99 (d, 1H), 6.74 (d, 1H), 6.95 (t, 1H), 7.26-7.36 (m, 2H), 7.46-7.48 (m, 2H), 7.54 (d, 1H), 8.85 (d, 1H). |
| 328 | 3.45 (s, 6H), 4.54 (s, 2H), 5.93 (s, 1H), 7.04 (d, 1H), 7.17 (t, 1H), 7.27 (m, 1H), 7.31 (m, 1H), 7.43 (m, 1H), 7.50 (m, 1H), 7.85 (s, 1H), 8.86 (d, 1H). |

TABLE 37-continued

| Compound No. | ¹H-NMR |
|---|---|
| 329 | 1.27 (t, 3H), 4.26 (q, 2H), 4.60 (s, 2H), 7.27-7.52 (m, 6H), 7.81 (s, 1H), 7.99 (d, 1H), 8.88 (d, 1H). |
| 330 | 1.18 (t, 3H), 4.24 (q, 2H), 4.30 (s, 2H), 7.01-7.07 (m, 2H), 7.35 (m, 1H), 7.51 (t, 1H), 7.67 (t, 1H), 7.72 (d, 1H), 7.85 (s, 1H), 8.07 (d, 1H), 8.78 (d, 1H). |

TABLE 38

| Compound No. | ¹H-NMR |
|---|---|
| 331 | 1.15 (t, 3H), 4.09 (q, 2H), 4.28 (s, 2H), 7.02-7.07 (m, 2H), 7.27-7.40 (m, 2H), 7.68-7.83 (m, 2H), 8.16 (d, 1H), 8.78 (d, 1H). |
| 334 | 5.28-5.61 (m, 2H), 5.83-6.12 (m, 2H), 7.18-7.42 (m, 4H), 7.54-8.10 (m, 4H), 8.47 (dd, 1H), 9.02 (d, 1H). |
| 339 | 1.55 (d, 3H), 1.68 (d, 3H), 6.14 (s, 1H), 7.32-7.41 (m, 2H), 7.51-7.63 (m, 3H), 7.81-7.88 (m, 2H). 8.16 (d, 1H), 8.44 (d, 1H), 9.24 (d, 1H). |
| 340 | 7.52-7.67 (m, 5H), 7.83-7.88 (m, 2H), 7.96 (m, 1H), 8.08 (d, 1H), 8.18-8.21 (m, 2H), 8.53 (d, 1H), 9.42 (d, 1H). |
| 343 | 5.94 (dd, 1H), 6.22 (dd, 1H), 6.89 (dd, 1H), 7.54-7.87 (m, 7H), 8.14 (m, 1H), 8.47 (d, 1H), 9.28 (d, 1H). |
| 344 | 1.66 (s, 3H), 3.02 (s, 2H), 4.50 (m, 1H), 4.70 (m, 1H), 7.31-7.71 (m, 7H), 8.50 (m, 1H), 9.33 (d, 1H). |
| 345 | 3.07 (t, 2H), 3.58 (t, 2H), 7.35-7.71 (m, 5H), 7.84-7.91 (m, 2H), 8.19 (d, 1H), 8.50 (d, 1H), 9.36 (d, 1H). |
| 347 | 1.64 (s, 3H), 3.53 (s, 2H), 4.40 (m, 1H), 4.64 (m, 1H), 7.17 (dd, 1H), 7.26-7.42 (m, 2H), 7.63 (m, 1H), 7.82-7.90 (m, 2H), 8.18 (m, 1H), 8.46 (d, 1H), 9.30 (d, 1H) |
| 350 | 1.67 (d, 3H), 1.75 (d, 3H), 2.60 (bs, 1H), 5.04 (bs, 1H), 6.54 (s, 1H), 7.02-7.10 (m, 2H), 7.18-7.55 (m, 5H), 8.04 (s, 1H), 8.85 (d, 1H). |
| 351 | 3.94-4.00 (m, 2H), 5.12-5.26 (m, 3H), 5.75 (d, 1H), 6.09 (m, 1H), 6.49 (dd, 1H), 7.10 (m, 1H), 7.38-7.53 (m, 3H), 7.69-7.76 (m, 3H), 8.00 (d, 1H), 8.12 (d, 1H), 9.48 (d, 1H). |
| 352 | 1.17 (t, 3H), 4.20 (q, 2H), 6.94 (d, 1H), 7.31 (t, 1H), 7.55-7.61 (m, 2H), 7.67-7.77 (m, 3H), 8.04 (d, 1H), 8.14 (d, 1H), 8.80 (br, 1H). |
| 353 | 2.61 (s, 3H), 6.90 (d, 1H), 7.28-7.38 (m, 3H), 7.45-7.51 (m, 2H), 7.58 (m, 1H), 8.86 (d, 1H). |
| 355 | 2.61 (s, 3H), 6.93 (d, 1H), 7.23-7.37 (m, 2H), 7.43-7.49 (m, 3H), 7.57 (s, 1H), 8.82 (br, 1H). |
| 359 | 2.61 (s, 3H), 2.74 (s, 3H), 6.78 (dd, 1H), 7.24-7.46 (m, 5H), 7.46 (s, 1H). |
| 360 | 1.24 (d, 6H), 3.16 (sep, 1H), 6.88 (d, 1H), 7.2-7.6 (m, 6H), 8.81 (d, 1H). |
| 361 | 2.60 (s, 3H), 6.93 (dd, 1H), 7.21 (t, 1H), 7.35 (m, 1H), 7.47-7.51 (m, 3H), 8.83 (d, 1H). |
| 363 | 1.06 (m, 2H), 1.25 (m, 2H), 2.29 (m, 1H), 6.96 (dd, 1H), 7.29-7.38 (m, 3H), 7.43-7.53 (m, 3H), 8.83 (d, 1H). |
| 364 | 2.00 (s, 3H), 5.79 (s, 1H), 6.06 (s, 1H), 6.90 (d, 1H), 7.26-7.37 (m, 3H), 7.45-7.51 (m, 2H), 7.57 (m, 1H), 8.78 (br, 1H). |
| 365 | 1.33 (s, 9H), 6.90 (dd, 1H), 7.26-7.37 (m, 3H), 7.46-7.51 (m, 2H), 7.54 (m, 1H), 8.81 (d, 1H). |
| 367 | 2.62 (s, 3H), 2.65 (s, 3H), 2.80 (s, 3H), 6.59 (d, 1H), 6.92 (t, 1H), 7.26-7.39 (m, 2H), 7.48-7.51 (m, 3H). |
| 368 | 6.95 (d, 1H), 7.2-7.7 (m, 10H), 7.87 (m, 1H), 8.64 (d, 1H). |
| 371 | 0.91 (t, 3H), 1.38 (m, 2H), 1.70 (m, 2H), 2.89 (t, 2H), 6.88 (d, 1H), 7.2-7.6 (m, 6H), 8.82 (d, 1H). |
| 373 | 6.66 (s, 1H), 6.76 (d, 1H), 7.04 (t, 1H), 7.36-7.56 (m, 4H), 7.73 (d, 1H), 8.84 (d, 1H). |

TABLE 39

| Compound No | ¹H-NMR |
|---|---|
| 374 | 6.79 (d, 1H), 7.04 (t, 1H), 7.35-7.56 (m, 4H), 7.74 (s, 1H), 8.82 (d, 1H). |
| 375 | 2.46 (s, 3H), 6.86 (d, 1H), 7.2-7.7 (m, 6H), 8.80 (d, 1H). |
| 376 | 1.57 (s, 6H), 2.7 (bs, 1H), 6.89 (dd, 1H), 7.2-7.7 (m, 6H), 8.82 (d, 1H). |
| 377 | 1.24 (d, 6H), 3.16 (sep, 1H), 6.88 (d, 1H), 7.2-7.6 (m, 6H), 8.81 (d, 1H). |
| 382 | 2.59 (s, 3H), 2.69 (s, 3H), 6.69 (d, 1H), 6.99 (t, 1H), 7.25 (m, 1H), 7.33-7.41 (m, 3H), 8.00 (m, 1H). |
| 383 | 2.61 (s, 3H), 2.69 (s, 3H), 6.62 (d, 1H), 6.97 (t, 1H), 7.24-7.37 (m, 2H), 7.48 (s, 1H), 7.61-7.69 (m, 2H). |
| 384 | 2.15 (s, 3H), 5.11 (s, 2H), 6.78 (d, 1H), 7.03 (t, 1H), 7.33-7.53 (m, 4H), 7.64 (d, 1H), 8.84 (d, 1H). |
| 388 | 2.61 (s, 3H), 6.80 (d, 1H), 7.02 (m, 1H), 7.22 (m, 1H), 7.39 (m, 1H), 7.58 (m, 1H), 7.79 (d, 1H), 7.92 (d, 1H), 8.81 (d, 1H). |
| 389 | 2.60 (s, 3H), 2.69 (s, 3H), 6.67 (d, 1H), 6.98 (t, 1H), 7.32-7.45 (m, 3H), 7.58 (d, 1H), 8.03 (s, 1H). |
| 390 | 6.76 (d, 1H), 7.04 (t, 1H), 7.40 (m, 1H), 7.47-7.57 (m, 3H), 7.75 (s, 1H), 8.82 (d, 1H). |
| 397 | 1.53 (bs, 6H), 2.73 (s, 3H), 6.67 (d, 1H), 6.99 (t, 1H), 7.2-7.7 (m, 5H). |
| 398 | 1.53 (d, 6H), 6.98 (t, 1H), 7.3-7.7 (m, 5H), 8.81 (d, 1H). |
| 401 | 6.97 (d, 1H), 7.10 (t, 1H), 7.26-7.38 (m, 3H), 7.46-7.75 (m, 7H), 8.14 (d, 1H), 8.35 (d, 1H), 8.91 (d, 1H), 9.36 (s, 1H). |
| 402 | 3.94 (s, 3H), 6.87 (d, 1H), 7.24-7.35 (m, 2H), 7.56 (t, 1H), 7.61-7.73 (m, 3H), 8.11 (d, 1H), 8.79 (d, 1H). |
| 403 | 3.89 (s, 3H), 6.92 (d, 1H), 7.26 (t, 1H), 7.43 (d, 1H), 7.54 (t, 1H), 7.61-7.74 (m, 3H), 8.11 (d, 1H), 8.79 (d, 1H). |
| 409 | 1.19 (t, 3H), 2.33 (d, 3H), 4.27 (q, 2H), 6.78 (d, 1H), 7.29-7.35 (m, 2H), 7.44-7.48 (m, 3H), 8.84 (d, 1H). |

TABLE 39-continued

| Compound No | $^1$H-NMR |
|---|---|
| 410 | 1.41 (s, 9H), 6.97 (d, 1H), 7.28-7.38 (m, 3H), 7.45-7.49 (m, 3H), 8.85 (d, 1H). |
| 427 | 1.33 (d, 3H), 2.80 (s, 3H), 3.38 (s, 3H), 4.00 (m, 1H), 6.77 (d, 1H), 7.03 (m, 1H), 7.25-7.45 (m, 5H). |
| 428 | 1.02 (t, 3H), 1.36 (s, 3H), 1.79 (q, 2H), 2.18 (s, 1H), 2.79 (s, 3H), 6.75 (d, 1H), 7.03 (m, 1H), 7.28-7.45 (m, 5H). |
| 430 | 1.03 (t, 3H), 1.28 (m, 2H), 1.68 (m, 2H), 3.90 (q, 2H), 6.79 (d, 1H), 6.97 (t, 1H), 7.26-7.35 (m, 2H), 7.40-7.50 (m, 3H), 8.83 (d, 1H). |
| 431 | 0.66-0.87 (m, 2H), 1.12-1.19 (m, 2H), 1.26-1.29 (m, 8H), 1.99 (s, 1H), 6.67 (d, 1H), 6.89 (m, 1H), 7.18 (m, 1H), 7.34 (m, 1H), 7.47-7.50 (m, 2H), 7.62 (m, 1H), 8.82 (d, 1H). |
| 435 | 1.82 (d, 6H), 5.28 (br, 2H), 6.62 (d, 1H), 6.87 (dd, 1H), 7.19 (m, 1H), 7.33 (m, 1H), 7.43-7.51 (m, 2H), 7.68 (m, 1H), 8.79 (d, 1H). |
| 437 | 1.93 (d, 6H), 6.72 (m, 1H), 6.91-6.98 (m, 2H), 7.19-7.38 (m, 2H), 7.43-7.52 (m, 2H), 7.58 (m, 1H), 8.83 (d, 1H) |
| 442 | 2.46 (s, 6H), 5.22 (s, 1H), 6.8-7.0 (m, 1H), 7.2-7.5 (m, 5H), 7.67 (dd, 1H), 8.84 (d, 1H). |

TABLE 40

| Compound No | $^1$H-NMR |
|---|---|
| 443 | 2.07 (s, 3H), 6.78 (d, 1H), 6.80 (bs, 1H), 7.03 (d, 1H), 7.2-7.6 (m, 5H), 7.78 (m, 1H), 8.88 (d, 1H). |
| 445 | 1.54 (dd, 3H), 1.61-1.69 (m, 4H), 2.34-2.39 (m, 2H), 2.54-2.59(m, 2H), 3.92 (q, 1H), 6.79 (m, 1H), 6.97 (m, 1H), 7.22-7.33 (m, 2H), 7.39 (m, 1H), 7.43-7.47 (m, 2H), 8.83 (d, 1H) |
| 446 | 1.47 (d, 3H), 1.54 (s, 9H), 3.29 (s, 3H), 4.97 (q, 1H), 6.67 (d, 1H), 7.2-7.5 (m, 5H), 8.04 (d, 1H), 8.66 (bs, 1H), 8.85 (d, 1H). |
| 447 | 1.50 (d, 3H), 3.26 (s, 3H), 4.88 (bs, 2H), 4.93 (q, 2H), 6.33 (dd, 1H), 6.52 (dd, 1H), 7.07 (t, 1H), 7.2-7.5 (m, 4H), 8.84 (d, 1H). |
| 448 | 1.47 (d, 3H), 2.89 (d, 3H), 3.23 (s, 3H), 4.94 (q, 2H), 5.78 (bs, 1H), 6.30 (dd, 1H), 6.51 (d, 1H), 7.19 (t, 1H), 7.24-7.43 (m, 5H), 8.84 (d, 1H). |
| 449 | 2.11 (br, 6H), 2.84 (s, 3H), 2.92 (s, 3H), 6.68 (m, 1H), 6.96 (m, 1H), 7.27-7.44 (m, 4H), 7.49 (d, 1H). |
| 450 | 2.11 (d, 6H), 2.91 (s, 3H), 6.74 (m, 1H), 6.97 (m, 1H), 7.29-7.51 (m, 3H), 7.67 (m, 1H), 8.82 (d, 1H). |
| 451 | 2.16 (br, 6H), 2.81 (s, 3H), 2.92 (s, 3H), 6.65 (d, 1H), 6.98 (m, 1H), 7.26-7.42 (m, 3H), 7.50 (s, 1H). |
| 452 | 1.38 (t, 3H), 2.11 (s, 6H), 3.08 (q, 2H), 6.76 (d, 1H), 6.98 (m, 1H), 7.30-7.38 (m, 2H), 7.47-7.54 (m, 2H), 7.70 (d, 1H), 8.84 (d, 1H). |
| 453 | 1.99 (d, 3H), 2.95 (s, 3H), 5.20 (q, 1H), 6.84 (m 1H), 7.23-7.55 (m, 5H), 7.78 (m, 1H), 8.83 (d, 1H). |
| a-2 | 1.67 (s, 6H), 6.00 (s, 1H), 7.54-7.61 (m, 2H), 7.66-7.74 (m, 2H), 8.14 (d, 1H), 8.38 (t, 1H), 8.80 (d, 1H). |
| a-7 | 1.66 (s, 6H), 2.81 (s, 3H), 6.02 (s,. 1H), 7.19-7.43 (m, 6H), 8.40 (d, 1H). |
| a-8 | 1.65 (s, 6H), 5.96 (s, 1H), 7.25-7.39 (m, 3H), 7.48-7.58 (m, 3H), 8.41 (m, 1H), 8.85 (d, 1H). |
| b-1 | 1.18 (s, 6H), 1.50 (s, 6H), 1.75-1.93 (m, 4H), 2.73 (t, 2H), 2.84 (s, 1H), 2.89 (t, 2H), 6.82 (dd, 1H), 6.96 (d, 1H), 7.08-7.20 (m, 2H), 7.49 (dd, 1H), 8.10 (d, 1H). |
| b-3 | 1.27 (s, 6H), 1.60 (s, 6H), 1.76-1.94 (m, 4H), 2.49 (s, 1H), 2.74 (t, 2H), 2.90 (t, 2H), 6.62 (d, 1H), 6.79-6.86 (m, 1H), 6.97 (d, 1H), 7.08-7.15 (m, 1H), 8.10 (d, 1H). |
| b-4 | 1.19 (s, 6H), 1.50 (s, 6H), 2.11-2.21 (m, 2H), 2.83 (s, 1H), 2.90 (t, 2H), 2.95 (t, 2H), 6.81 (dd, 1H), 7.08-7.21 (m, 3H), 7.50 (dd, 1H), 8.08 (d, 1H). |
| b-5 | 1.19 (s, 6H), 1.50 (s, 6H), 1.62-1.73 (m, 4H), 1.83-1.90 (m 2H), 2.70-2.73 (m, 2H), 2.92 (s, 1H), 3.00-3.04 (m, 2H), 6.84 (dd, 1H), 7.01 (d, 2H), 7.07-7.20 (m, 2H), 7.48 (dd, 1H), 8.00 (d, 1H). |
| b-6 | 1.76-1.95 (m, 4H), 2.59 (s, 3H), 2.75 (t, 2H), 2.91 (t, 2H), 6.63 (d, 1H), 6.88 (t, 1H), 7.03 (d, 1H), 7.24-7.32 (m, 1H), 8.16 (m, 1H). |
| b-7 | 1.74 (d, 6H), 1.74-1.95 (m, 4H), 2.76 (t, 2H), 2.92 (t, 2H), 4.26 (d, 1H), 6.55 (dd, 1H), 6.79-6.86 (m, 1H), 7.05 (d, 1H), 7.07-7.15 (m, 1H), 8.18 (d, 1H). |
| b-8 | 1.03 (s, 9H), 1.71 (d, 3H), 1.74-1.95 (m, 4H), 2.75 (t, 2H), 2.91 (t, 2H), 5.00 (s, 1H), 6.53 (d, 1H), 6.77-6.84 (m, 1H), 7.06 (s, 1H), 7.08-7.26 (m, 1H), 8.20 (d, 1H). |
| b-9 | 1.63 (d, 3H), 1.76-1.95 (m, 4H), 2.75 (t, 2H), 2.77-2.93 (m, 2H), 3.48 (s, 1H), 5.29-5.34 (m, 1H), 6.55 (d, 1H), 6.81 (dd, 1H), 7.03 (d, 1H), 7.13 (q, 1H), 8.16(d, 1H). |

TABLE 41

| Compound No | $^1$H-NMR |
|---|---|
| b-10 | 1.59 (d, 3H), 1.65-1.94 (m, 4H), 2.74 (t, 2H), 2.90 (t, 2H), 3.27 (s, 3H), 4.90 (q, 1H), 6.62 (d, 1H), 6.84 (dd, 1H), 6.89 (d, 1H), 7.14-7.22 (m, 1H), 8.11 (d, 1H). |
| b-11 | 2.65 (s, 3H), 6.65 (d, 1H), 6.92 (t, 1H), 7.21 (d, 1H), 7.27-7.35 (m, 1H), 7.61 (d, 1H), 7.69 (d, 1H), 8.43 (d, 1H). |
| b-12 | 1.77 (d, 6H), 4.16 (d, 1H), 6.57 (d, 1H), 6.86 (dd, 1H), 7.09-7.18 (m, 1H), 7.20 (d, 1H), 7.61 (d, 1H), 7.69 (d, 1H), 8.44 (d, 1H). |
| b-13 | 1.17 (s, 6H), 1.53 (s, 6H), 2.92 (s, 3H), 2.92 (t, 2H), 3.41 (s, 1H), 3.48 (t, 2H), 6.78 (d, 1H), 6.91 (d, 1H), 6.92-7.15 (m, 2H), 7.42 (dd, 1H), 7.65 (d, 1H). |
| b-14 | 1.67 (d, 3H), 2.75 (dd, 1H), 5.31-5.41 (m, 1H), 6.58 (d, 1H), 6.87 (m, 1H), 7.12-7.21 (m, 2H), 7.61 (d, 1H), 7.67 (d, 1H), 8.44 (d, 1H). |
| b-15 | 1.59 (d, 3H), 3.29 (s, 3H), 4.93 (q, 1H), 6.65 (d, 1H), 6.90 (t, 1H), 7.07-7.25 (m, 2H), 7.58 (d, 1H), 7.64 (s, 1H), 8.41 (d, 1H). |

TABLE 41-continued

| Compound No | ¹H-NMR |
|---|---|
| b-16 | 1.06 (s, 9H), 1.75 (d, 3H), 4.93 (s, 1H), 6.54 (d, 1H), 6.84 (dd, 1H), 7.07-7.12 (m, 1H), 7.13 (d, 1H), 7.61 (d, 1H), 7.75 (d, 1H), 8.45 (d, 1H). |
| b-19 | 1.50 (s, 3H), 1.67 (s, 3H), 1.81-1.97 (m, 4H), 2.80 (m, 2H), 2.97 (m, 2H), 5.90 (s, 1H), 7.19-7.37 (m, 3H), 7.72 (m, 1H), 8.55 (d, 1H). |
| b-20 | 1.52 (s, 3H), 1.58 (s, 3H), 5.88 (s, 1H), 7.23-7.42 (m, 4H), 7.62 (d, 1H), 8.38 (d, 1H), 8.83 (d, 1H). |
| b-21 | 2.59 (s, 3H), 2.80 (t, 2H), 4.07 (t, 2H), 4.73 (s, 2H), 6.65 (d, 1H), 6.91 (t, 1H), 6.97 (d, 1H), 7.28-7.35 (m, 1H), 8.24 (d, 1H). |
| b-22 | 1.73 (d, 6H), 2.02 (s, 1H), 3.02 (t, 2H), 4.07 (t, 2H), 4.73 (s, 2H), 6.57 (d, 1H), 6.82-6.89 (m, 1H), 6.98 (d, 1H), 7.10-7.15 (m, 1H), 8.25 (d, 1H). |
| b-23 | 2.63 (s, 3H), 6.60 (d, 1H), 6.77 (d, 2H), 6.89 (t, 1H), 7.25-7.32 (m, 1H), 7.62 (d, 1H), 7.76 (d, 1H), 8.16 (d, 1H). |

(Formulation)

Examples of the fungicide according to the present invention are shown below, however, adding agents and the addition ratio are not limited to these examples and it is possible to vary them extensively. Also, parts in formulation examples represent parts by weight.

| Formulation example 1 Water-dispersible powder | |
|---|---|
| The compound according to the present invention | 40 parts |
| Clay | 48 parts |
| Sodium dioctylsulfo succinate | 4 parts |
| Sodium lignin sulfonate | 8 parts |

The above were uniformly mixed and finely pulverized to obtain water-dispersible powder with 40% active ingredient.

| Formulation example 2 Emulsion | |
|---|---|
| The compound according to the present invention | 10 parts |
| SORVESSO 200 | 53 parts |
| Cyclohexanone | 26 parts |
| Potassium dodecylbenzene sulfonate | 1 part |
| Polyoxyethylene alkylallylether | 10 parts |

The above were mixed and dissolved to obtain an emulsion with 10% active ingredient.

| Formulation example 3 Powder | |
|---|---|
| The compound according to the present invention | 10 parts |
| Clay | 90 parts |

The above were uniformly mixed and finely pulverized to obtain powder with 10% active ingredient.

| Formulation example 4 Granule | |
|---|---|
| The compound according to the present invention | 5 parts |
| Clay | 73 parts |
| Bentonite | 20 parts |
| Sodium dioctylsulfo succinate | 1 part |
| Potassium phosphate | 1 part |

The above were well pulverized, mixed, and well kneaded with an addition of water, followed by granulating and drying to obtain granule with 5% active ingredient.

| Formulation example 5 Suspension | |
|---|---|
| The compound according to the present invention | 10 parts |
| Polyoxyethylene alkyallylether | 4 parts |
| Sodium polycarboxylate | 2 parts |
| Glycerine | 10 parts |
| Xanthane gum | 0.2 parts |
| Water | 73.8 parts |

The above were mixed and wet pulverized until the particle diameter becomes equal to or less than 3 micron to obtain a suspension with 10% active ingredient.

| Formulation example 6 Water-dispersible granule | |
|---|---|
| The compound according to the present invention | 40 parts |
| Clay | 36 parts |
| Potassium chloride | 10 parts |
| Sodium alkylbenzene sulfonate | 1 part |
| Sodium lignin sulfonate | 8 parts |
| Formaldehyde condensation product of sodium alkylbenzene sulfonate | 5 parts |

The above were mixed and finely pulverized, followed by adding a suitable amount of water and kneading therewith to be in clay shape. The clay shaped material was granulated and dried to obtain water-dispersible granule with 40% active ingredient.

Biological Test Example 1

Control Test of Apple Scab

To apple seedlings grown in clay pots (Varieties "Rails Janet", 3 to 4 leaf base), the emulsion of the compound according to the present invention with active ingredient of concentration of 100 ppm was sprayed. After being air dried at room temperature, a conidium of apple scab bacteria (*Venturia inaqualis*) was inoculated, and was held for 2 weeks in a room at 20° C. under a high humidity, with light and darkness being repeated every 12 hours. Controlling effect was determined by comparing the state of the appearance of lesion on the leaves with that of untreated.

To compounds represented by Compound Numbers 3, 6, 7, 8, 10, 11, 12, 14, 15, 16, 17, 18, 19, 20, 21, 22, 24, 25, 26, 28, 29, 30, 31, 33, 34, 35, 36, 37, 38, 40, 41, 43, 44, 45, 46, 48, 49, 52, 53, 54, 57, 59, 60, 61, 62, 63, 64, 65 and 66, control test of an apple scab was carried out. As a result, all of the compounds showed at least 75% protective value.

Also, the same test was carried out to compounds represented by Compound Numbers 67, 68, 70, 73, 74, 75, 76, 77, 78, 79, 80, 82, 83, 84, 85, 86, 87, 88, 89, 90, 91, 92, 93, 94, 95, 96, 97, 98, 100, 101, 102, 103, 104, 105, 106, 107, 108, 109, 110, 111, 113, 114, 115, 116, 117, 118, 119, 120, 121, 122, 123, 124, 125, 126, 127, 128, 131, 132, 133, 134, 135, 136, 137, 138, 139, 140, 141, 142, 143, 144, 145, 146, 147, 148, 149, 150, 151, 152, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 190, 192, 193, 194, 195, 196, 197, 198, 199, 200, 201, 202, 203, 204, 205, 206, 207, 208, 209, 210, 211, 215, 217, 218, 219, 220, 221, 222, 223, 224, 225, 227, 228, 229, 230, 231, 232, 233, 234, 235, 236, 237, 238, 239, 240, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 276, 277, 278, 279, 280, 281, 283, 284, 285, 288, 289, 290, 291, 292, 293, 294, 295, 296, 297, 298, 299, 300, 306, 308, 309, 310, 311, 314, 315, 316, 317, 318, 319, 320, 321, 322, 323, 324, 325, 327, 328, 329, 330, 331, 332, 333, 334, 335, 344, 347, 348, 349, 350, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 402, 403, 404, 406, 407, 408, 409, 410, 411, 412, 413, 414, 416, 417, 418, 419, 423, 424, 425, 426, 427, 428, 429, 430, 431, 432, 433, 434, 435, 437, 439, 440, 441, 442, 443, 445, a-2, a-3, a-4, a-5, a-6, a-7, a-8, a-9, a-10, b-1, b-2, b-3, b-4, b-5, b-6, b-7, b-8, b-9, b-10, b-11, b-12, b-13, b-14, b-15, b-16, b-17, b-20, b-22, b-23, b-24, c-2, c-3, c-4, c-5, d-5, and d-6. As a result, all of the compounds showed at least 75% protective value.

Biological Test Example 2

Control Test of Cucumber Gray Mold

To cucumber seedlings grown in clay pots (Varieties "*Cucumis sativus* L.", cotyledon base), the emulsion of the compound according to the present invention with active ingredient of concentration of 100 ppm was sprayed. After being air dried at room temperature, a conidium suspension of cucumber gray mold bacteria (*Botrytis cinerea*) was dropwise inoculated, and was held for 4 days in a dark room at 20° C. under a high humidity. Controlling effect was determined by comparing the state of the appearance of lesion on the leaves with that of untreated.

To compounds represented by Compound Numbers 10, 11, 12, 15, 18, 19, 22, 26, 29, 30, 31, 33, 34, 35, 36, 37, 38, 42, 43, 44, 48, 49, 54, 57, and 59, control test of a cucumber gray mold was carried out. As a result, all of the compounds showed at least 75% protective value.

Also, the same test was carried out to compounds represented by Compound Numbers 67, 73, 75, 76, 77, 80, 81, 82, 83, 86, 88, 89, 90, 92, 93, 94, 95, 96, 97, 98, 99, 100, 101, 102, 104, 106, 107, 108, 109, 110, 111, 113, 114, 115, 116, 117, 118, 119, 122, 123, 124, 125, 126, 127, 128, 133, 134, 138, 139, 140, 141, 142, 143, 144, 145, 146, 147, 148, 149, 150, 151, 152, 153, 156, 157, 158, 159, 160, 162, 163, 164, 166, 167, 168, 169, 170, 171, 172, 173, 174, 175, 176, 177, 178, 179, 180, 181, 183, 184, 185, 186, 187, 188, 192, 197, 198, 199, 200, 201, 202, 203, 205, 208, 209, 210, 219, 220, 221, 222, 223, 225, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 274, 275, 278, 281, 284, 285, 291, 292, 293, 295, 296, 297, 298, 299, 308, 309, 310, 311, 314, 315, 316, 317, 318, 319, 323, 324, 325, 326, 327, 328, 332, 333, 338, 340, 344, 348, 353, 355, 359, 360, 361, 363, 364, 365, 371, 375, 376, 377, 378, 379, 380, 381, 382, 386, 391, 392, 393, 395, 397, 398, 399, 402, 403, 405, 406, 412, 414, 416, 417, 418, 423, 424, 425, 426, 427, 428, 429, 431, 432, 433, 434, 435, 436, 437, 439, 440, 441, 442, 444, a-2, a-5, a-6, a-7, a-8, a-10, b-1, b-2, b-3, b-7, b-8, b-12, b-16, c-3, and c-4. As a result, all of the compounds showed at least 75% protective value.

Biological Test Example 3

Submerged Application Test of Rice Neck Rot

Rice seedlings were grown in pots where commercially available hilling is in a submerged condition (Varieties "koshihikari", 1 leaf base), and the emulsion of the compound according to the present invention with active ingredient of concentration of 400 ppm was drip treated to the surface of the water. After 2 days, a conidium suspension of rice neck rot bacteria (*Magnaporthe grisea*) was spray inoculated, was held for 2 days in a dark room at 25° C. under a high humidity, and then was held for 8 days in a room at 25° C., with light and darkness being repeated in every 12 hours. Controlling effect was decided by the following grades after comparing the state of the appearance of lesion on the leaves with that of untreated.

A (at least 60% protective value)

B (at least 40% but less than 60% protective value)

As a result of the present test, the controlling effect of the following compounds was evaluated as A.

Compound Number: 5, 20, 21, 23, 25, 28, 32, 33, 34, 36, 37, 38, 43, 44, 48, 58, 66, 70, 71, 73, 78, 84, 85, 88, 89, 90, 106, 107, 227, 228, 234, 236, 260, 262, 348, 353, 356, 358, 375, 376, 401, 402, a-6

Also, the controlling effect of the following compounds was evaluated as B.

Compound Number: 1, 3, 7, 12, 13, 22, 46, 54, 55, 75, 95, 98, 139, 151, 261, 359, 360, b-1

Biological Test Example 4

Submerged Application Test of Rice Neck Rot

Rice seedlings were grown in pots where commercially available hilling is in a submerged condition (Varieties "koshihikari", 1 leaf base), and the emulsion of the compound according to the present invention with active ingredient of concentration of 400 ppm was drip treated to the surface of the water. After 14 days, a conidium suspension of rice neck rot bacteria (*Magnaporthe grisea*) was spray inoculated, was held for 2 days in a dark room at 25° C. under a high humidity, and then was held for 8 days in a room at 25° C., with light and darkness being repeated in every 12 hours. Controlling effect was decided by the following grades after comparing the state of the appearance of lesion on the leaves with that of untreated.

A (at least 60% protective value)

B (at least 40% but less than 60% protective value)

As a result of the present test, the controlling effect of the following compounds was evaluated as A.

Compound Number: 21, 36, 37, 38, 43, 44, 48, 84, 88, 89, 95, 106, 109, 125, 262, 266, 267, 292, 350, 375, a-6

Also, the controlling effect of the following compound was evaluated as B.

Compound Number: 236

Biological Test Example 5

Seed Treatment Test of Cucumber Wilt

Cucumber seeds (Varieties "*Cucumis sativus* L.") contaminated by cucumber wilt bacteria (*Fusarium oxysporum*) were treated with the emulsion of the compound according to the present invention to obtain the seeds containing 1 g/kg active ingredient. The seeds were sowed and after 3 weeks, controlling effect was determined by comparing the degree of disease occurrence with that of untreated.

As a result, the following compounds showed an excellent protective value of at least 75%.

Compound Number: 18, 36, 37, 43, 44, 48, 77, 81, 83, 88, 92, 94, 100, 103, 109, 126, 225, 227, 228, 234, 235, 241, 242, 243, 244, 252, 258, 266, 268, 298, 395, 397, 425, 435, a-6, a-7, a-8, b-8, b-12, c-4

Biological Test Example 6

Seed Treatment Test of Cucumber Wilt

Cucumber seeds (Varieties "*Cucumis sativus* L.") were treated with the emulsion of the compound according to the present invention to obtain the seeds containing 1 g/kg active ingredient. The seeds were sowed in soil contaminated by cucumber wilt bacteria (*Fusarium oxysporum*) and, after 3 weeks, controlling effect was determined by comparing the degree of disease occurrence with that of untreated.

As a result, the following compounds showed an excellent protective value of at least 75%.

Compound Number: 17, 18, 31, 33, 34, 35, 36, 37, 43, 86, 88, 96, 97, 100, 109, 227, 232, 239, 242, 243, 244, 262, 265, 268, 295, 296, 375, 428, a-7, b-1.

The invention claimed is:

1. A nitrogen-containing heterocyclic compound represented by Formula (II):

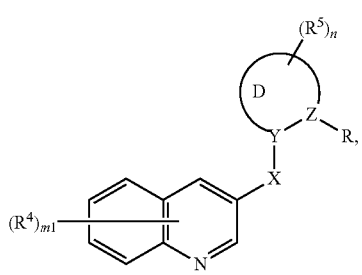

(II)

or a salt thereof, or an N-oxide compound thereof,
wherein, in Formula (II), R represents a group represented by $CR^1R^2R^3$;
$R^1$, $R^2$ and $R^3$, each independently represents a hydrogen atom, an unsubstituted or substituted $C_{1-8}$ alkyl group, an unsubstituted $C_{2-8}$ alkenyl group, an unsubstituted $C_{2-8}$ alkynyl group, an unsubstituted $C_{3-8}$ cycloalkyl group, an unsubstituted $C_{4-8}$ cycloalkenyl group, an unsubstituted $C_{6-10}$ aryl group, an unsubstituted heterocyclic group, an unsubstituted $C_{1-8}$ acyl group, an unsubstituted (1-imino)$C_{1-8}$ alkyl group, an unsubstituted or substituted carboxyl group, an unsubstituted or substituted carbamoyl group, an unsubstituted or substituted hydroxyl group, an unsubstituted or substituted amino group, a halogeno group, a cyano group, or a nitro group;
excepting in which: $R^1$, $R^2$ and $R^3$ are all hydrogen atoms; $R^1$, $R^2$ and $R^3$ are all unsubstituted $C_{1-8}$ alkyl groups; any one of $R^1$, $R^2$ and $R^3$ is a hydrogen atom and the remaining two are both unsubstituted $C_{1-8}$ alkyl groups; and, any one of $R^1$, $R^2$ and $R^3$ is an unsubstituted $C_{1-8}$ alkyl group and the remaining two are both hydrogen atoms;
$R^1$ and $R^2$ may be joined to form O=;
$R^4$ each independently represents an unsubstituted or substituted $C_{1-8}$ alkyl group, an unsubstituted $C_{2-8}$ alkenyl group, an unsubstituted $C_{2-8}$ alkynyl group, an unsubstituted $C_{3-8}$ cycloalkyl group, an unsubstituted or substituted hydroxyl group, a halogeno group, a cyano group, or a nitro group;
m1 represents a number of $R^4$ and is an integer of 0 to 6;
$R^5$ each independently represents an unsubstituted or substituted $C_{1-8}$ alkyl group, an unsubstituted $C_{2-8}$ alkenyl group, an unsubstituted $C_{2-8}$ alkynyl group, an unsubstituted $C_{3-8}$ cycloalkyl group, an unsubstituted or substituted hydroxyl group, a halogeno group, a cyano group, or a nitro group;
n represents a number of $R^5$ and is an integer of 0 to 5;
D represents a 5- to 7-membered hydrocarbon ring or a 5- to 7-membered heterocyclic ring;
X represents an oxygen atom;
Y represents a carbon atom; and
Z represents a carbon atom; and
wherein the substituted $C_{1-8}$ alkyl group is a $C_{3-6}$ cycloalkyl $C_{1-6}$ alkyl group, a $C_{4-6}$ cycloalkenyl $C_{1-6}$ alkyl group, a $C_{1-6}$ haloalkyl group, a $C_{6-10}$ aryl $C_{1-6}$ alkyl group, 5- to 6-membered heteroaryl $C_{1-6}$ alkyl group, a hydroxyl $C_{1-6}$ alkyl group, a $C_{1-6}$ alkoxy $C_{1-6}$ alkyl group, a $C_{1-7}$ acyloxy $C_{1-6}$ alkyl group, a tri $C_{1-6}$ alkylsilyloxy $C_{1-6}$ alkyl group, a $C_{1-6}$ alkyl-substituted $C_{6-10}$ arylsulfonyloxy $C_{1-6}$ alkyl group, a cyano $C_{1-6}$ alkyl group, a $C_{1-6}$ acyl $C_{1-6}$ alkyl group, a 2-hydroxyimino $C_{2-6}$ alkyl group, a formyl $C_{1-6}$ alkyl group, a carboxy $C_{1-6}$ alkyl group, a $C_{1-6}$ alkoxycarbonyl $C_{1-6}$ alkyl group, or an azido $C_{1-6}$ alkyl group,
the substituted carboxyl group is a $C_{1-6}$ alkoxycarbonyl group, a $C_{2-6}$ alkenyloxycarbonyl group, a $C_{2-6}$ alkynyloxycarbonyl group, a $C_{6-10}$ aryloxycarbonyl group, or a $C_{6-10}$ aryl $C_{1-6}$ alkoxycarbonyl group,
the substituted carbamoyl group is a mono $C_{1-6}$ alkylcarbamoyl group, a di $C_{1-6}$ alkylcarbamoyl group, or a mono $C_{6-10}$ arylcarbamoyl group,
the substituted hydroxyl group is a $C_{1-6}$ alkoxy group, a $C_{3-8}$ cycloalkyl $C_{1-6}$ alkoxy group, a $C_{6-10}$ aryl $C_{1-6}$ alkoxy group, a $C_{1-6}$ haloalkoxy group, a $C_{2-6}$ alkenyloxy group, a $C_{2-6}$ alkynyloxy group, a $C_{3-6}$ cycloalkyloxy group, a $C_{6-10}$ aryloxy group, a $C_{6-10}$ aryl $C_{1-6}$ alkyloxy group, a $C_{1-7}$ acyloxy group, a $C_{1-6}$ alkoxycarbonyl $C_{1-6}$ alkoxy group, or a tri $C_{1-6}$ alkylsilyloxy group, and
the substituted amino group is a mono $C_{1-6}$ alkylamino group, a di $C_{1-6}$ alkylamino group, a mono $C_{1-6}$ alkylideneamino group, a mono $C_{6-10}$ arylamino group, a di $C_{6-10}$ arylamino group, a $C_{6-10}$ aryl $C_{1-6}$ alkylamino group, a $C_{1-6}$ acylamino group, or a $C_{1-6}$ alkoxycarbonylamino group.

2. A nitrogen-containing heterocyclic compound, a salt thereof, or an N-oxide compound, according to claim 1, wherein the nitrogen-containing heterocyclic compound is represented by Formula (III):

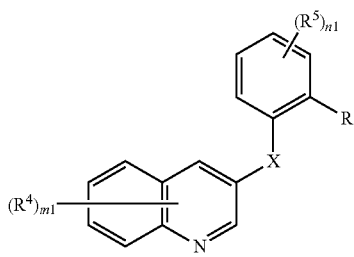

(III)

wherein each of R, $R^4$, $R^5$, m1 and X represents the same meaning as those in Formula (II); and n1 represents a number of $R^5$ and is an integer of 0 to 4.

3. An agricultural fungicide comprising, as an active ingredient, at least one selected from the group consisting of the nitrogen-containing heterocyclic compound, the salt thereof, and the N-oxide compound thereof, of claim 1.

4. A nitrogen-containing heterocyclic compound, a salt thereof, or an N-oxide compound, according to claim 1, wherein $R^1$ represents the unsubstituted or substituted hydroxyl group, $R^2$ represents the hydrogen atom or the unsubstituted or substituted $C_{1-8}$ alkyl group, and $R^3$ represents the hydrogen atom, the unsubstituted or substituted $C_{1-8}$ alkyl group, the unsubstituted $C_{2-8}$ alkenyl group, the unsubstituted $C_{2-8}$ alkynyl group, the unsubstituted $C_{3-8}$ cycloalkyl group, the unsubstituted $C_{6-10}$ aryl group, the unsubstituted hererocyclic group, the unsubstituted $C_{1-8}$ acyl group, the unsubstituted (1-imino)$C_{1-8}$ alkyl group, the $C_{1-6}$ alkoxycarbonyl group, the unsubstituted or substituted hydroxyl group, or, the cyano group.

5. A nitrogen-containing heterocyclic compound, a salt thereof, or an N-oxide compound, according to claim 1, wherein $R^4$ represents a $C_{1-6}$ alkyl group, a $C_{1-6}$ haloalkyl group, a $C_{2-6}$ alkenyl group, a $C_{3-8}$ cycloalkyl group, a hydroxyl group, a $C_{1-6}$ alkoxy group, or a halogeno group.

6. A nitrogen-containing heterocyclic compound, a salt thereof, or an N-oxide compound according to claim 1, wherein $R^5$ represents a $C_{1-6}$ alkyl group, a $C_{1-6}$ haloalkyl group, a $C_{6-10}$ aryl $C_{1-6}$ alkyl group, a $C_{3-8}$ cycloalkyl group, a $C_{1-6}$ alkoxy group, a halogeno group, a cyano group or a nitro group.

7. A nitrogen-containing heterocyclic compound, a salt thereof, or an N-oxide compound, according to claim 6, wherein the nitrogen-containing heterocyclic compound is 2-[2-fluoro-6-(8-fluoroquinolin-3-yloxy)-phenyl]-3,3-dimethyl-butan-2-ol, 2-[2-fluoro-6-(8-fluoroquinolin-3-yloxy)-phenyl]-propan-2-ol, 2-[2-fluoro-6-(8-fluoro-2-methylquinolin-3-yloxy)-phenyl]-propan-2-ol, or 2-[2-fluoro-6-(7,8-difluoro-2-methylquinolin-3-yloxy)-phenyl]-propan-2-ol.

8. An agricultural fungicide for seed treatment comprising, as an active ingredient, at least one selected from the group consisting of the nitrogen-containing heterocyclic compound, the salt thereof, and the N-oxide compound thereof, of claim 1.

9. A method for treating a seed using an agricultural fungicide comprising, as an active ingredient, at least one selected from the group consisting of the nitrogen-containing heterocyclic compound, the salt thereof, and the N-oxide compound thereof, of claim 1.

* * * * *